(12) United States Patent
Paul et al.

(10) Patent No.: US 8,239,213 B1
(45) Date of Patent: Aug. 7, 2012

(54) SYSTEMS AND METHODS FOR SIMULATING A CHANGE TO A PRESCRIPTION DRUG PLAN

(75) Inventors: Les Paul, Greenville, DE (US); Amy Foley, Pompton Plains, NJ (US); Brian F. Ezrow, Quakertown, PA (US); David B. Snow, Jr., Darien, CT (US); Ella Berger, Fair Lawn, NJ (US); Robert S. Epstein, Upper Grandview, NY (US); Beth Bird, Chicago, IL (US); Marianne Jacks, Mountain Lakes, NJ (US); Tej Anand, Chappaqua, NY (US); Vicente L. Caride, New York, NY (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 1772 days.

(21) Appl. No.: 11/052,376

(22) Filed: Feb. 7, 2005

Related U.S. Application Data

(60) Provisional application No. 60/541,905, filed on Feb. 6, 2004.

(51) Int. Cl.
*G06Q 10/00* (2006.01)
*G06Q 50/00* (2006.01)

(52) U.S. Cl. .............................................. 705/2; 705/3

(58) Field of Classification Search ................. 705/2–3
See application file for complete search history.

(56) References Cited

U.S. PATENT DOCUMENTS

| | | | |
|---|---|---|---|
| 5,497,489 A | 3/1996 | Menne et al. | |
| 6,195,612 B1 | 2/2001 | Pack-Harris | |
| 6,317,719 B1 | 11/2001 | Schrier et al. | |
| 6,430,539 B1 | 8/2002 | Lazarus et al. | |
| 2001/0034613 A1* | 10/2001 | Rubsamen | 705/2 |
| 2002/0095314 A1 | 7/2002 | Bodsworth et al. | |
| 2002/0103680 A1* | 8/2002 | Newman | 705/4 |
| 2002/0147617 A1* | 10/2002 | Schoenbaum et al. | 705/4 |
| 2004/0138921 A1 | 7/2004 | Broussard et al. | |
| 2006/0242051 A1 | 10/2006 | Haggerty et al. | |

* cited by examiner

Primary Examiner — Sheetal R Rangrej
(74) Attorney, Agent, or Firm — Husch Blackwell LLP

(57) ABSTRACT

Systems and methods for simulating a change to a prescription drug plan may be provided. In response to receiving a request to simulate the change to the prescription drug plan, a prescription drug spend and/or trend application may retrieve data related to the prescription drug plan from a database. A model that includes a plurality of calculations to simulate the change may be applied to the retrieved data. A user computing device may be provided with an indication of an impact on the prescription drug plan responsive to the at least one change based at least in part on the application of the model to the retrieved data. The modeling of the change may be related, for example, to an option to reduce spend and/or trend as determined by the spend and/or trend application.

21 Claims, 57 Drawing Sheets

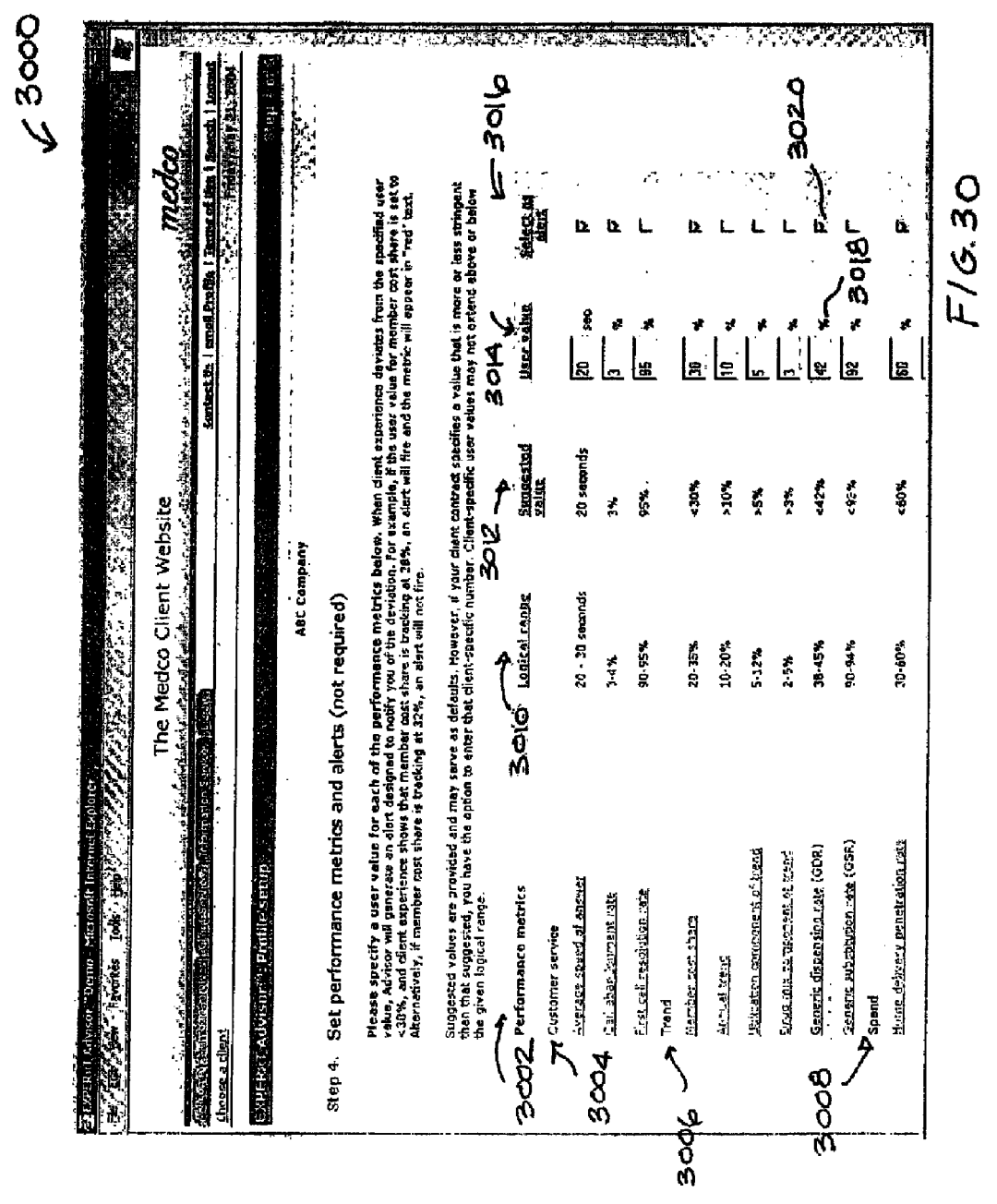

The Medco Client Website

ABC Company

EXPERT Advisor: Profile Setup

Step 4. Set performance metrics and alerts (not required)

Please specify a user value for each of the performance metrics below. When client experience deviates from the specified user value, Advisor will generate an alert designed to notify you of the deviation. For example, if the user value for member cost share is set to <30%, and client experience shows that member cost share is tracking at 26%, an alert will fire and the metric will appear in "red" text. Alternatively, if member cost share is tracking at 32%, an alert will not fire.

Suggested values are provided and may serve as defaults. However, if your client contract specifies a value that is more or less stringent than that suggested, you have the option to enter that client-specific number. Client-specific user values may not extend above or below the given logical range.

| Performance metrics | Logical range | Suggested value | User value | Select as alert |
|---|---|---|---|---|
| Customer service | | | | |
| Average speed of answer | 20 - 30 seconds | 20 seconds | 20 sec | ☐ |
| Call abandonment rate | 3-4% | 3% | 3 % | ☐ |
| First call resolution rate | 90-95% | 95% | 95 % | ☐ |
| Trend | | | | |
| Member cost share | 20-35% | <30% | 30 % | ☐ |
| Annual trend | 10-20% | >10% | 10 % | ☐ |
| Utilization component of trend | 5-12% | >5% | 5 % | ☐ |
| Price component of trend | 2-5% | >3% | 3 % | ☐ |
| Generic dispersion rate (GDR) | 38-45% | <42% | 42 % | ☐ |
| Generic substitution rate (GSR) | 90-94% | <95% | 92 % | ☐ |
| Spend | | | | |
| Home delivery penetration rate | 30-60% | <60% | 60 % | ☐ |

FIG. 30

The Medco Client Website

Please review and approve plan defaults for profile: 1234 Actives

Important note: Where possible, plan design information presented is actual for selected groups. In cases where multiple groups with varying plan designs were selected, the plan design displayed on this page represents the common plan design present in at least 70 percent of the selected groups.

| | |
|---|---|
| Formulary: | Preferred prescriptions |
| Administration: | Open |
| Inclusions: | N/A |
| Exclusions: | Over-the-counter products |
| Copay structure: | Flat dollar co-payment at mail & retail |

| | Retail | Home delivery |
|---|---|---|
| Generic | $2.00 | Generic $4.00 |
| Brand | $10.00 | Brand $15.00 |

Other benefit design attributes: view all available programs

Clinical management: view all available programs

Health Management (Positive Approaches℠):
- Asthma
- Cardiovascular
- Diabetes
- Digestive Health
- Hepatitis C
- Multiple Sclerosis Retail network: Custom

The Medco Client Website

ABC company
Creation date: 12/16/2003

Contact Us | eMail Profile | Terms of Use | Search | Logout
Friday, May 21, 2004

Run date: 1/16/2004

Model Inputs ← 4200

Actives
GI Coverage Management
Antisecretory
Prior Authorization with history details    Member Impact    632 ← 4206

Your client may have a shared savings or guarantee associated with Prior Authorization rules. If so, please enter the amounts in the input section below. Enter whole dollar amounts for cost per clinical review, whole numbers for Shared Savings Threshold and Client Savings Guarantee, and a percentage for Shared Savings Cost. If your client does not have shared savings or guarantees, please enter a 0 in each box.
Using the radio buttons, please indicate if the output should be based on Gross or Plan Cost.

Inputs ← 4202

| | | Outputs | Current | Proposed | Savings/(Loss) |
|---|---|---|---|---|---|
| Transaction cost per clinical review | $40 | Gross cost | $200,671,000 | $200,620,000 | $51,000 |
| Shared savings threshold | 1 | Cost share | $35,017,000 | $36,007,000 | $10,000 |
| Shared savings (Medco) | 50% | Plan cost | $164,654,000 | $164,613,000 | $41,000 |
| Client savings guarantee | 1 | PMPM | $43.26 | $46.24 | $0.02 |
| Savings basis: | Plan | PDS Attrition Rate | 22.4% | | |
| | | Clinical Review Rate | 77.4% | | |
| | | Clinical Review Denial Rate | 3.4% | | |
| | | Total Denial Rate | 25.1% | | |

Model Inputs

ABE company
Creation date: 12/18/2003

Actives

Total Member Cost Share should not exceed 50% in order to maintain Rebates.
This plan design structure will impact rebates. Therefore, please use the Formulary Option model to assess the rebate impact.
If the Home Delivery Advantage Results are negative, copays are not aligned! Go back and increase Home Delivery copays or coinsurance.

Inputs

| | Current | Proposed | |
|---|---|---|---|
| Retail | | | |
| Brand | $10.00 | $20.00 | Flat dollar |
| Generic | $2.00 | $10.00 | Flat dollar |
| Home Delivery | | | |
| Brand | $15.00 | $40.00 | Flat dollar |
| Generic | $4.00 | $20.00 | Flat dollar |
| Percent Generic Shift | | 50% | |
| Home Delivery Advantage | | | No |
| RRA Refill Threshold | | 2 | Include RRA |

Outputs

| | Current | Proposed | Savings/(Loss) |
|---|---|---|---|
| Gross cost | $200,671,000 | $197,853,000 | $2,838,000 |
| Cost share | $36,017,000 | $49,458,250 | $13,441,250 |
| Plan cost | $164,654,000 | $148,374,750 | $16,279,250 |
| PMPM | $16.26 | $11.69 | $4.57 |

Model results represent estimates based on current population demographics, utilization, drug mix and costs. Actual results may vary.

This model should only be used with Standard Formularies. It is not intended for Custom or Closed Formularies. The drugs listed represent input the % share of rebates by base, incentive and admin as stated in the contract. The drugs listed represent input the % share of rebates by Base, Incentive and admin as stated in the contract. Select which type of Rebate control and Formulary Administration Type your client currently has. If you are unsure, please contact your FA or Formulary Contracting. In the drug section, enter the proposed formulary status of each drug. In the third section, select the proposed market share shift. If selecting "Custom market share shift" enter market share shifts by drug in the "Proposed market share" column. Make sure the sum of the shares add up to 100% for each channel.

Inputs

| | Current | Rebate control |
|---|---|---|
| Base rebate share | 100 % | ● Standard control |
| Incentive rebate share | 0 % | ○ High control |
| Admin rebate share | 0 % | |
| Formulary administrative type | ● Open ○ Incentive | Proposed market share shift ● Custom ○ Standard |

| Drug name | Brand/Generic | Effective copay | Current market share | Proposed market share | Current formulary status | Proposed formulary status |
|---|---|---|---|---|---|---|
| Retail | | | | | | |
| Nexium | B | $10.00 | 34% | 28 % | Yes | ○ Yes ● No |
| Protonix | B | $10.00 | 9% | 10 % | Yes | ● Yes ○ No |
| Omeprazole | G | $2.00 | 34% | 37 % | Yes | ○ Yes ● No |
| Prevacid | B | $10.00 | 23% | 25 % | No | ● Yes ○ No |
| Home delivery | | | | | | |
| Nexium | B | $15.00 | 31% | 25 % | Yes | ○ Yes ● No |
| Protonix | B | $15.00 | 6% | 6 % | Yes | ○ Yes ● No |
| Omeprazole | G | $4.00 | 48% | 53 % | Yes | ● Yes ○ No |
| Prevacid | B | $15.00 | 15% | 16 % | No | ○ Yes ● No |

NOTE: All analyses are directional. Model specifications are refreshed as soon as updates are available.

SYSTEMS AND METHODS FOR SIMULATING A CHANGE TO A PRESCRIPTION DRUG PLAN

CROSS REFERENCE TO RELATED APPLICATIONS

This application claims the benefit under 35 U.S.C. §119(e) of U.S. Patent Application No. 60/541,905, filed Feb. 6, 2004, which is hereby incorporated by reference herein in its entirety.

This application is related to the following co-pending applications, which are hereby incorporated by reference herein in their entireties: U.S. patent application Ser. No. 11/052,701, filed Feb. 7, 2005, U.S. patent application Ser. No. 11/052,368, filed Feb. 7, 2005, and U.S. patent application Ser. No. 11/052,374, filed Feb. 7, 2005.

FIELD OF THE INVENTION

The present invention generally relates to systems and methods for computer implemented analysis of spend and/or trend for prescription drug plans. More particularly, the present invention relates to systems and methods for simulating a change to a prescription drug plan.

BACKGROUND OF THE INVENTION

Employers often provide employees with various benefits upon commencement of employment. These benefits typically include a prescription drug plan. Prescription drug plans can be quantified by their respective spend (i.e., the cost of prescription drugs under the plan) and trend (i.e., the rate of change in prescription drug spending over time). An employer's goal is to affect prescription drug spending under its prescription drug plan such that the plan's prescription drug trend is reduced.

Various factors in connection with an employer's prescription drug plan may have an effect on the plan's prescription drug trend. Such factors may include, for example, the number of tiers in the prescription drug plan, co-payment amounts, drug coverage rules, and usage of mail order for prescriptions. Additionally, certain drug events in the prescription drug market may affect an employer's prescription drug plan, such as patent expirations, introduction of a new drug, or a shift in a drug from prescription to over-the-counter.

Currently, to analyze an increase in prescription drug spending for a prescription drug plan, the prescription drug claims data for the plan is analyzed manually by the plan provider. The aim of the manual analysis is to attempt to identify areas of possible improvement in the prescription drug plan, and to provide suggestions to achieve reduced drug spending. However, due to the large quantity of claims data, such manual analysis can be error prone, costly, and difficult. Furthermore, manual analysis has been very limited in terms of functionality and/or benefits.

Accordingly, we have determined that it is desirable to provide a number of features and processes to analyze prescription drug spending, and trends associated therewith, that have heretofore never been provided. In addition, we have determined that it is desirable to provide a unique software for implementing the above functionality and processes.

SUMMARY OF THE INVENTION

In accordance with the present invention, systems and methods are provided for simulating a change to a prescription drug plan.

A prescription drug spend and trend application may be implemented on the prescription drug plan management system of the present invention. The spend and trend application may receive information about an existing prescription drug plan. The plan information may include, for example, plan design information, benefit design information, or any other suitable information in connection with the prescription drug plan. The spend and trend application may retrieve data in connection with the prescription drug plan, such as claims and membership data. Such data may be stored, for example, in an information warehouse for access by the spend and trend application. The spend and trend application may use the retrieved data and the plan profile information to analyze spend and trend for the prescription drug plan. Based on the spend and trend analysis, the spend and trend application may, for example, indicate deviations in the plan data from desired plan parameters, determine the primary components of the prescription drug plan's spend and trend, provide options for improving the prescription drug plan, and model the impact of a change to the prescription drug plan.

In some embodiments of the present invention, a method for modeling an impact of an option for reducing at least one of spend and trend for a prescription drug plan may be provided. A request may be received from a user computing device to process at least one of spend and trend for the prescription drug plan. In response to receiving the request to process at least one of spend and trend, data related to the prescription drug plan may be retrieved from a database. At least one of spend and trend for the prescription drug plan may be processed using the retrieved data. A determination may be made as to whether at least one option to reduce at least one of spend and trend for the prescription drug plan is available. If an option is available, an indication of the option may be provided to the user computing device. The option may include at least one change to the prescription drug plan. A request may be received to simulate the change to the prescription drug plan from the user computing device. In response to receiving the request, data related to the prescription drug plan may be retrieved from the database. A model that includes a plurality of calculations to simulate the change may be applied to the retrieved data. If the change is a change to a financial aspect of the prescription drug plan, then the applied model is a financial model. If the change is a change to a clinical aspect of the prescription drug plan, then the applied model is a clinical model. The user computing device may be provided with an indication of at least one of a financial and member impact on the prescription drug plan responsive to the change based at least in part on the application of the model to the retrieved data.

In one example, the financial model may include at least one of a formulary options model, a therapeutic class optimizer model, a specialty model, a Medicare coordination of benefits model, an inclusions/exclusions model, a member cost share model, a retail refill allowance model, a home delivery advantage model, a member pay the difference model, a generic bundle model, an out of pocket maximum model, a deductibles model, a patient safety program model, a benefit cap model, and a retail access density model. The formulary options model may include a plurality of calculations that determine a rebate impact of a change to at least one of formulary content and co-pays for the prescription drug plan. The therapeutic class optimizer model may include a plurality of calculations that estimate a rebate impact and a net cost impact of moving a particular drug on or off a formulary of the prescription drug plan for one or more therapeutic classes. The specialty model may include a plurality of calculations that determine an estimated drug spend impact and an estimated discount impact associated with implementing a specialty pharmacy offering. The Medicare coordination of benefits model may include a plurality of calculations that determine an estimated financial impact of implementing a Medicare Part B subrogation program for home delivery claims. The inclusions/exclusions model may include a plurality of calculations that determine an estimated impact of including or excluding a particular drug in the prescription drug plan that is typically considered for exclusion from coverage. The member cost share model may include a plurality of calculations that determine an impact of changes to at least one of open and incentive co-pay prescription drug plan structures comprising a plurality of tiers. The retail refill allowance model may include a plurality of calculations that determine an impact of a stand-alone retail refill allowance at a user specified threshold. The home delivery advantage model may include a plurality of calculations that determine an impact of a stand-alone home delivery advantage comprising retail and home delivery co-pay alignment. The member pay the difference model may include a plurality of calculations that determine an impact of at least one of a managed and sensitive member pay the difference program. The generic bundle model may include a plurality of sub-models related to generic drug utilization, such as dose duration, step therapy, incentive co-pay, and member pay the difference. The out of pocket maximum model may include a plurality of calculations that determine an impact of an out of pocket maximum both with and without a change to deductible or co-pay. The deductibles model may include a plurality of calculations that determine an impact of deductibles both with and without a change to out of pocket cost and co-pay. The patient safety program model may include a plurality of calculations that determine an estimated financial impact of implementing a patient safety program for the prescription drug plan. The benefit cap model may include a plurality of calculations that determine an impact of a benefit cap for the prescription drug plan. The retail access density model may include a plurality of calculations that determine a member impact of removing at least one chain prescription drug retailer from the prescription drug plan.

In another example, the clinical model may include at least one of a dose optimization model, a quantity per dispensing event model, a smart rules model, a traditional prior authorization model, and a new drug events model. The dose optimization model may include a plurality of calculations that determine an estimated financial impact and an estimated member impact of implementing dose optimization rules. The quantity per dispensing event model may include a plurality of calculations that determine an estimated financial impact and an estimated member impact of implementing quantity per dispensing event rules. The smart rules model may include a plurality of calculations that determine an estimated financial impact and an estimated member impact of implementing smart coverage authorization rules. The traditional prior authorization model may include a plurality of calculations that determine an estimated financial impact and an estimated member impact of implementing traditional prior authorization rules. The new drug events model may include a plurality of calculations that determine an estimated impact of a status change for a particular drug (e.g., an expiration of a patent for the drug, a new indication for the drug, a shift of the drug from prescription to over-the-counter, an introduction of the drug to the marketplace, and a withdrawal of the drug from the marketplace).

In some embodiments of the present invention, a system for modeling an impact of an option for reducing at least one of spend and trend for a prescription drug plan may be provided.

The system may include a server in communication with a user computing device and a database. The server may be configured to receive a request from the user computing device to process at least one of spend and trend for the prescription drug plan. In response to receipt of the request to process at least one of spend and trend, the server may retrieve data related to the prescription drug plan from the database. The server may process at least one of spend and trend for the prescription drug plan using the retrieved data. The server may determine whether at least one option is available to reduce at least one of spend and trend for the prescription drug plan. If an option is available, the server may provide an indication of the option to the user computing device. The option may include at least one change to the prescription drug plan. The server may receive a request to simulate the change to the prescription drug plan from the user computing device. In response to receipt of the request, the server may retrieve data related to the prescription drug plan from the database. The server may apply a model that includes a plurality of calculations to simulate the change to the prescription drug plan to the retrieved data. If the change is a change to a financial aspect of the prescription drug plan, then the server may apply a financial model. If the change is a change to a clinical aspect of the prescription drug plan, then the server may apply a clinical model. The server may provide the user computing device with an indication of at least one of a financial and member impact on the prescription drug plan responsive to change based at least in part on the application of the model to the retrieved data.

In one example, the financial model may include at least one of a formulary options model, a therapeutic class optimizer model, a specialty model, a Medicare coordination of benefits model, an inclusions/exclusions model, a member cost share model, a retail refill allowance model, a home delivery advantage model, a member pay the difference model, a generic bundle model, an out of pocket maximum model, a deductibles model, a patient safety program model, a benefit cap model, and a retail access density model. In another example, the clinical model may include at least one of a dose optimization model, a quantity per dispensing event model, a smart rules model, a traditional prior authorization model, and a new drug events model. (Definitions of both the financial and clinical models are provided hereinabove.)

In some embodiments of the present invention, a method for simulating at least one change to a prescription drug plan may be provided. A request may be received to simulate the change to the prescription drug plan from a user computing device. In response to receiving the request, data related to the prescription drug plan may be retrieved from a database. A model that includes a plurality of calculations to simulate the change to the prescription drug plan may be applied to the retrieved data. The user computing device may be provided with an indication of an impact (e.g., financial impact, member impact) on the prescription drug plan responsive to the change based at least in part on the application of the model to the retrieved data. In one example, the impact on the prescription drug plan may be an impact on gross cost, cost share, plan cost, per-member per-month cost, point of service attrition rate, clinical review rate, clinical review denial rate, total denial rate, number of plan members impacted, or any other suitable factor.

In another example, a request may be received from the user computing device to process at least one of spend and trend for the prescription drug plan. In response to receiving the request to process at least one of spend and trend, data related to the prescription drug plan may be retrieved from the database. At least one of spend and trend for the prescription drug plan may be processed using the retrieved data. A determination may be made as to whether at least one option to reduce at least one of spend and trend for the prescription drug plan is available. If an option is available, an indication of the option may be provided to the user computing device. The option may include the change to the prescription drug plan, the impact of which may be simulated by applying the model.

In still another example, an indication may be received from the user computing device of a performance metric for a parameter of the prescription drug plan. A request may be received from the user computing device to process at least one of spend and trend for the prescription drug plan. In response to receiving the request to process at least one of spend and trend, data related to the prescription drug plan may be retrieved from the database. The performance metric for the parameter may be compared to retrieved data related to the parameter. If the retrieved data deviates from the performance metric and if at least one option is available to reduce the deviation, an indication may be provided to the user computing device of an option. The option may include the change to the prescription drug plan, the impact of which may be simulated by applying the model.

In yet another example, a request may be received from the user computing device to process at least one of spend and trend for the prescription drug plan. In response to receiving the request to process at least one of spend and trend, data related to the prescription drug plan may be retrieved from the database. At least one of spend and trend for the prescription drug plan may be processed using the retrieved data. The processing may include determining components of at least one of spend and trend having a significant impact on at least one of spend and trend. If at least one option is available to improve at least one of the components, the user computing device may be provided with an indication of an option. The option may include the change to the prescription drug plan, the impact of which may be simulated by applying the model.

In still another example, a determination may be made as to whether a status change is projected for a particular drug in a marketplace. If at least one option related to the status change for the particular drug is available, an indication of an option may be provided to the user computing device. The option may include the change to the prescription drug plan, which may be simulated by applying the model.

In yet another example, the user computing device may be provided with an indication of a plurality of available models for simulating at least one change to the prescription drug plan. A selection may be received from the user computing device of a particular model of the plurality models for application to the retrieved data.

In yet another example, the at least one change to the prescription drug plan may include a first change and a second change. The first change may have a corresponding first model, and the second change may have a corresponding second model. A request to simulate the first and second changes to the prescription drug plan may be received from the user computing device. The first and second models may be applied to the retrieved data. The first and second models may include a plurality of calculations to simulate the respective first and second changes to the prescription drug plan. The user computing device may be provided with an indication of an impact on the prescription drug plan responsive to the first and second changes based at least in part on the application of the first and second models to the retrieved data.

In still another example, at least one modeling input may be received from the user computing device. The at least one modeling input may indicate a value for at least one parameter of the model. In yet another example, a request may be received from the user computing device to store data related to the impact of the change on the prescription drug plan. The data related to the impact may be communicated to the database for storage. In still another example, the change to the prescription drug plan may be a benefit design change. In such an example, the applied model may be, for example, a formulary options model, a therapeutic class optimizer model, a dose optimization model, a quantity per dispensing event model, a smart rules model, a traditional prior authorization model, a specialty model, a new drug events model, a Medicare coordination of benefits model, or an inclusions/exclusions model (definitions of these benefit design models are provided hereinabove). In yet another example, the change to the prescription drug plan may be a plan design change. In such an example, the applied model may be, for example, a member cost share model, a retail refill allowance model, a home delivery advantage model, a member pay the difference model, a generic bundle model, an out of pocket maximum model, a deductibles model, a patient safety program model, a benefit cap model, or a retail access density model (definitions of these plan design models are provided hereinabove).

In some embodiments of the present invention, a system for simulating at least one change to a prescription drug plan may be provided. The system may include a server in communication with a user computing device and a database. The server may be configured to receive a request to simulate a change to the prescription drug plan from the user computing device. In response to receipt of the request, the server may retrieve data related to the prescription drug plan from the database. The server may apply a model that includes a plurality of calculations to simulate the change to the prescription drug plan to the retrieved data. The server may provide the user computing device with an indication of an impact (e.g., financial impact, member impact) on the prescription drug plan responsive to the change based at least in part on the application of the model to the retrieved data. In one example, the impact on the prescription drug plan may be an impact on gross cost, cost share, plan cost, per-member per-month cost, point of service attrition rate, clinical review rate, clinical review denial rate, total denial rate, number of plan members impacted, or any other suitable factor.

In another example, the server may be further configured to receive a request from the user computing device to process at least one of spend and trend for the prescription drug plan. In response to receipt of the request to process at least one of spend and trend, the server may retrieve data related to the prescription drug plan from the database. The server may process at least one of spend and trend for the prescription drug plan using the retrieved data. The server may determine whether at least one option to reduce at least one of spend and trend for the prescription drug plan is available. If an option is available, the server may provide an indication of the option to the user computing device. The option may include the change to the prescription drug plan, which the server may simulate by applying the model.

In yet another example, the server may be further configured to receive an indication from the user computing device of a performance metric for a parameter of the prescription drug plan. The server may receive a request from the user computing device to process at least one of spend and trend for the prescription drug plan. In response to receipt of the request to process at least one of spend and trend, the server may retrieve data related to the prescription drug plan from the database. The server may compare the performance metric for the parameter to retrieved data related to the parameter.

If the retrieved data deviates from the performance metric and if at least one option is available to reduce the deviation, the server may provide an indication to the user computing device of an option. The option may include the change to the prescription drug plan, which the server may simulate by applying the model.

In still another example, the server may be further configured to receive a request from the user computing device to process at least one of spend and trend for the prescription drug plan. In response to receipt of the request to process at least one of spend and trend, the server may retrieve data related to the prescription drug plan from the database. The server may process at least one of spend and trend for the prescription drug plan using the retrieved data. The server may be further configured to determine components of at least one of spend and trend having a significant impact on at least one of spend and trend. If at least one option is available to improve at least one of the components, the server may provide the user computing device with an indication of an option. The option may include the change to the prescription drug plan, which the server may simulate by applying the model.

In yet another example, the server may be further configured to determine whether a status change is projected for a particular drug in a marketplace. If at least one option related to the status change for the particular drug is available, the server may provide an indication of an option to the user computing device. The option may include the change to the prescription drug plan, which the server may simulate by applying the model.

In still another example, the server may be further configured to provide the user computing device with an indication of a plurality of available models for simulating at least one change to the prescription drug plan. The server may receive a selection from the user computing device of a particular model of the plurality models for application to the retrieved data.

In still another example, the change may include a first change and a second change. The first change may have a corresponding first model, and the second change may have a corresponding second model. The server may be further configured to receive a request to simulate the first and second changes to the prescription drug plan from the user computing device. The server may apply the first and second models to the retrieved data. The first and second models may include a plurality of calculations to simulate the respective first and second changes to the prescription drug plan. The server may provide the user computing device with an indication of an impact on the prescription drug plan responsive to the first and second changes based at least in part on the application of the first and second models to the retrieved data.

In yet another example, the server may be further configured to receive at least one modeling input from the user computing device. The at least one modeling input may indicate a value for at least one parameter of the model. In still another example, the server may be further configured to receive a request from the user computing device to store data related to the impact of the at least one change on the prescription drug plan. The server may communicate the data related to the impact to the database for storage. In yet another example, the change to the prescription drug plan may be a benefit design change. In such an example, the applied model may be, for example, a formulary options model, a therapeutic class optimizer model, a dose optimization model, a quantity per dispensing event model, a smart rules model, a traditional prior authorization model, a specialty model, a new drug events model, a Medicare coordination of benefits model, or an inclusions/exclusions model (definitions of these benefit design models are provided hereinabove). In still another example, the change to the prescription drug plan may be a plan design change. In such an example, the applied model may be, for example, a member cost share model, a retail refill allowance model, a home delivery advantage model, a member pay the difference model, a generic bundle model, an out of pocket maximum model, a deductibles model, a patient safety program model, a benefit cap model, or a retail access density model (definitions of these plan design models are provided hereinabove).

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

Additional embodiments of the invention, its nature and various advantages, will be more apparent upon consideration of the following detailed description, taken in conjunction with the accompanying drawings, in which like reference characters refer to like parts throughout, and in which:

FIG. 27 is an illustrative hierarchy and level selection screen that may be provided by the prescription drug spend and trend application in accordance with some embodiments of the present invention;

FIG. 28 is an illustrative preferences screen that may be provided by the prescription drug spend and trend application in accordance with some embodiments of the present invention;

FIG. 30 is an illustrative performance metrics and alerts screen that may be provided by the prescription drug spend and trend application in accordance with some embodiments of the present invention;

FIG. 34 is an illustrative prescription drug plan defaults screen that may be provided by the prescription drug spend and trend application in accordance with some embodiments of the present invention;

FIGS. 36-38 are illustrative prescription drug plan spend information screens that may be provided by the prescription drug spend and trend application in accordance with some embodiments of the present invention;

FIG. 40 is an illustrative model inputs screen for a prescription drug plan spend option that may be provided by the prescription drug spend and trend application in accordance with some embodiments of the present invention;

FIG. 41 is an illustrative model inputs details overlay for a prescription drug plan spend option that may be provided by the prescription drug spend and trend application in accordance with some embodiments of the present invention;

FIG. 42 is an illustrative model output screen for a prescription drug plan spend option that may be provided by the prescription drug spend and trend application in accordance with some embodiments of the present invention;

FIG. 47 is an illustrative model inputs screen for a prescription drug plan trend option that may be provided by the prescription drug spend and trend application in accordance with some embodiments of the present invention;

FIG. 48 is an illustrative model inputs details overlay for a prescription drug plan trend option that may be provided by the prescription drug spend and trend application in accordance with some embodiments of the present invention;

FIG. 49 is an illustrative model output screen for a prescription drug plan trend option that may be provided by the prescription drug spend and trend application in accordance with some embodiments of the present invention;

FIG. 50 is an illustrative model output solution summary screen for a prescription drug plan trend option that may be provided by the prescription drug spend and trend application in accordance with some embodiments of the present invention;

FIGS. 52A and 52B are portions of an illustrative prescription drug plan model selection and input screen that may be provided by the prescription drug spend and trend application in accordance with some embodiments of the present invention;

FIGS. 55 and 56 are illustrative drug event screens that may be provided by the prescription drug spend and trend application in accordance with some embodiments of the present invention.

DETAILED DESCRIPTION OF THE INVENTION

Figure 1:
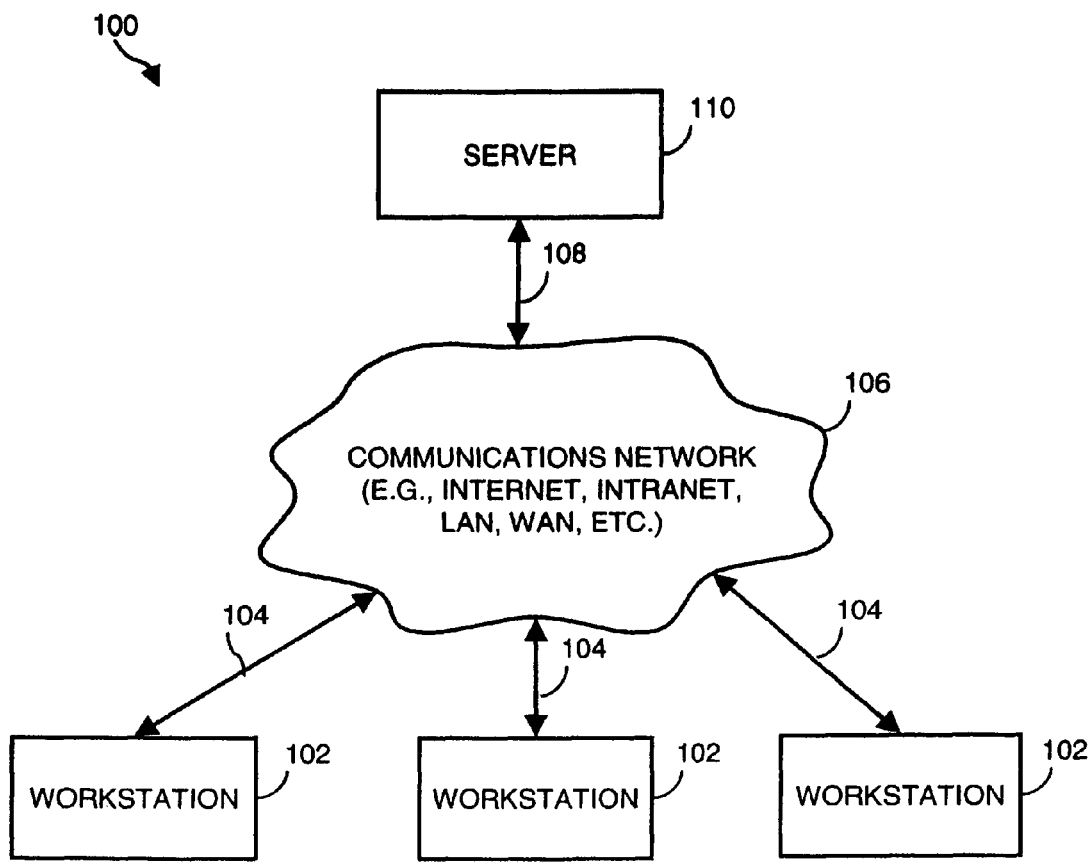
FIG. 1 is a schematic diagram of an illustrative prescription drug plan management system on which a prescription drug spend and trend application may be implemented in accordance with some embodiments of the present invention.

The following description includes many specific details. The inclusion of such details is for the purpose of illustration only and should not be understood to limit the invention. Moreover, certain features which are well known in the art are not described in detail in order to avoid complication of the subject matter of the present invention. In addition, it will be understood that features in one embodiment may be combined with features in other embodiments of the invention.

In accordance with the present invention, systems and methods for computer implemented analysis of spend and/or trend for prescription drug plans are provided (hereinafter "spend and/or trend application" or "spend and trend application"). A prescription drug plan spend and/or trend application may be implemented on the prescription drug plan management system of the present invention. The spend and/or trend application may receive information about an existing prescription drug plan. (It should be noted that the term "prescription drug" as used herein may refer to any product or service provided under the prescription drug plan, including, but not limited to, prescription drugs, non-prescription drugs, medical devices, durable medical equipment ("DME"), and diabetic supplies.) The plan information may include, for example, plan design information, benefit design information, or any other suitable information in connection with the prescription drug plan. The spend and/or trend application may retrieve data in connection with the prescription drug plan, such as claims and membership data. Such data may be stored, for example, in an information warehouse for access by the spend and/or trend application. The spend and/or trend application may use the retrieved data and the plan profile information to analyze spend and/or trend for the prescription drug plan.

In creating a profile for a prescription drug plan, in accordance with at least one embodiment of the invention, one or more performance metrics may be selected (e.g., by a prescription drug plan administrator). Based on the selection of one or more performance metrics, the spend and/or trend application may provide a performance alert if the spend and trend analysis indicates a deviation from the desired metric. In other words, if a certain plan parameter falls below or rises above some specified value (e.g., the selected performance metric), then the spend and trend application optionally provides an alert or other indication to indicate this deviation.

As described hereinabove, the prescription drug plan management system and optional architecture for same implements computerized methods for analyzing spend and/or trend for a prescription drug plan. In connection with this spend and trend analysis, the spend and trend application may determine, for example, the primary components of spend and trend for a prescription drug plan. For example, the application may determine which components of spend and trend have the greatest impact on a plan's overall spend and trend. These components reflect areas in which the plan could be improved to result in a reduction of spend and trend.

Based on an analysis of spend and trend, the spend and trend application may, in at least one embodiment, optionally determine that an option is available to reduce spend and trend for a prescription drug plan. For example, an option may be provided that addresses one of the primary components of spend and trend as determined by the spend and trend application. In another example, the option may address a deviation from a selected performance metric by the prescription drug plan. The option provided by the spend and trend application may seek to bring the parameter within the bounds initially selected for the performance metric during the set up of the plan profile. In yet another example, the option may address a drug event in the marketplace. Such a drug event may include, for example, the expiration of a patent for a drug, the introduction of a new drug, a market withdrawal of an existing drug, a drug shifting from prescription to over-the-counter, a new indication for a drug, or any other suitable drug event.

The spend and trend application may optionally, in at least one embodiment, provide one or more prescription drug plan models to project the impact of a change to a prescription drug plan (e.g., financial impact, member impact, etc.). For example, based on an analysis of the spend and trend for a prescription drug plan, the spend and trend application may determine that an option to reduce the spend and trend is available. The spend and trend application may optionally provide a prescription drug plan model to project the impact of the implementation of the option on the plan. In another example, the model may be selected from a list of available models by a user of the prescription drug plan management system. The spend and trend application may optionally project the impact of the change set forth by the selected model on the prescription drug plan.

As described hereinabove, the spend and/or trend application of the present invention may analyze spend and/or trend for a prescription drug plan. Based on the analysis, the spend and trend application may, for example, indicate deviations in the plan data from desired plan parameters, determine the primary components of the prescription drug plan's spend and trend, provide options for improving the prescription drug plan, and model the impact of a change to the prescription drug plan. One of ordinary skill would know how to implement the comparisons, calculations, and analysis of the present invention based on the information provided in this application.

Figure 56:
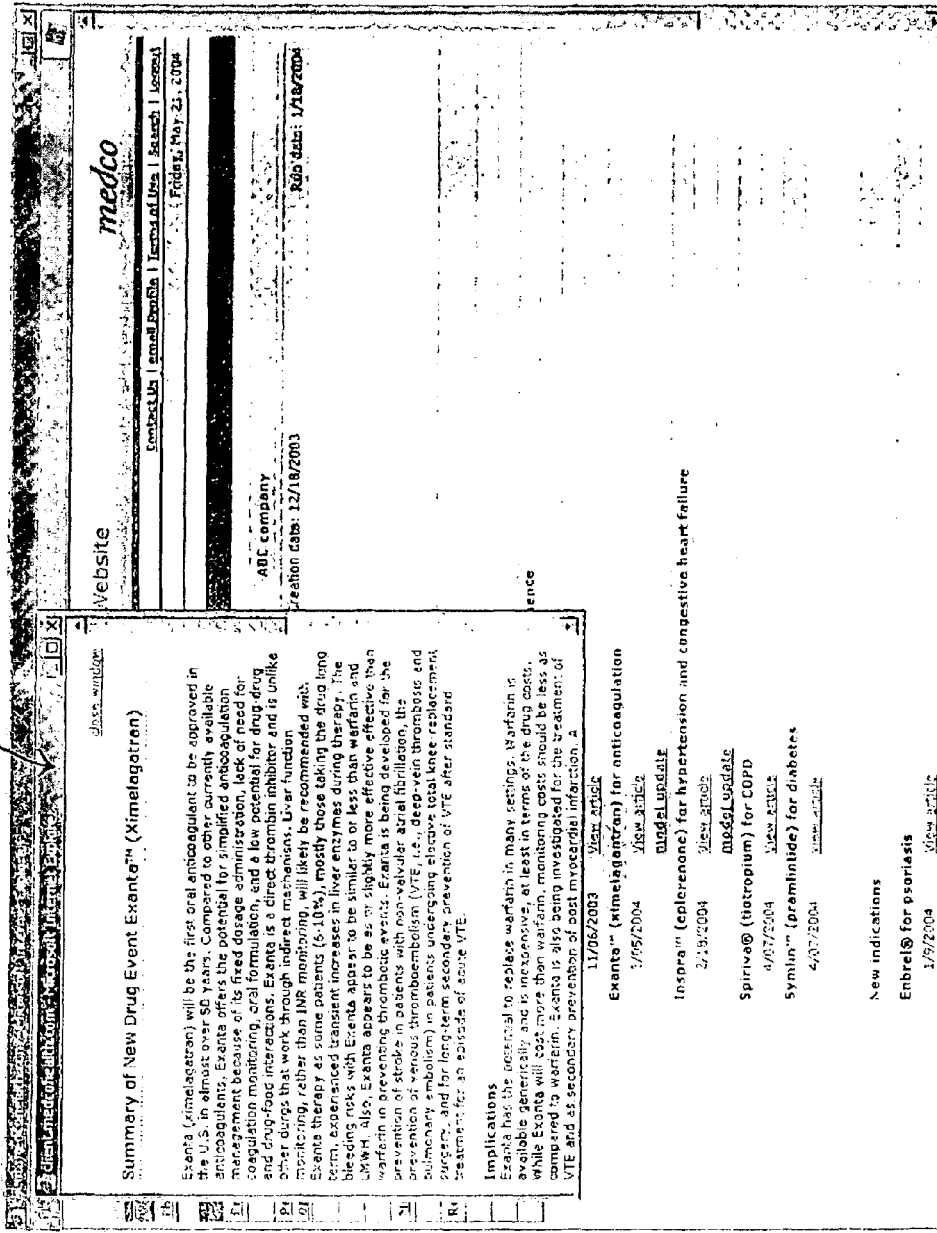

The following FIGS. 1-56 and their accompanying descriptions provide detailed examples of the implementation of the systems and methods of the present invention.

FIG. 1 is a generalized schematic diagram of an illustrative prescription drug plan management system 100 on which a prescription drug spend and trend application may, be implemented in accordance with some embodiments of the present invention. As illustrated, system 100 may include one or more workstations 102. Workstations 102 may be local to each other or remote from each other. Workstations 102 are connected by one or more communications links 104 to a communications network 106 that is linked via a communications link 108 to a server 110.

System 100 may include one or more servers 110. Server 110 may be any suitable server for providing access to the spend and trend application, such as a processor, a computer, a data processing device, or a combination of such devices. Communications network 106 may be any suitable computer network including the Internet, an intranet, a wide-area network ("WAN"), a local-area network ("LAN"), a wireless network, a digital subscriber line ("DSL") network, a frame relay network, an asynchronous transfer mode ("ATM") network, a virtual private network ("VPN"), or any combination of any of such networks. Communications links 104 and 108 may be any communications links suitable for communicating data between workstations 102 and server 110, such as network links, dial-up links, wireless links, hard-wired links, any other suitable communications links, or a combination of such links. Workstations 102 enable a user to access features of the prescription drug spend and trend application. Workstations 102 may be personal computers, laptop computers, mainframe computers, dumb terminals, data displays, Internet browsers, personal digital assistants ("PDAs"), two-way pagers, wireless terminals, portable telephones, any other suitable access device, or any combination of such devices. Workstations 102 and server 110 may be located at any suitable location. In one embodiment, workstations 102 and server 110 may be located within an organization. Alternatively, workstations 102 and server 110 may be distributed between multiple organizations.

Figure 2:
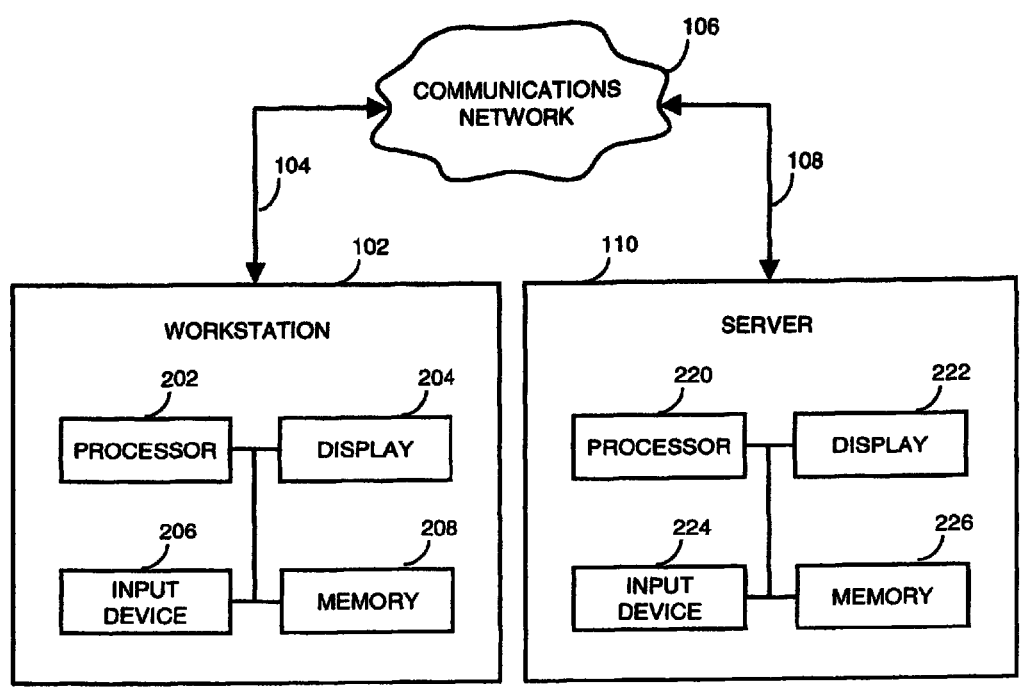
FIG. 2 is a schematic diagram of an illustrative workstation and server as provided, for example, in FIG. 1 in accordance with some embodiments of the present invention.

The server and one of the workstations, which are depicted in FIG. 1, are illustrated in more detail in FIG. 2. Referring to FIG. 2, workstation 102 may include processor 202, display 204, input device 206, and memory 208, which may be interconnected. In a preferred embodiment, memory 208 contains a storage device for storing a workstation program for controlling processor 202.

Processor 202 uses the workstation program to present on display 204 the application and the data received through communications link 104 and commands and values transmitted by a user of workstation 102. It should also be noted that data received through communications link 104 or any other communications links may be received from any suitable source, such as WebServices. Input device 206 may be a computer keyboard, a cursor-controller, dial, switchbank, lever, or any other suitable input device as would be used by a designer of input systems or process control systems.

Server 110 may include processor 220, display 222, input device 224, and memory 226, which may be interconnected. In a preferred embodiment, memory 226 contains a storage device for storing data received through communications link 108 or through other links, and also receives commands and values transmitted by one or more users. The storage device further contains a server program for controlling processor 220.

In some embodiments, the spend and trend application may include an application program interface (not shown), or alternatively, the application may be resident in the memory of workstation 102 or server 110. In another suitable embodiment, the only distribution to workstation 102 may be a graphical user interface ("GUI") which allows a user to interact with the spend and trend application resident at, for example, server 110.

In one particular embodiment, the spend and trend application may include client-side software, hardware, or both. For example, the application may encompass one or more Web-pages or Web-page portions (e.g., via any suitable encoding, such as HyperText Markup Language ("HTML"), Dynamic HyperText Markup Language ("DHTML"), Extensible Markup Language ("XML"), JavaServer Pages ("JSP"), Active Server Pages ("ASP"), Cold Fusion, or any other suitable approaches).

Although the spend and trend application is described herein as being implemented on a workstation and/or server, this is only illustrative. The application may be implemented on any suitable platform (e.g., a personal computer ("PC"), a mainframe computer, a dumb terminal, a data display, a two-way pager, a wireless terminal, a portable telephone, a portable computer, a palmtop computer, an H/PC, an automobile PC, a laptop computer, a personal digital assistant ("PDA"), a combined cellular phone and PDA, etc.) to provide such features.

It will also be understood that the detailed description herein may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

The system according to the invention may include a general purpose computer, or a specially programmed special purpose computer. The user may interact with the system via e.g., a personal computer or over PDA, e.g., the Internet, an Intranet, etc. Either of these may be implemented as a distributed computer system rather than a single computer. Similarly, the communications link may be a dedicated link, a modem over a POTS line, the Internet and/or any other method of communicating between computers and/or users. Moreover, the processing could be controlled by a software program on one or more computer systems or processors, or could even be partially or wholly implemented in hardware.

Although a single computer may be used, the system according to one or more embodiments of the invention is optionally suitably equipped with a multitude or combination of processors or storage devices. For example, the computer may be replaced by, or combined with, any suitable processing system operative in accordance with the concepts of embodiments of the present invention, including sophisticated calculators, hand held, laptop/notebook, mini, mainframe and super computers, as well as processing system network combinations of the same. Further, portions of the system may be provided in any appropriate electronic format, including, for example, provided over a communication line as electronic signals, provided on CD and/or DVD, provided on optical disk memory, etc.

Any presently available or future developed computer software language and/or hardware components can be employed in such embodiments of the present invention. For example, at least some of the functionality mentioned above could be implemented using Visual Basic, C, C++ or any assembly language appropriate in view of the processor being used. It could also be written in an object oriented and/or interpretive environment such as Java and transported to multiple destinations to various users.

Figure 3:
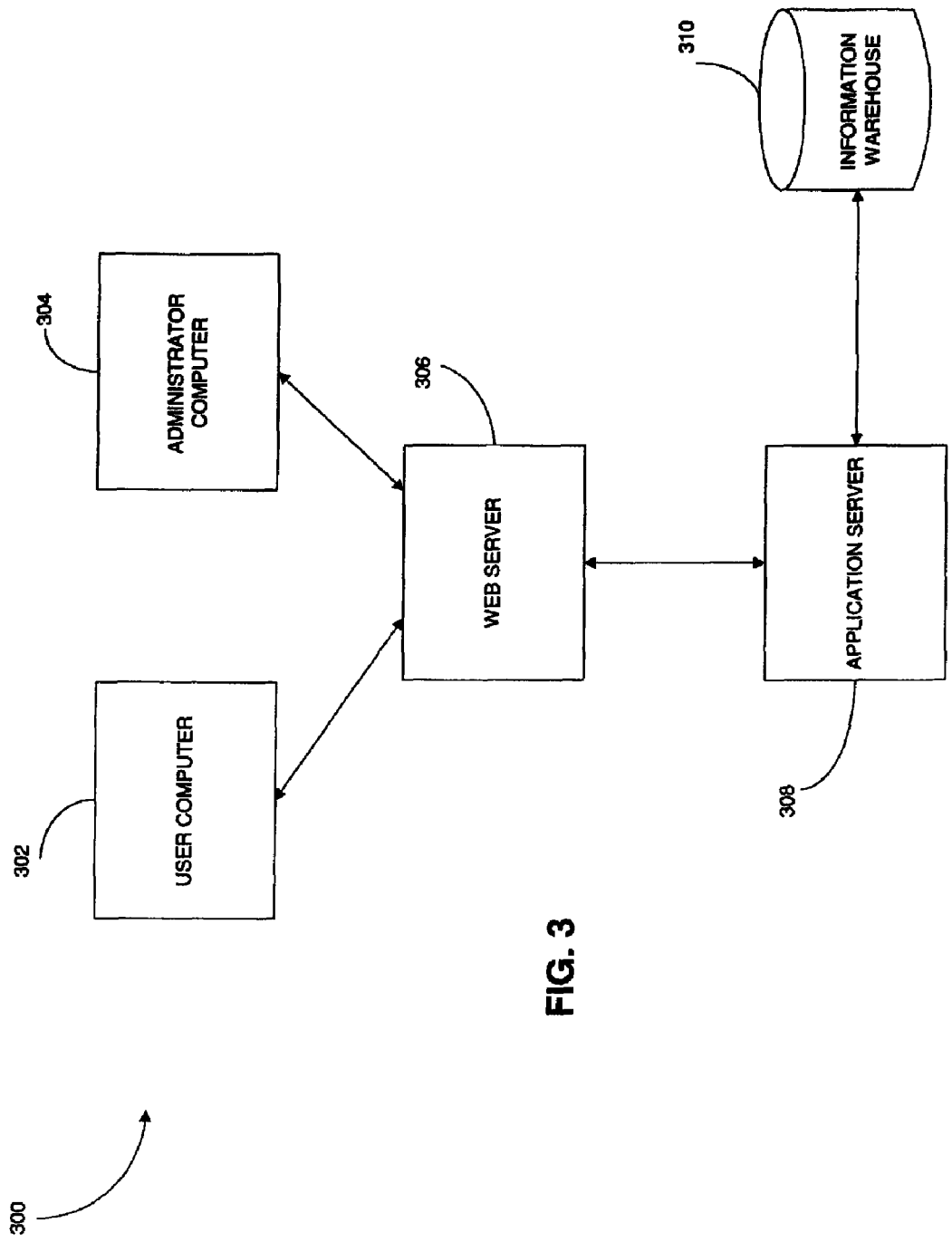
FIG. 3 is another schematic diagram of an illustrative prescription drug plan management system on which a prescription drug spend and trend application may be implemented in accordance with some embodiments of the present invention.

FIG. 3 is a schematic diagram of an illustrative prescription drug plan management system 300 on which a prescription drug spend and trend application may be implemented in accordance with at least one of the embodiments of the present invention. Other standard computer systems may optionally be used. While system 100 of FIG. 1 is a generalized diagram of a management system, system 300 of FIG. 3 provides a more particular example of a management system in accordance with some embodiments of the present invention.

In some embodiments of the present invention, and as shown in FIG. 3, workstations 102 (FIG. 1) may include user computer 302 and administrator computer 304. User computer 302 and administrator computer 304 enable both a management system user and administrator to access features of the prescription drug spend and trend application. It should be noted that the use of the terms "user" and "administrator" is merely to demonstrate that certain parties may be provided with a greater degree of access to the spend and trend application. Alternatively, all users of system 300 may be provided with the same degree of access to the spend and trend application.

In some embodiments of the present invention, and as shown in FIG. 3, server 110 (FIG. 1) may include a web server 306 and an application server 308. Web server 306 may communicate with user computer 302 and administrator computer 304 using any suitable communications scheme (e.g., communications links 104 and 108 and communications network 106 of FIG. 1). Web server 306 may act as a request router between user and administrator computers 302 and 304 and application server 308. Web server 306 may be any suitable web server such as, for example, an iPlanet web server. Application server 308 may receive requests to access features of the spend and trend application as routed by web server 306. Application server 308 may be any suitable application server such as, for example, a BroadVision application server.

As shown in FIG. 3, system 300 may include an information warehouse 310 in communication with application server 308. This arrangement is merely illustrative, and information warehouse 310 may alternatively be in direct communication with web server 306 or either of user and administrator computers 302 and 304. Information warehouse 310 may communicate with application server 308 using any suitable communications scheme (e.g., communications network 106 of FIG. 1). Information warehouse 310 stores data such as prescription drug plan claims data, membership data, and any other suitable data related to prescription drug plan management for use by the spend and trend application. (The nature of the information stored in information warehouse 310 will be described in more detail hereinbelow.)

Thus, as shown in FIG. 3, management system 300 may include three tiers of hardware in communication with one another: a front end including user computer 302 and administrator computer 304; an application services tier including web server 306 and application server 308; and an information warehouse tier including information warehouse 310. Each of these tiers includes suitable software to facilitate communication and distribution of data and requests between the various hardware elements. Such software applications are shown, for example, in FIG. 4.

Figure 4:
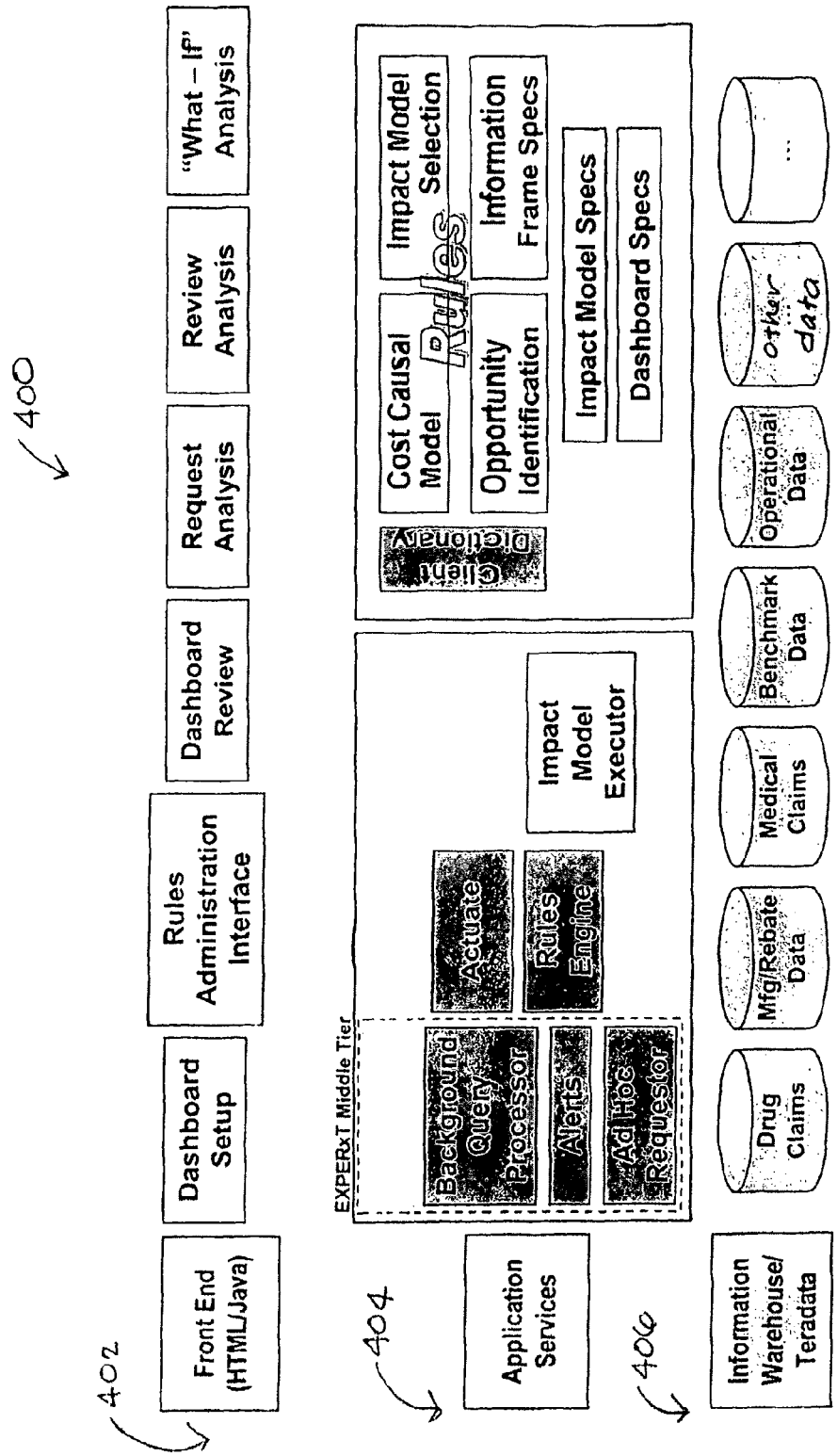
FIG. 4 is yet another schematic diagram of an illustrative prescription drug plan management system on which a prescription drug spend and trend application may be implemented in accordance with some embodiments of the present invention.

FIG. 4 is a schematic diagram of a prescription drug plan management system 400 illustrating software that may be implemented on, for example, the hardware illustrated in FIG. 3 in accordance with some embodiments of the present invention. System 400 may include three tiers of software corresponding to the three hardware tiers shown in FIG. 3: front end 402, application services tier 404, and information warehouse tier 406. Front end 402 may include some or all of the following processes: dashboard setup, rules administration interface, dashboard review, request analysis, review analysis, and "what if" analysis. Application services tier 404 includes the spend and trend application of the present invention. The spend and trend application may include some or all of the following features and/or components: background query processor, alerts, ad hoc requestor, actuate, rules engine, impact model executor, client dictionary, cost causal model, impact model selection, opportunity identification, information frame specifications, impact model specifications, and dashboard specifications. Information warehouse tier 406 includes data accessed by application services tier 404 for implementation of the features of the spend and trend application (e.g., analysis of spend and trend for a prescription drug plan). Information warehouse tier 406 includes some or all of the following data: drug claims data, manufacturer or rebate data, medical claims data, benchmark data, operational data, or any other suitable data.

Figure 5:
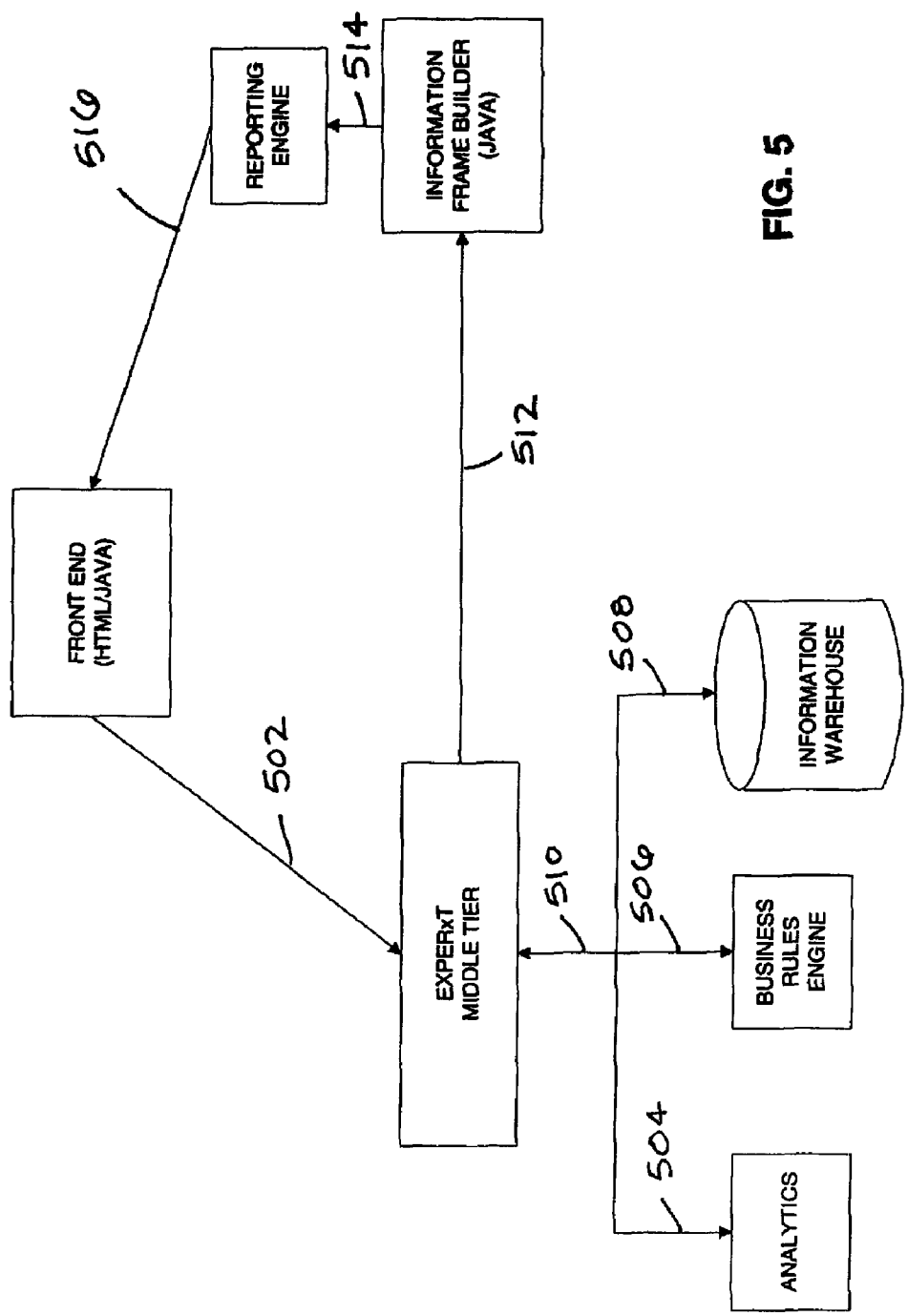
FIG. 5 is an illustrative flow diagram that demonstrates the transmission of data throughout an illustrative prescription drug plan management system in accordance with some embodiments of the present invention.

FIG. 5 is a flow diagram demonstrating in general the transmission of data between at least a portion of the processes and/or components shown in FIG. 4 in accordance with some embodiments of the present invention. As shown, in step 502, the front end (e.g., front end 402 of FIG. 4) may request access to one or more features of the spend and trend application of the present invention. This request may be routed by a web server (e.g., web server 306 of FIG. 3) and transmitted to an application server (e.g., application server 308 of FIG. 3). The middle tier, or application services tier (e.g., application services tier 404 of FIG. 4), may receive the request. In connection with processing the request and formulating a response, the trend and spend application may communicate with some or all of analytics, business rules engine (e.g., Haley rules engine), and information warehouse (steps 504, 506, and 508, respectively). The analytics and business rules engine may include instructions for generating options and implementing models to improve a prescription drug plan. The information warehouse, as described hereinabove in connection with FIG. 4, may include data for the application to use when analyzing spend and trend for a prescription drug plan.

At step 510, data may be communicated from some or all of the analytics, business rules engine, and information warehouse to the middle tier. At step 512, the middle tier transmits this data along to an information frame builder to generate instructions for the presentation of the information on a workstation (e.g., user computer 302 or administrator computer 304 of FIG. 3). At step 514, the instructions generated by the information frame builder are transmitted to a reporting engine for presentation of the screens to the front end. At step 516, the frames are transmitted from the reporting engine to the front end for presentation to a user or administrator.

Figure 6:
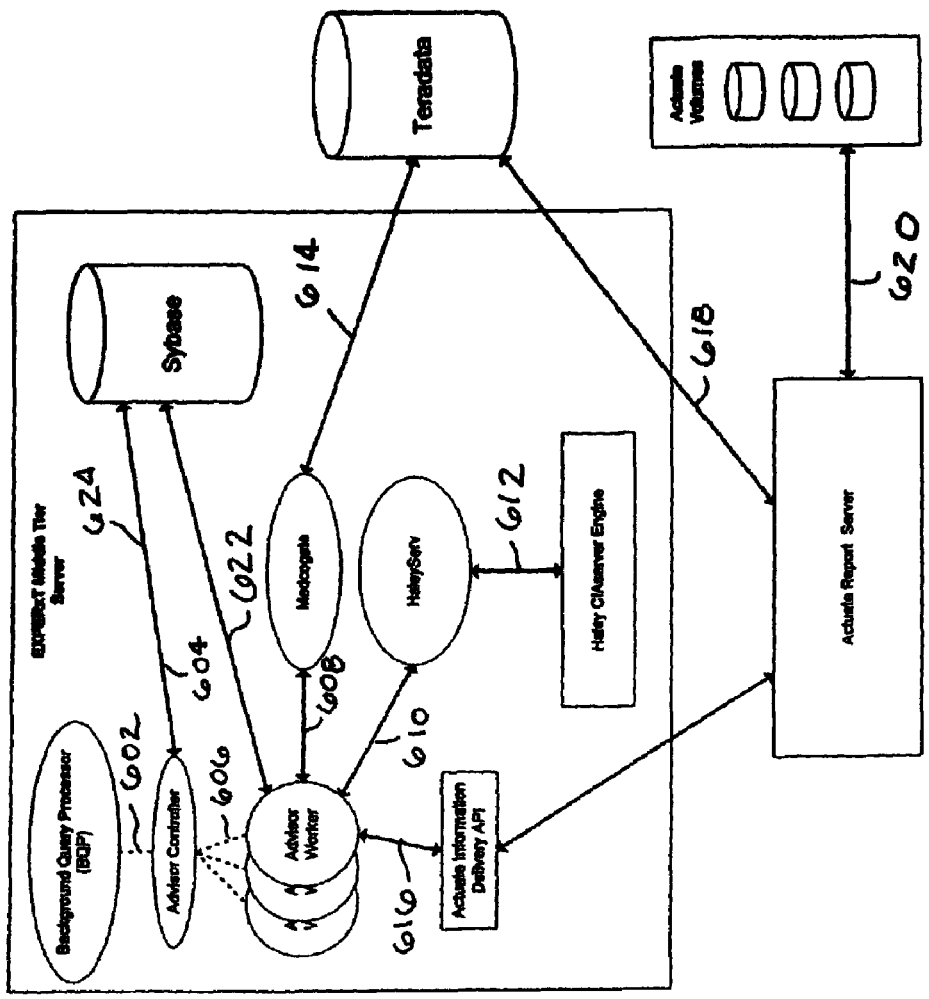
FIG. 6 is an illustrative flow diagram that demonstrates the transmission of data within the middle tier of the prescription drug plan management system of FIG. 5 and between the middle tier and other system elements in accordance with some embodiments of the present invention.

As described hereinabove, FIG. 5 demonstrates the transmission of data throughout an illustrative prescription drug plan management system. In connection with the transmission of data within the middle tier of the system and between the middle tier and the information warehouse tier, FIG. 6 provides an illustrative example. At step 602, on a periodic basis (e.g., monthly, quarterly, etc.), a background query processor ("BQP") for the spend and trend application may spawn a new advisor controller process. The advisor controller process, at step 604, may retrieve profile setup metadata from a database (e.g., a Sybase database). At step 606, the advisor controller process may spawn one or more advisor worker processes. In spawning the advisor worker processes, the advisor controller process may transmit applicable metadata as received from the database to respective advisor work processes.

At step 608, each advisor worker process may generate any necessary queries (e.g., SQL queries) and transmit the query to an information warehouse via an openserver (e.g., the Medcogate Openserver). If an advisor worker process needs to invoke the business rules engine, then at step 610 a request (e.g., an XML request) may be generated using the metadata retrieved from the database. The generated request may be passed along to the business rules engine at step 612, with the output of the request passed back to the applicable advisor worker process. (It should be noted that while the business rules engine shown in the example of FIG. 6 is a standard Haley Systems CIA Server rules engine, this is merely illustrative, and the prescription drug plan management system of the present invention may include any suitable business rules engine.)

At step 614, the advisor worker process may use a database table from the Teradata warehouse to communicate rules output and report data to the actuate reporting system. The actuate information delivery API may be used at step 616 to issue a request (e.g., a simple object access protocol ("SOAP") request) to the actuate report server to generate the report output. Upon receiving the request, the actuate report server may retrieve the applicable data from the Teradata warehouse at step 618, and create a report file at step 620. At step 622, the advisor worker process inserts a results row in the database. At step 624, the advisor worker process terminates and control is passed back to the advisor controller process. Once all advisor worker processes are complete for a given advisor controller process, the BQP updates the database to indicate that the advisor controller run has completed.

Figure 7:
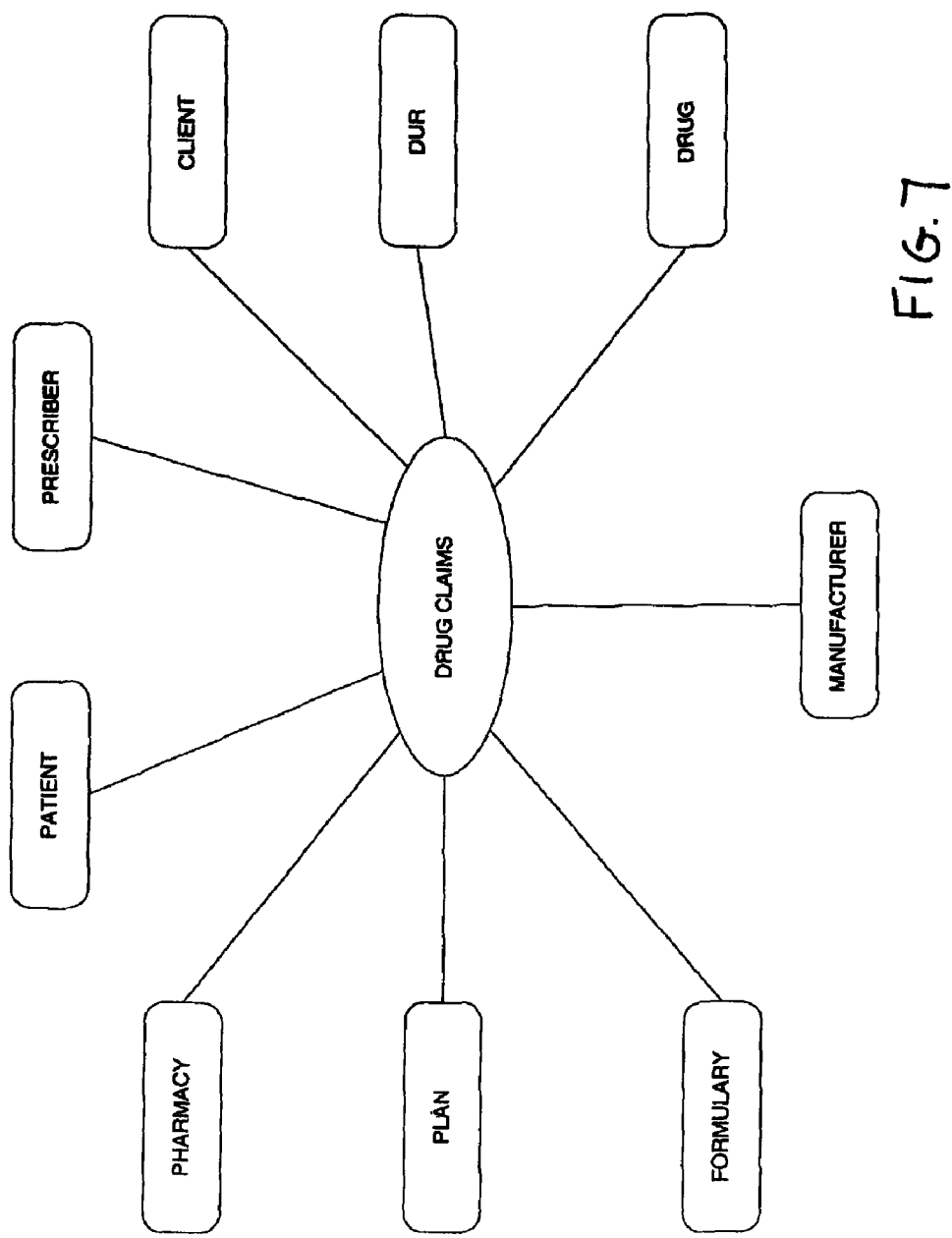
FIG. 7 is a schematic diagram that shows domains of data that may be included in an illustrative drug claim in accordance with some embodiments of the present invention.

As described hereinabove in connection with FIG. 4, information warehouse 406 may include various types of data. One particular type of data that may be stored in information warehouse 406 is drug claim data. FIG. 7 is a schematic diagram that shows domains of data that may be included in an illustrative drug claim in accordance with some embodiments of the present invention. As shown, for example, a drug claim may include data related to or from some or all of the following sources: patient, prescriber, client, drug utilization review ("DUR"), drug, manufacturer, formulary, plan, and pharmacy. This drug claim data may be retrieved by the spend and trend application in connection with analyzing the spend and trend for a particular prescription drug plan. It should be noted that the domains of drug claim data provided herein are merely illustrative, and drug claim data may include any suitable data related to submission or approval of a patient's drug claim.

Figure 8:
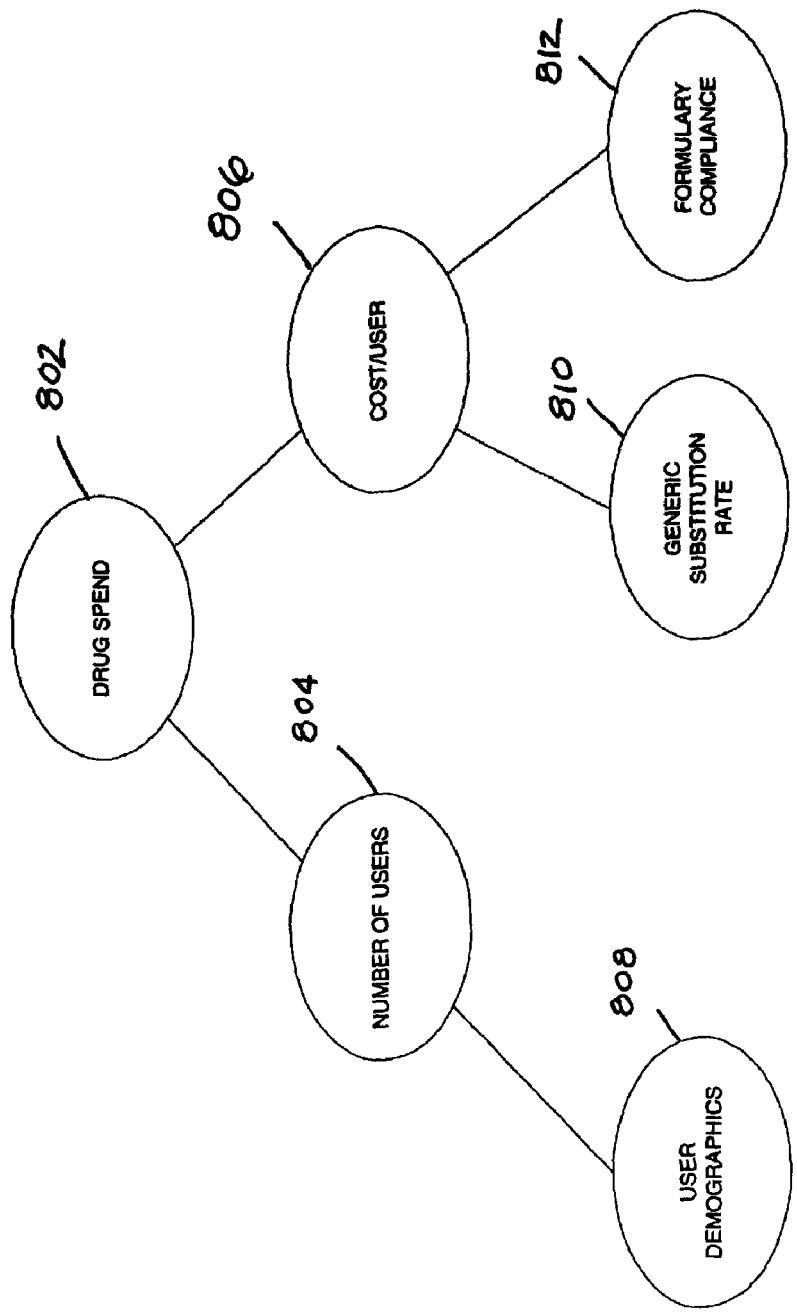
FIG. 8 is a schematic diagram of an illustrative causal data model in connection with performing spend analysis for a prescription drug plan in accordance with some embodiments of the present invention.

As shown in FIG. 7, the drug claim data stored in the information warehouse of the present invention may include various domains of data. The drug claim data and other data stored in the information warehouse (e.g., manufacturer or rebate data, medical claims data, benchmark data, operational data), along with drug plan profile information, may be used to analyze prescription drug plan spend and trend. A feature of the present invention is the ability to analyze spend and trend and determine the primary components for prescription drug spending under a particular plan. FIG. 8 is a schematic diagram of an illustrative causal data model in connection with performing a spend analysis for a prescription drug plan in accordance with some embodiments of the present invention. As shown in the example of FIG. 8, drug spend data 802 is at the top of the data model. Drug spend data 802 may be broken down into components such as the number of users 804 on the prescription drug plan, and the cost per user 806. Number of users 804 may be further broken down into user demographic data 808, demonstrating what types of users make up the prescription drug plan for a particular employer. Such demographics may include, for example, geographic information, sex, age, or any other suitable demographic information. Cost per user 806 may be further broken down into generic substitution rate 810 and formulary compliance 812. The components of drug spend 802 shown in FIG. 8 are merely illustrative, and any suitable components of the drug spend may be provided in a causal data model.

Systems and methods of the present invention may be used to set up a dashboard for a prescription drug plan client. A client dashboard is an interface that may be presented to a user of the prescription drug plan management system to advantageously provide information in connection with a client's prescription drug plan. Such information presented by the client dashboard may include, for example, an analysis of the spend and/or trend for the drug plan, the primary components of spend and/or trend, whether the drug plan has deviated from selected boundaries or parameters, options for improving the plan's spend and trend, and models to project the financial impact of a change to the plan. To set up a dashboard, a plan administrator may input information related to the client's prescription drug plan as requested by the spend and trend application. (As used herein, "client" may refer to an employer who has a prescription drug plan for use by its employees, and "plan administrator" may refer to a user of the spend and trend application who manages the client's prescription drug plan. It should be noted, however, that a client may optionally and advantageously manage its own prescription drug plan without the assistance of the plan administrator.)

Figure 9:
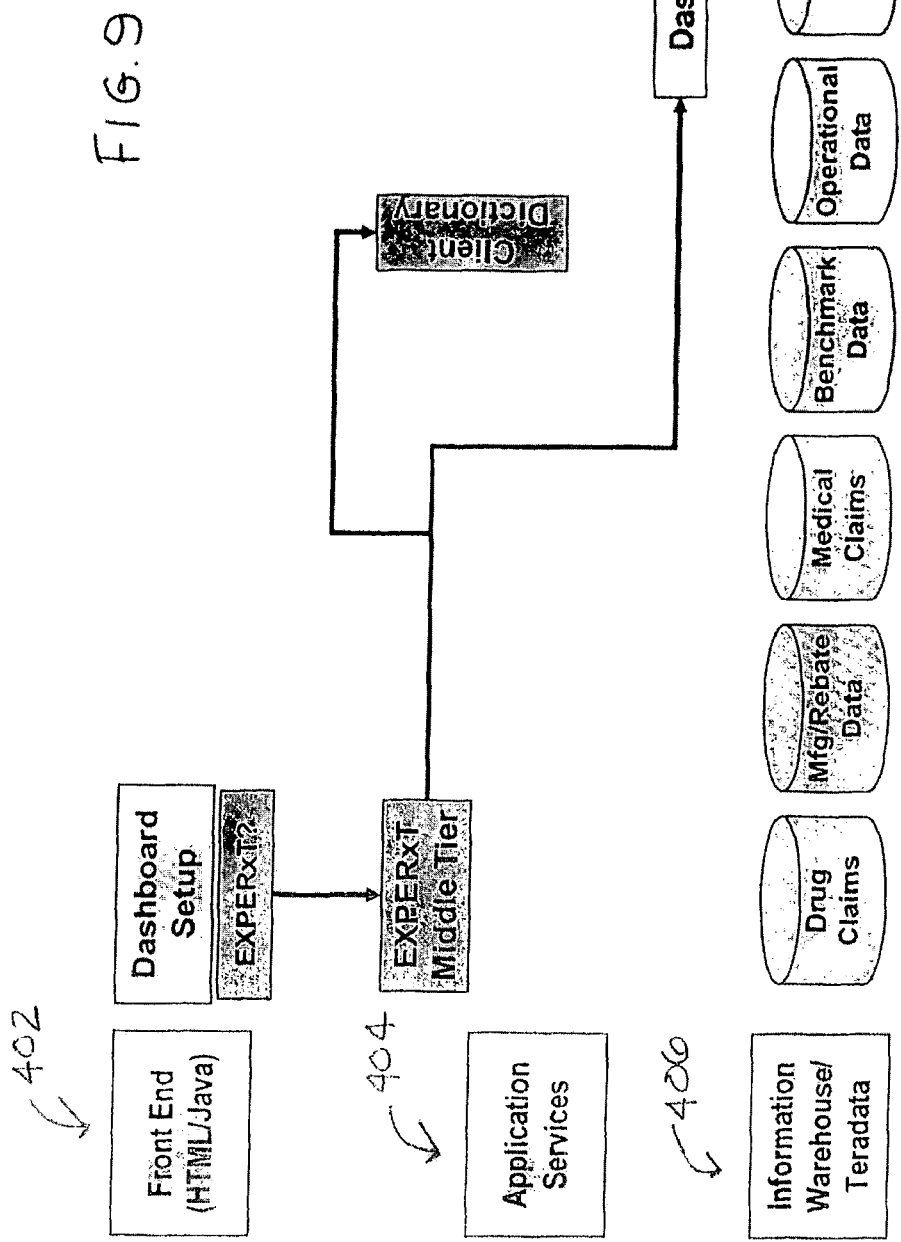
FIG. 9 is an illustrative flow diagram that demonstrates a method for setting up a client dashboard in a prescription drug plan management system in accordance with some embodiments of the present invention.

FIG. 9 is an illustrative flow diagram that demonstrates a method for setting up a client dashboard in accordance with some embodiments of the present invention. As shown in FIG. 9, various processes and/or components shown in FIG. 4 may be utilized to set up a client dashboard. However, this example is merely illustrative, and some, all, or alternative processes and/or components from those shown in FIG. 4 may be used to set up a client dashboard in accordance with the present invention. To set up a client dashboard, the dashboard set up process of front end 402 may communicate with the middle tier of application services tier 404. To obtain specifications for the dashboard and specific information on the particular client, the middle tier may access a client dictionary to obtain specific information on the client for whom the dashboard is being set up. The middle tier may access general dashboard specifications to assist in the layout of the client dashboard.

Figure 10:
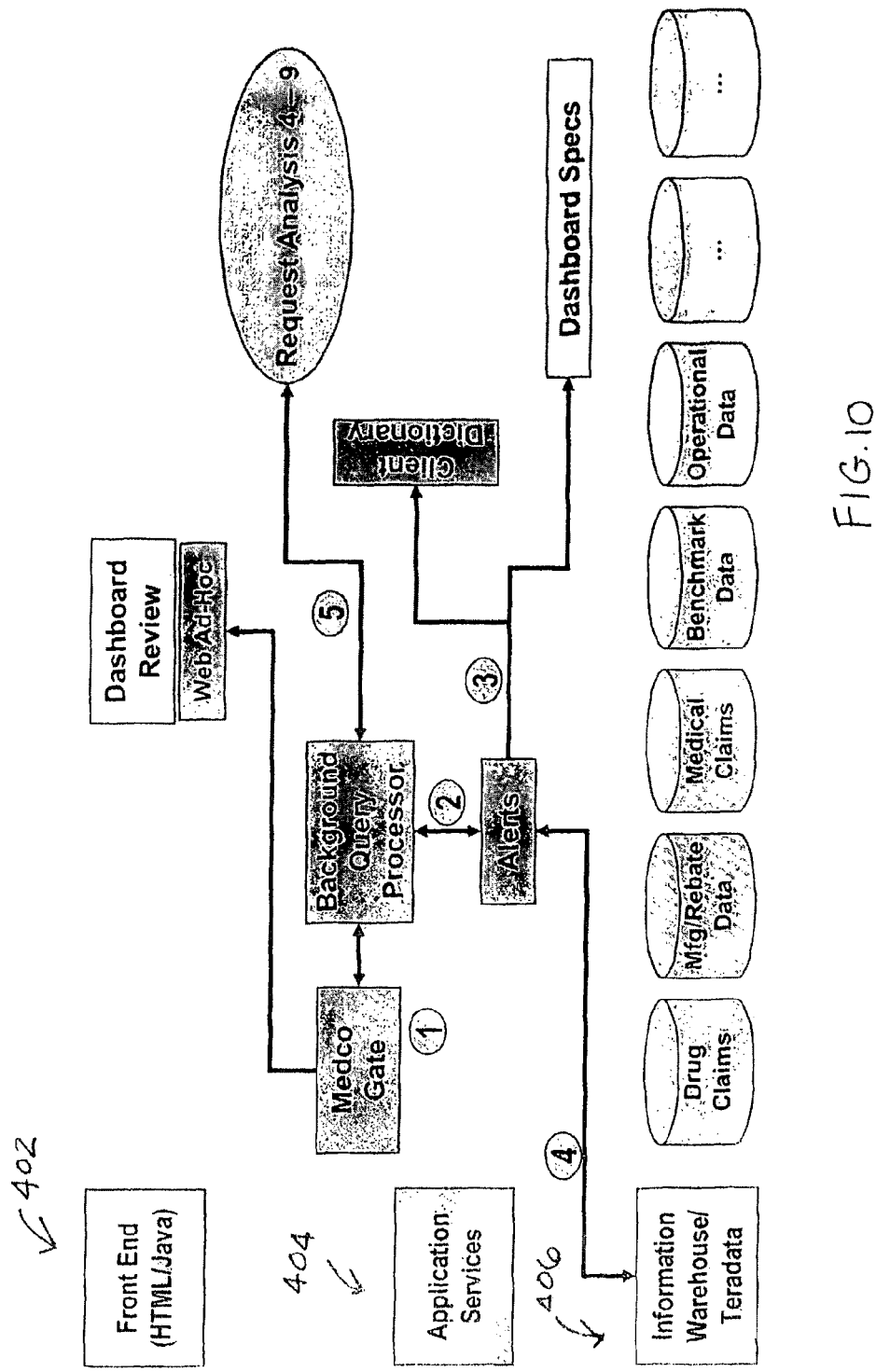
FIG. 10 is an illustrative flow diagram that demonstrates a method for reviewing a client dashboard in a prescription drug plan management system in accordance with some embodiments of the present invention.

FIG. 10 is an illustrative flow diagram that demonstrates a method for reviewing a client dashboard in a prescription drug plan management system in accordance with some embodiments of the present invention. As shown in FIG. 10, various processes and/or components shown in FIG. 4 may be utilized to review a client dashboard. However, this example is merely illustrative, and some, all, or alternative processes and/or components from those shown in FIG. 4 may be used to review a client dashboard in accordance with the present invention. To review a client dashboard, the dashboard review process of front end 402 may communicate with the middle tier of application services tier 404. Front end 402 may access the BQP through a gate process. The BQP may set any alerts requested by a plan administrator by accessing information warehouse tier 406 and the client dictionary and dashboard specifications of application services tier 404. Such alerts may include, for example, an alert based on a performance metric selected by a user of the management system to indicate when a prescription drug plan is not performing satisfactorily. The BQP may control any analysis requests made by a user. For example, the BQP may control an analysis of a prescription drug plan based on application of a prescription drug plan model. (The analysis request is shown in more detail in FIG. 12.)

Figure 11:
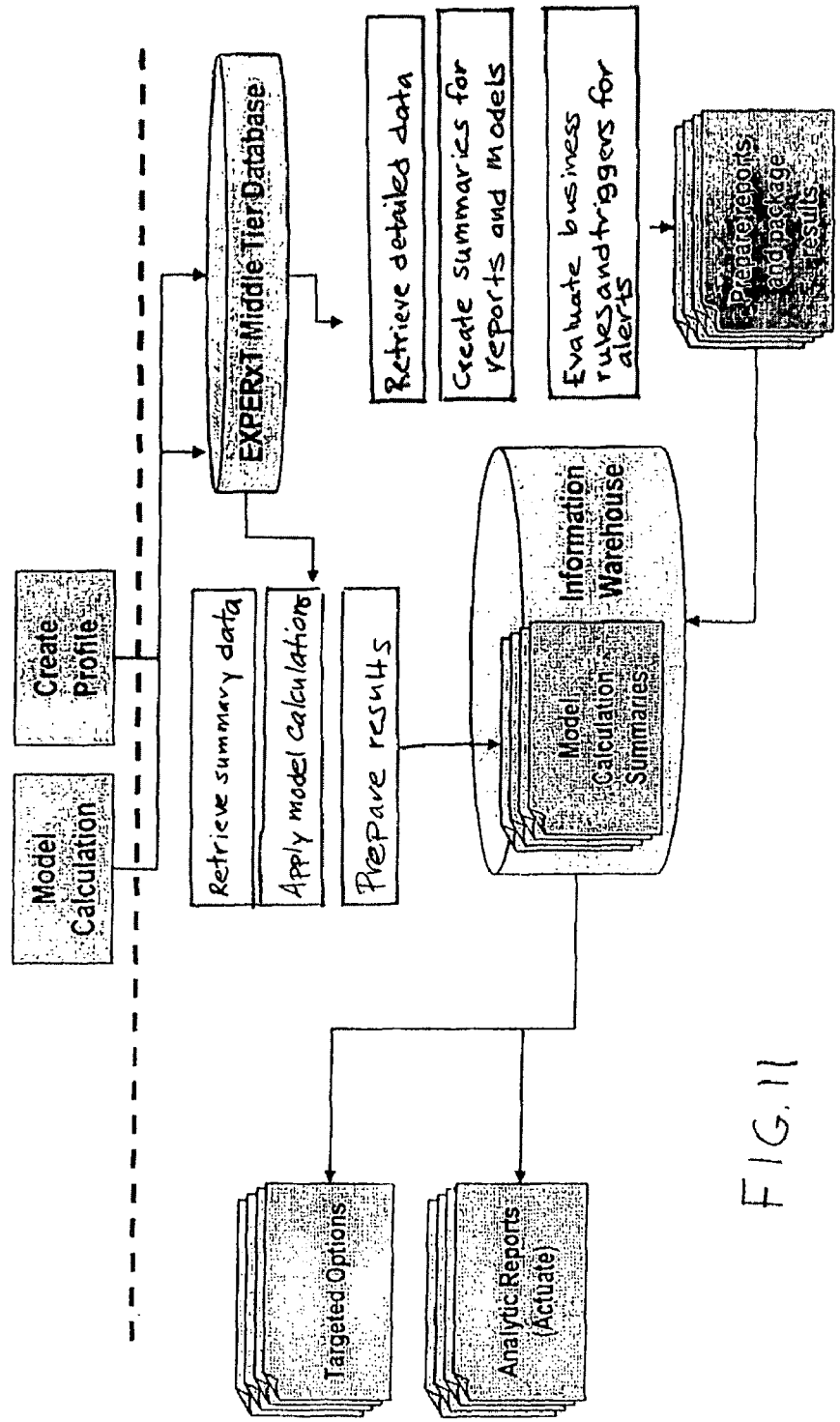
FIG. 11 is an illustrative flow diagram that demonstrates methods for user profile creation and model calculation in a prescription drug plan management system in accordance with some embodiments of the present invention.

As described in connection with FIGS. 9 and 10, the spend and/or trend application of the present invention may set up and review a client dashboard in accordance with some embodiments of the present invention. This may also be referred to herein as a client or user profile. This user profile forms the basis for the analysis of a client's prescription drug plan, such as formulating options for improving the plan and modeling the impact of those options on the plan. FIG. 11 is an illustrative flow diagram that demonstrates a combination of both a method for user profile creation and a method for model calculation in a prescription drug plan management system in accordance with some embodiments of the present invention. In connection with the profile creation process, the spend and/or trend application may access the middle tier database. From the database, the application may retrieve detailed data regarding a client's prescription drug plan, create summaries of the data for use in formulating reports and calculating models, and evaluate business rules and triggers for alerts. The application may then prepare reports and package the results for storage in the information warehouse.

In connection with the model calculation process, the spend and/or trend application may access the middle tier database. From the database, the application may access the reports created during the profile creation process from the information warehouse. Using the data retrieved from the information warehouse, the application may apply a desired model or models to the data. For example, the application may model the financial impact of a particular change to the prescription drug plan. The model may be selected, for example, by a user of the prescription drug plan management system. After the application of the model calculation to the profile data, the application may prepare results and store the results in the information warehouse for subsequent access by the application. The application may, for example, prepare analytic reports based on the model calculation summaries stored in the database. One or both of these options and reports may be provided to the user on, for example, a workstation display (e.g., display 204 of FIG. 2).

Figure 12:
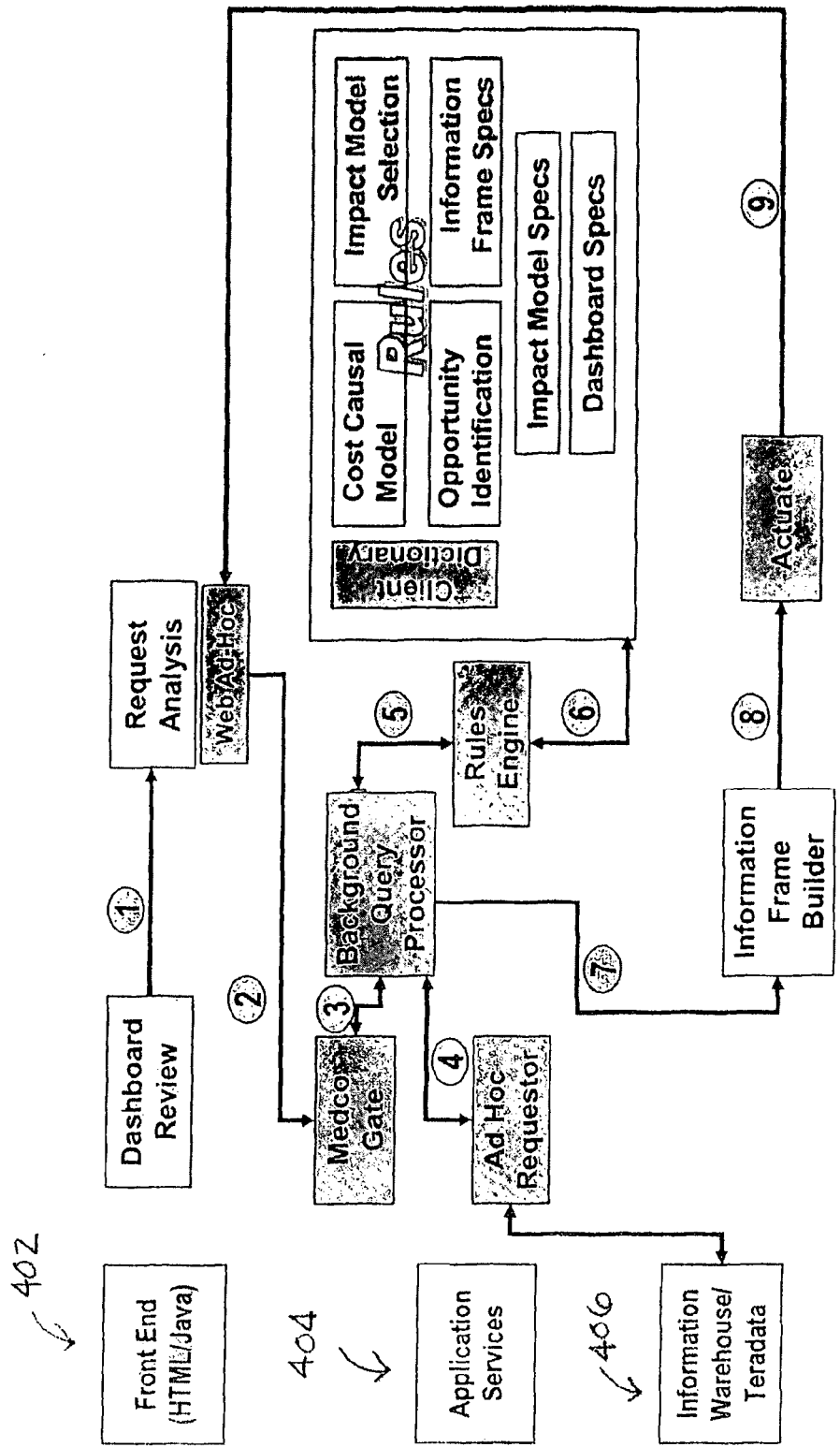
FIG. 12 is an illustrative flow diagram that demonstrates a method for requesting an analysis in a prescription drug plan management system in accordance with some embodiments of the present invention.

FIG. 11 generally demonstrates the creation of a user profile and the calculation of a model in accordance with some embodiments of the present invention. FIG. 12 provides additional detail in connection with a user request for an analysis of spend and trend for a prescription drug plan in accordance with some embodiments of the present invention. As shown in FIG. 12, various processes and/or components shown in FIG. 4 may be utilized to request an analysis of a plan's prescription drug spend and trend. However, this example is merely illustrative, and some, all, or alternative processes and/or components from those shown in FIG. 4 may be used to request an analysis of spend and trend in accordance with the present invention.

As shown in FIG. 12, to analyze spend and/or trend, in at least one embodiment the dashboard review process of front end 402 may communicate with the request analysis process of the front end. The request analysis process may then communicate with the application services tier 404. Front end 402 may access the BQP through a gate process. The BQP may request information from the information warehouse tier 406 from which to base the spend and trend analysis. The BQP may access any necessary rule via a rules engine. For example, based on the nature of the analysis request, the BQP may access some or all of a cost causal model, an impact model selection, an opportunity identification, information frame specifications, impact model specifications, or dashboard specifications. For example, if the request for analysis involves a request to provide options for improving the prescription drug plan, then the rules engine may provide the BQP with access to the opportunity identification aspect of the rules. Based on the application of the rules as facilitated by the business rules engine, the BQP may communicate the results to the information frame builder, which gathers the information in a format suitable for creation of a user interface. The information frame builder further communicates the information to an actuate process, which then provides one or more screens for a user interface to front end 402. Such screen or screens include the results of the request for analysis that originated at front end 402.

Figure 13:
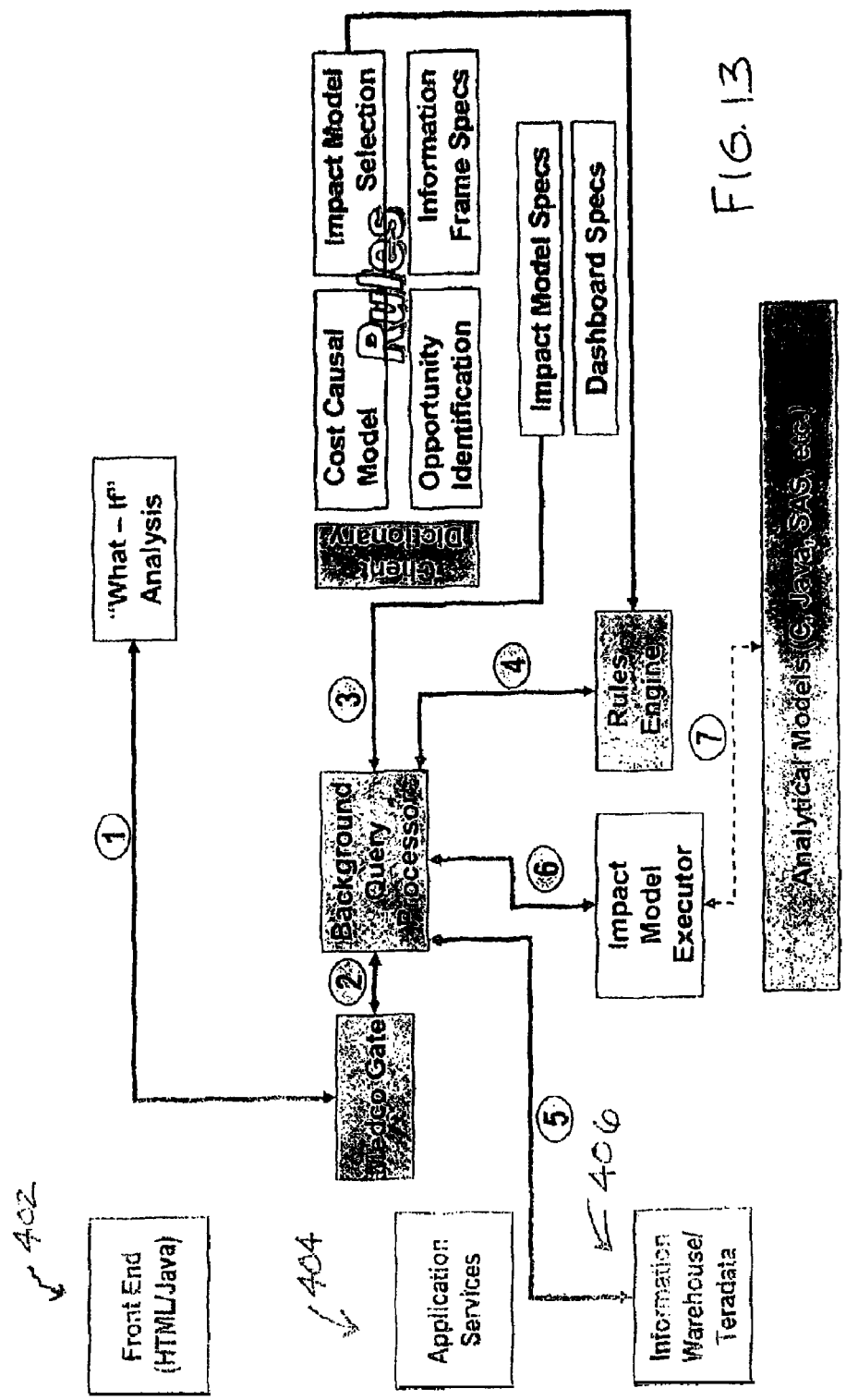
FIG. 13 is an illustrative flow diagram that demonstrates a method for modeling the impact of a prescription drug plan option in a prescription drug plan management system in accordance with some embodiments of the present invention.
Figure 14:
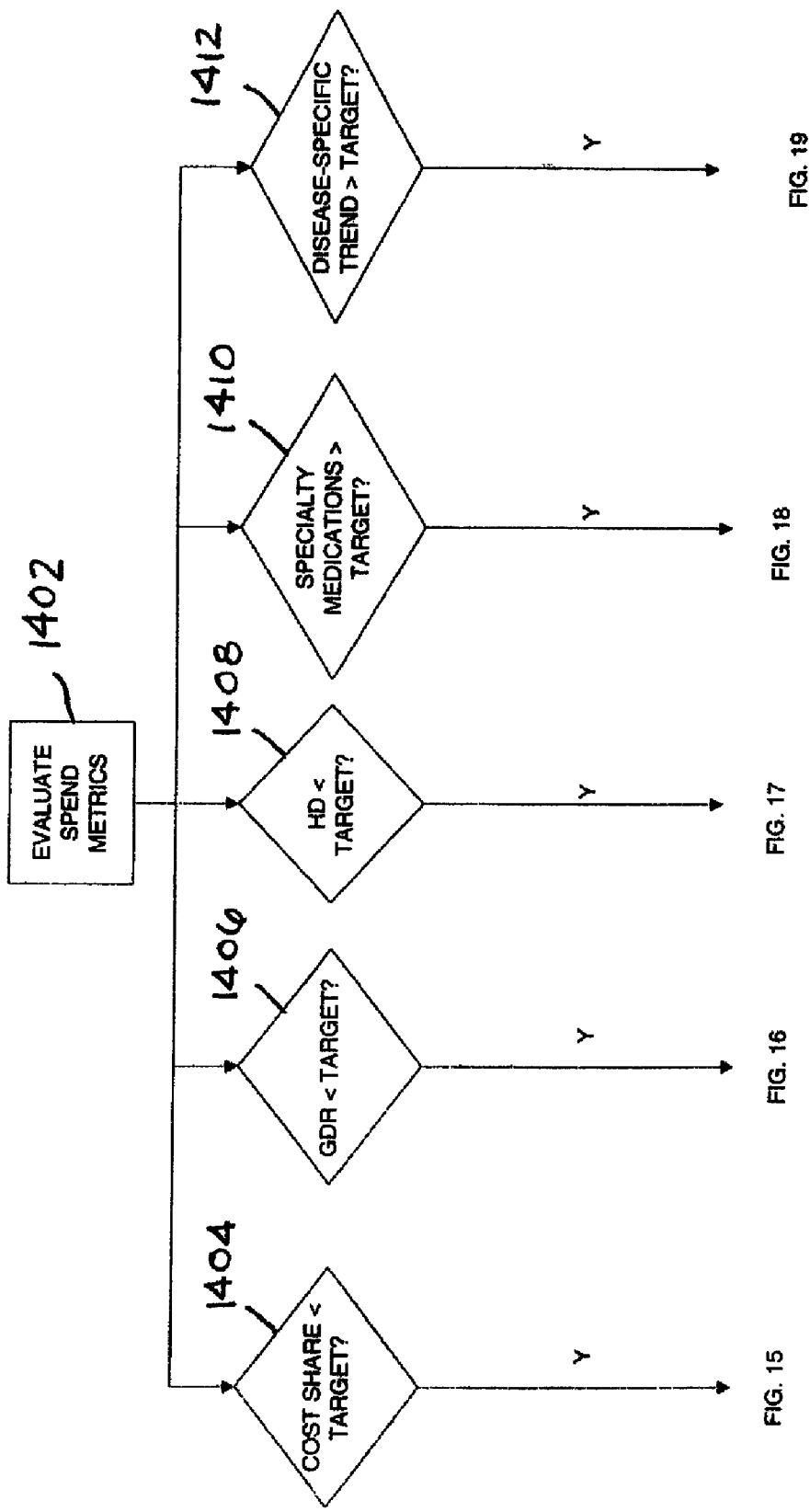
FIGS. 14-19 are illustrative flow diagrams that demonstrate a method for evaluating spend metrics for a prescription drug plan in a prescription drug plan management system in accordance with some embodiments of the present invention.

As described hereinabove, FIG. 12 demonstrates a method for analyzing a client's prescription drug plan in accordance with some embodiments of the present invention. In FIG. 13, an illustrative flow diagram is provided that demonstrates a method for modeling the impact of a prescription drug plan option in a prescription drug plan management system in accordance with some embodiments of the present invention. As shown in FIG. 13, various processes and/or components shown in FIG. 4 may be utilized to apply a model to a prescription drug plan. However, this example is merely illustrative, and some, all, or alternative processes and/or components from those shown in FIG. 4 may be used to apply a model to a prescription drug plan in accordance with the present invention.

As shown in FIG. 13, to model the impact (e.g., financial impact, member impact) of a change to the prescription drug plan, the "what if" analysis process (i.e., "what if" the selected change were applied to the prescription drug plan) of front end 402 may communicate with application services tier 404. In particular, front end 402 may access the BQP through a gate process. The BQP may receive model specifications from an impact model specifications process. The BQP may access an impact model selection process via a business rules engine. The BQP may access the necessary information for performing the modeling analysis from information warehouse tier 406. The combination of the model itself and the information obtained from information warehouse 406 may be communicated to an impact model executor, which uses one or more analytical models (e.g., C, Java, SAS, etc.) to project the impact of a change to the prescription drug plan. As described hereinabove in connection with FIG. 12, the results of the modeling analysis may be communicated to front end 402 for display on a user interface.

The prescription drug spend and trend application, as described hereinabove, may create and review a client dashboard, analyze the spend and/or trend for the client's prescription drug plan, develop options for improving the spend and trend of the plan, and/or model the financial impact of a change on the plan (e.g., model the impact of one of the options generated by the application). In connection with analyzing the spend and trend for the client's prescription drug plan, the spend and trend application may make comparisons between the prescription drug plan data for the client (e.g., as stored in information warehouse 310 of FIG. 3) and selected performance parameters, or metrics. For example, a plan administrator may input a parameter requesting a performance alert whenever the amount of money spent on gastroenterological drugs exceeds a specified value or percentage of overall spend. If analysis of the spend and trend for the prescription drug plan reveals that the actual value spent on the gastroenterological drugs exceeds the specified value or percentage, then the spend and trend application may provide an alert to the administrator. Along with the alert, the spend and trend application may provide an option for reducing the drug spend for the particular deviation. If desired, the application may model the impact of the option on the prescription drug plan.

FIGS. 14-19 are illustrative flow diagrams that demonstrate a method for evaluating spend metrics for a prescription drug plan in a prescription drug plan management system in accordance with some embodiments of the present invention. At step 1402, the spend and trend application may evaluate any applicable prescription drug spend metrics by comparing the actual value for the plan to a target value. These spend metrics may include a target value set by a user (e.g., a plan administrator) or default target values. The examples provided in FIGS. 14-19 are merely illustrative, and the spend and trend application may evaluate some, all, or alternative spend metrics in connection with a client's prescription drug plan.

Figure 15:
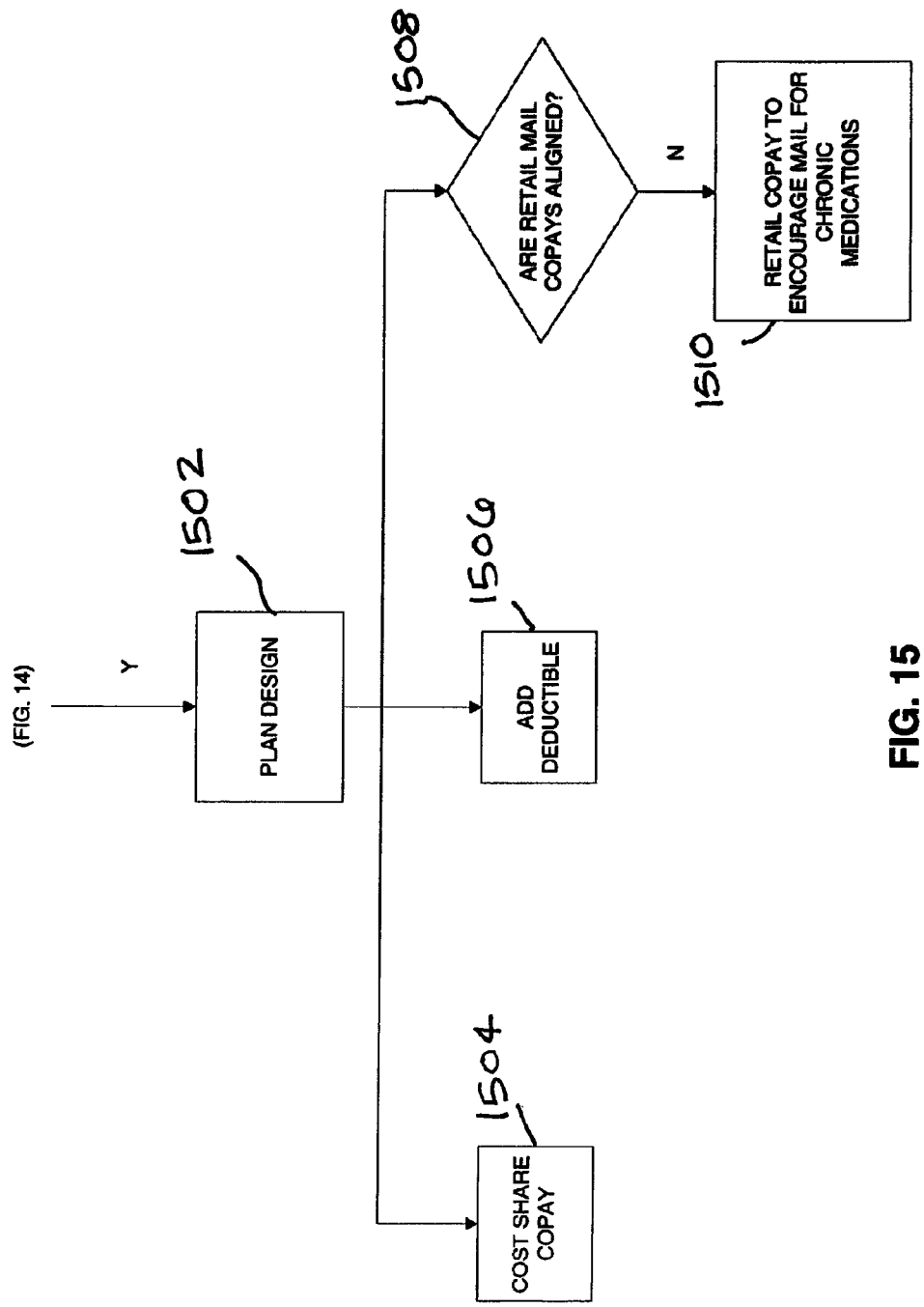

At step 1404, the application evaluates whether a client's cost share for the prescription drug plan is less than a desired target. Cost share, in particular, defines how a pharmacy benefit cost is shared between a member and the plan (e.g., employer). If the cost share is less than the target, then the spend and trend application may proceed to plan design step 1502 (FIG. 15). At step 1502, the application determines whether there are plan design options suitable for increasing the cost share so that it is no longer less than the target value. Such options may include, for example, a cost share co-pay option 1504 or an add deductible option 1506. If retail mail co-pays are not aligned (step 1508), then another option may be to introduce a retail co-pay that encourages the use of mail order for chronic medications (option 1510).

Figure 16:
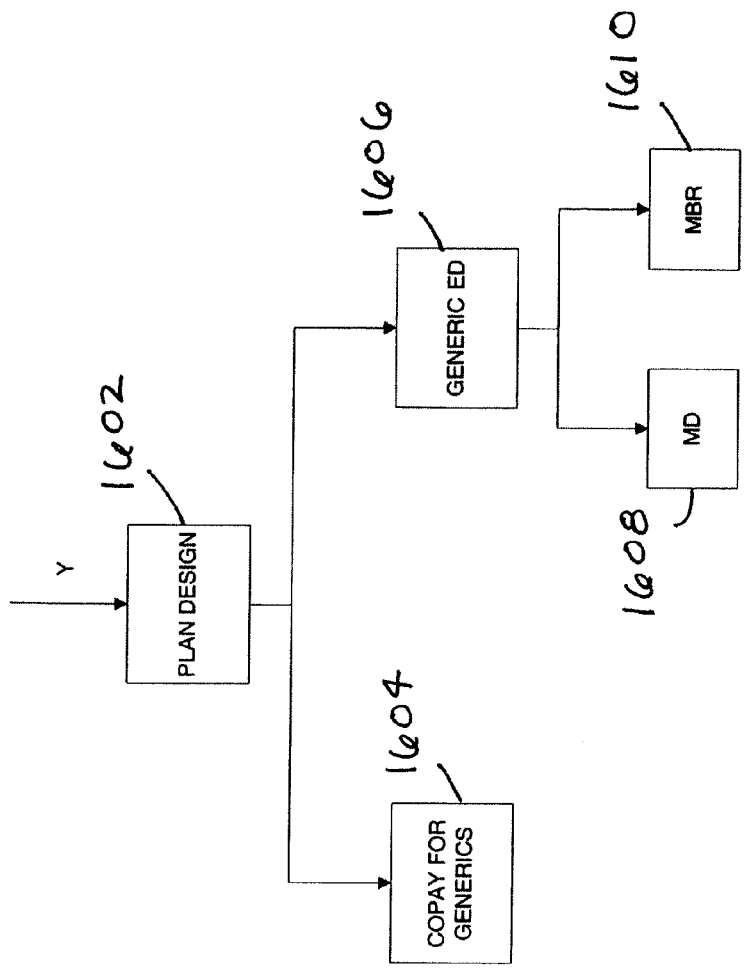

Referring back to FIG. 14, at step 1406, the application evaluates whether a client's generic dispensing rate ("GDR") is less than a desired target. If the GDR is less than the target, then the spend and trend application may proceed to plan design step 1602 (FIG. 16). At step 1602, the application determines whether there are plan design options suitable for increasing the GDR so that it is no longer less than the target value. Such options may include, for example, a decrease in co-pay for generics option 1604 or a generic drug education option 1606. The generic drug education option 1606 may further include an option to educate doctors (option 1608), plan members (option 1610), or both.

Figure 17:
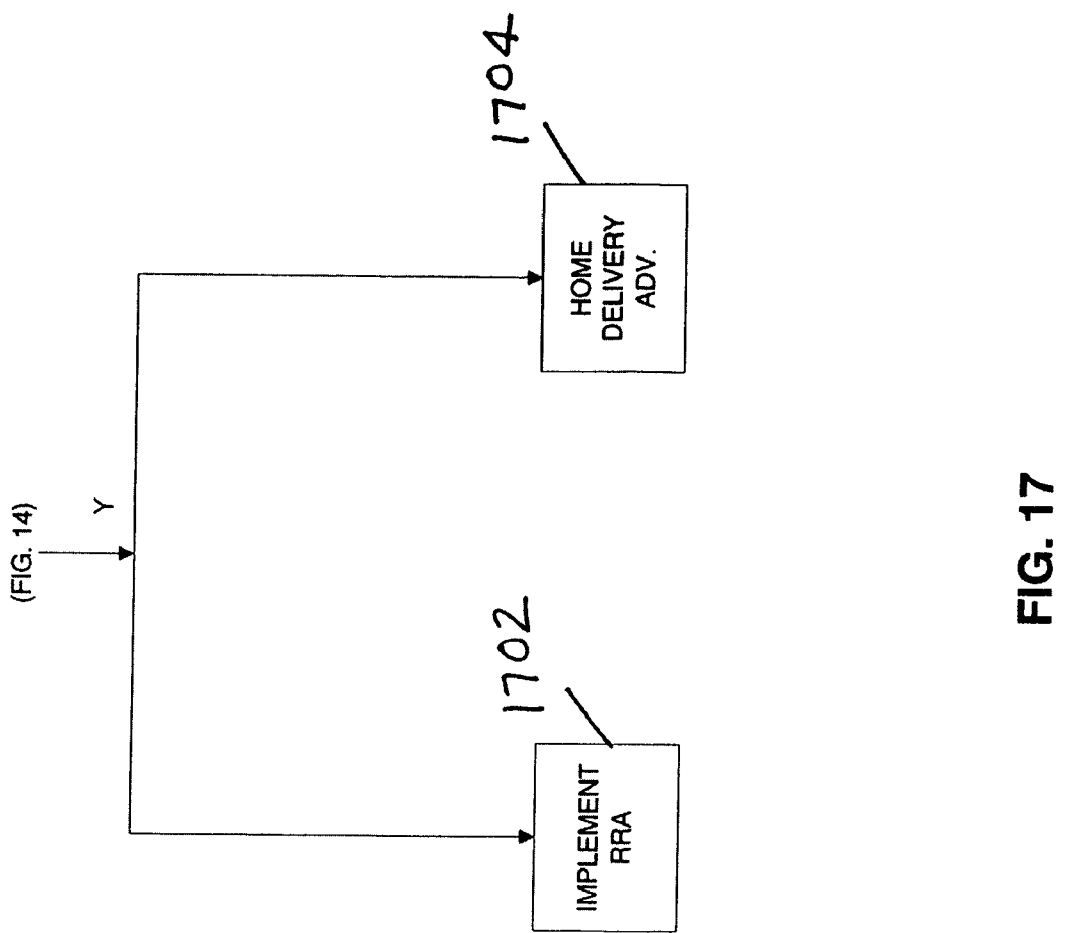
Figure 18:
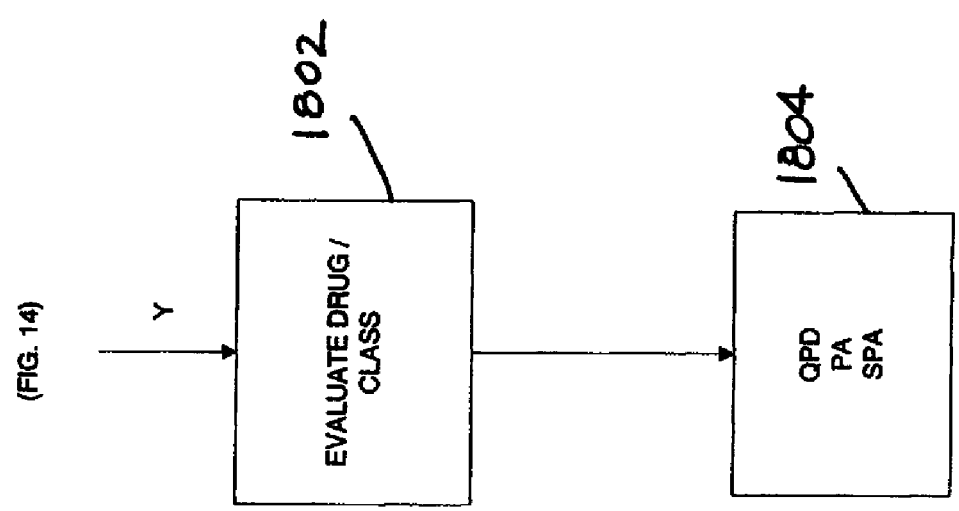
Figure 19:
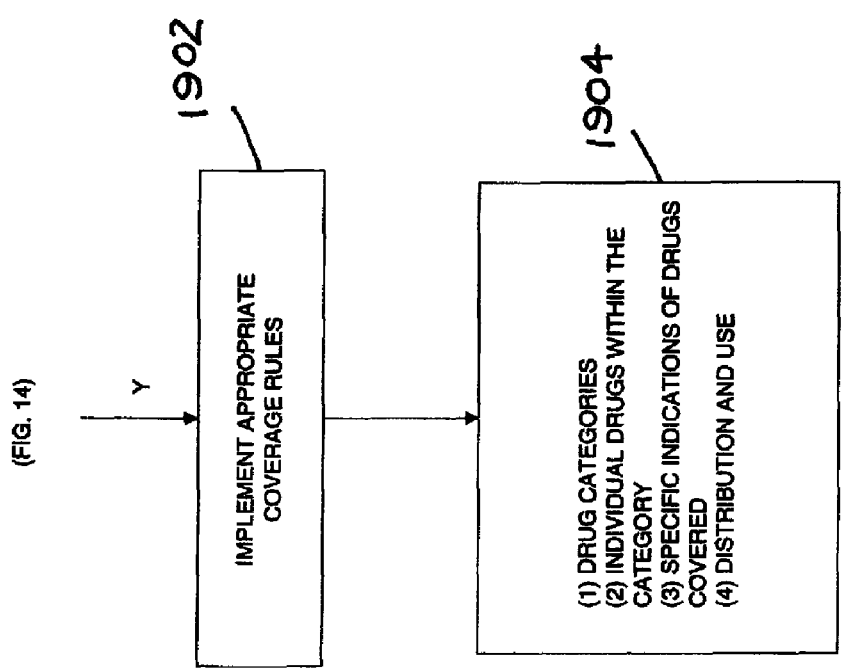

Referring back to FIG. 14, at step 1408, the application evaluates whether a client's home delivery ("HD") rate is less than a desired target. If the home delivery rate is less than the target, then the spend and trend application provides options 1702 or 1704 (FIG. 17). Option 1702 provides for the implementation of a retail refill allowance program; and option 1704 provides for the implementation of a home delivery advantage program.

Referring back to FIG. 14, at step 1410, the application evaluates whether a client's specialty medications usage is greater than a desired target. If the specialty medications usage is greater than the target, then the spend and trend application proceeds to step 1802 and evaluate the specific drugs or therapeutic classes that are the subject of the increased specialty medication usage. Based on the evaluation of specialty drugs and/or their respective therapeutic classifications, the application provides option 1804. Option 1804 may include, for example, implementation of a quantity per dispensing ("QPD") limit, prior authorization ("PA"), and smart PA.

Referring back to FIG. 14, at step 1412, the application evaluates whether a disease-specific trend for a client is greater than a desired target. If a disease-specific trend is greater than the target, then the spend and trend application proceeds to step 1902 which involves the implementation of appropriate coverage rules. Option 1904 sets forth possible coverage rules to address the disease-specific trend deviation, including rules addressing drug categories, individual drugs within a category, specific indications of covered drugs, and drug distribution and use by plan members.

Figure 20:
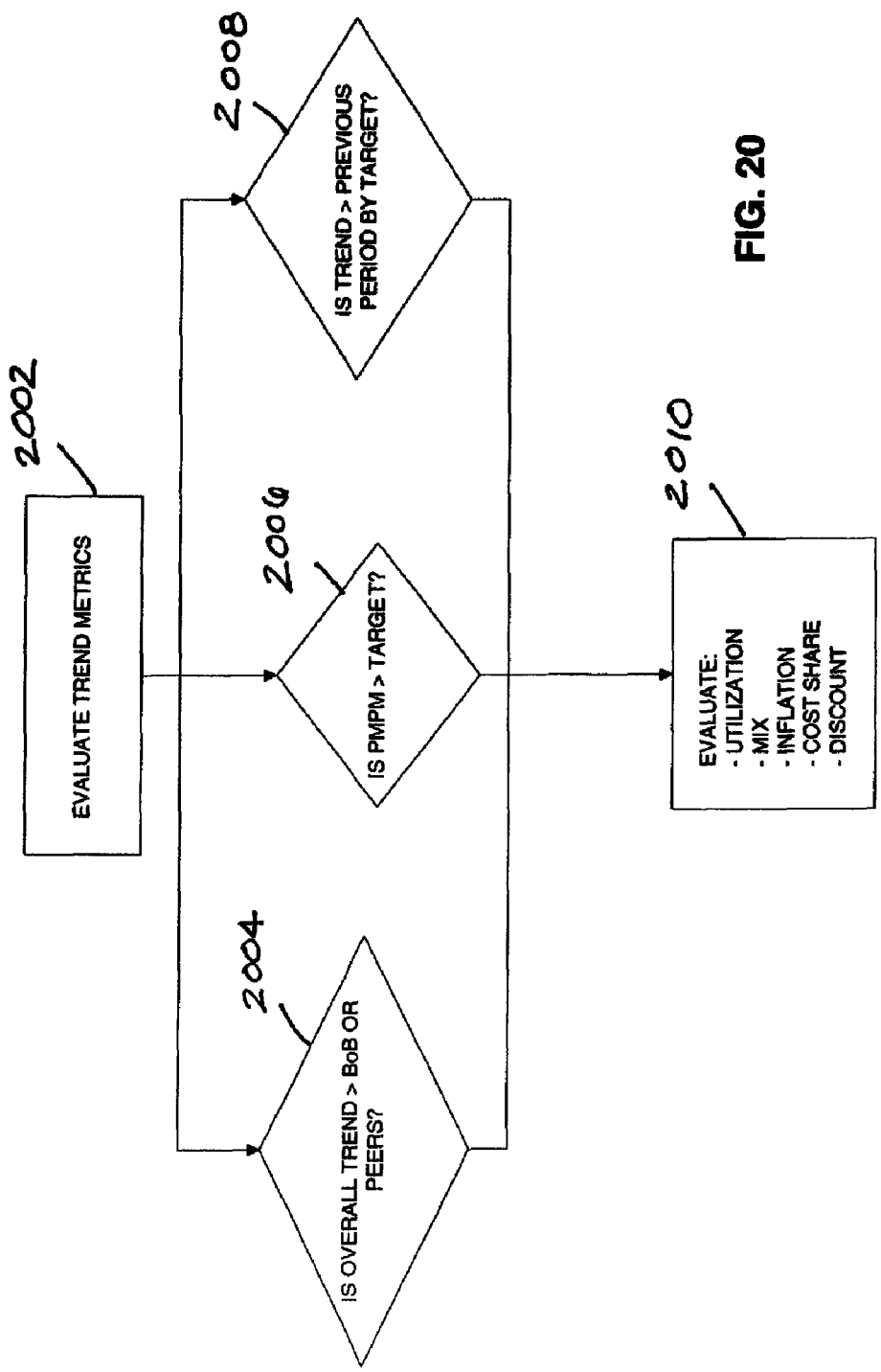
FIG. 20 is an illustrative flow diagram that demonstrates a method for evaluating trend metrics for a prescription drug plan in a prescription drug plan management system in accordance with some embodiments of the present invention.

FIG. 20 is an illustrative flow diagram that demonstrates a method for evaluating trend metrics for a prescription drug plan in a prescription drug plan management system in accordance with some embodiments of the present invention. At step 2002, the spend and trend application may evaluate any applicable prescription drug trend metrics by comparing the actual value for the plan to a target value. These trend metrics may include a target value set by a user (e.g., a plan administrator) or default target values. The examples provided in FIG. 20 are merely illustrative, and the spend and trend application may evaluate some, all, or alternative trend metrics in connection with a client's prescription drug plan.

At step 2004, the application may evaluate whether a client's overall trend is greater than the overall trend for other prescription drug plans in the plan manager's book of business ("BoB") or other peers of the client. For example, a pharmacy benefit manager that manages prescription drug plans for numerous clients may have data corresponding to the overall trend for other clients. This data constitutes the pharmacy benefit manager's "book of business," and the trend metric evaluation may involve a comparison of the client's overall trend to other clients managed by the same plan manager. This may also be referred to herein as "benchmarking," in that a client may determine how its prescription drug plan is doing in comparison to others. As shown in step 2004, the overall trend may also be compared, or benchmarked, to peers outside of the pharmacy benefit manager's book of business. Another comparison that may be performed by the spend and trend application is an evaluation of the prescription drug plan's per-member per-month (PMPM) rates. In particular, at step 2006, the spend and trend application may evaluate whether a client's PMPM rate is greater than a desired target. Yet another comparison that may be performed by the application is an evaluation of whether the client's overall trend is greater than the trend for the previous period (e.g., month, quarter, etc.) by some desired target.

If some or all of the comparisons made in steps 2004, 2006, or 2008 demonstrate that a trend metric has deviated from a desired target range, then the application may proceed to step 2010 and evaluate drug utilization, drug mix, inflation, cost share, or any applicable discounts for the prescription drug plan. An evaluation of these factors may yield appropriate options for reducing trend for the prescription drug plan.

Figure 21:
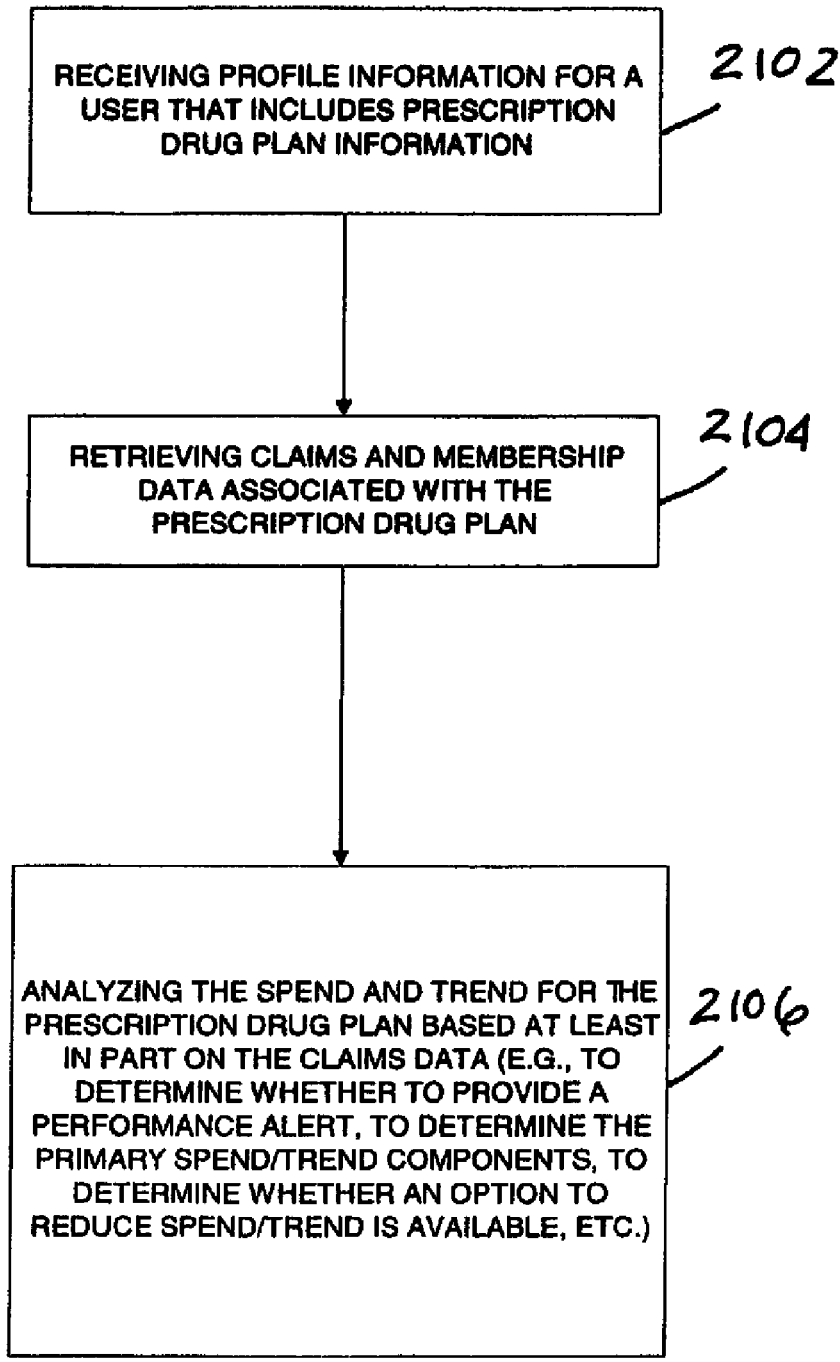
FIG. 21 is an illustrative flow diagram that demonstrates a method for analyzing spend and trend for a prescription drug plan in a prescription drug plan management system in accordance with some embodiments of the present invention.

FIG. 21 is an illustrative flow diagram that demonstrates a method for analyzing spend and trend for a prescription drug plan in a prescription drug plan management system in accordance with some embodiments of the present invention. At step 2102, the spend and trend application of the present invention may receive profile information for a user that includes prescription drug plan information. For example, a plan administrator may input profile information at a workstation (e.g., administrator computer 304 of FIG. 3) as requested by the spend and trend application. Alternatively, the application may receive profile information for a user, or client, from any other suitable source. At step 2104, the application may retrieve data associated with the prescription drug plan. For example, the application may retrieve claims and membership data from information warehouse 310 of FIG. 3. Based at least in part on the retrieved data, the application may analyze the spend and trend for the prescription drug plan at step 2106. From this analysis, the application may, for example, determine whether to provide a performance alert (see, for example, FIG. 22), determine the primary components of spend and trend (see, for example, FIG. 23), or determine whether an option to reduce spend and trend is available (see, for example, FIG. 24).

Figure 22:
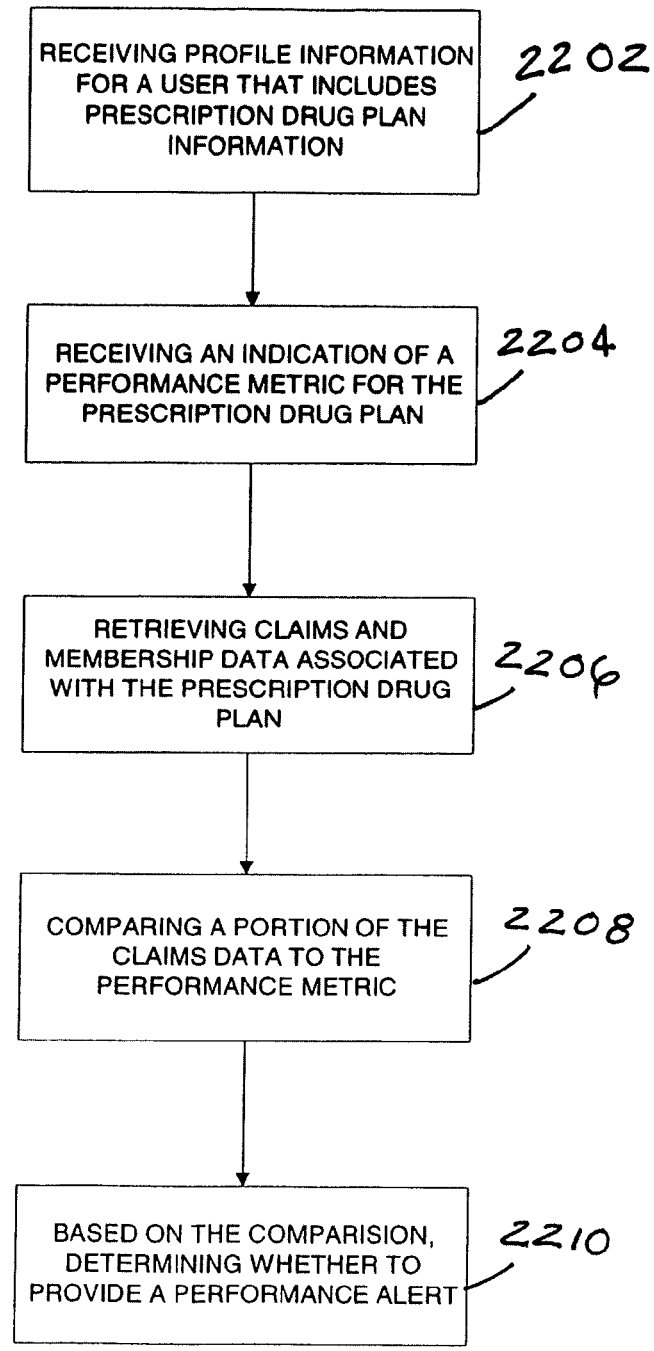
FIG. 22 is an illustrative flow diagram that demonstrates a method for providing performance alerts for a prescription drug plan in a prescription drug plan management system in accordance with some embodiments of the present invention.

FIG. 22 is an illustrative flow diagram that demonstrates a method for providing performance alerts for a prescription drug plan in a prescription drug plan management system in accordance with some embodiments of the present invention. At step 2202, the application may receive profile information for a user that includes prescription drug plan information. At step 2204, the application may receive an indication of a performance metric for the prescription drug plan. For example, as described in connection with FIGS. 14-20, a user may set a target for certain prescription drug plan parameters affecting spend and trend. At step 2206, the application may retrieve data associated with the prescription drug plan (e.g., claims data, membership data). A portion of the claims data may be compared to the performance metric at step 2208. For example, if the performance metric involves cost share (see, for example, FIG. 15), then the application may compare the cost share data to the performance metric. Based on the comparison, the application may determine at step 2210 whether to provide a performance alert. A performance alert may be provided if the comparison of the claims data to the performance metric indicates that the plan is not performing as desired.

Figure 23:
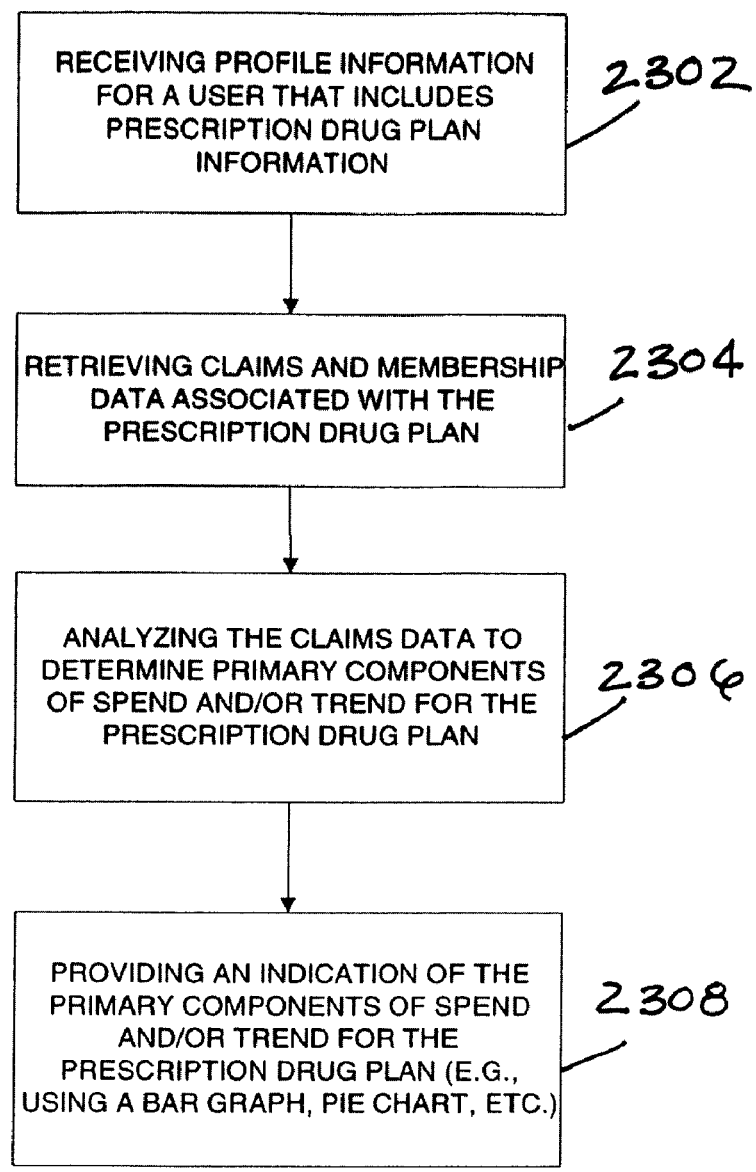
FIG. 23 is an illustrative flow diagram that demonstrates a method for providing an indication of the primary components of spend and/or trend for a prescription drug plan in a prescription drug plan management system in accordance with some embodiments of the present invention.

FIG. 23 is an illustrative flow diagram that demonstrates a method for providing an indication of the primary components of spend and/or trend for a prescription drug plan in a prescription drug plan management system in accordance with some embodiments of the present invention. At step 2302, the spend and trend application may receive profile information for a user that includes prescription drug plan information. At step 2304, the application may retrieve data (e.g., claims data, membership data) associated with the prescription drug plan. The retrieved data may be analyzed at step 2306 to determine the primary components of spend and trend for the prescription drug plan. These primary components may be provided to the user at step 2308. For example, the application may communicate a screen that includes an indication of the primary components of spend and trend to front end 402 (FIG. 4), to be displayed on the user or administrator computer (e.g., user and administrator computers 302 and 304 of FIG. 3). This information may be provided in the form of a bar graph, pie chart, table, or any other suitable format for communicating the primary components of the plan's spend and trend.

Figure 24:
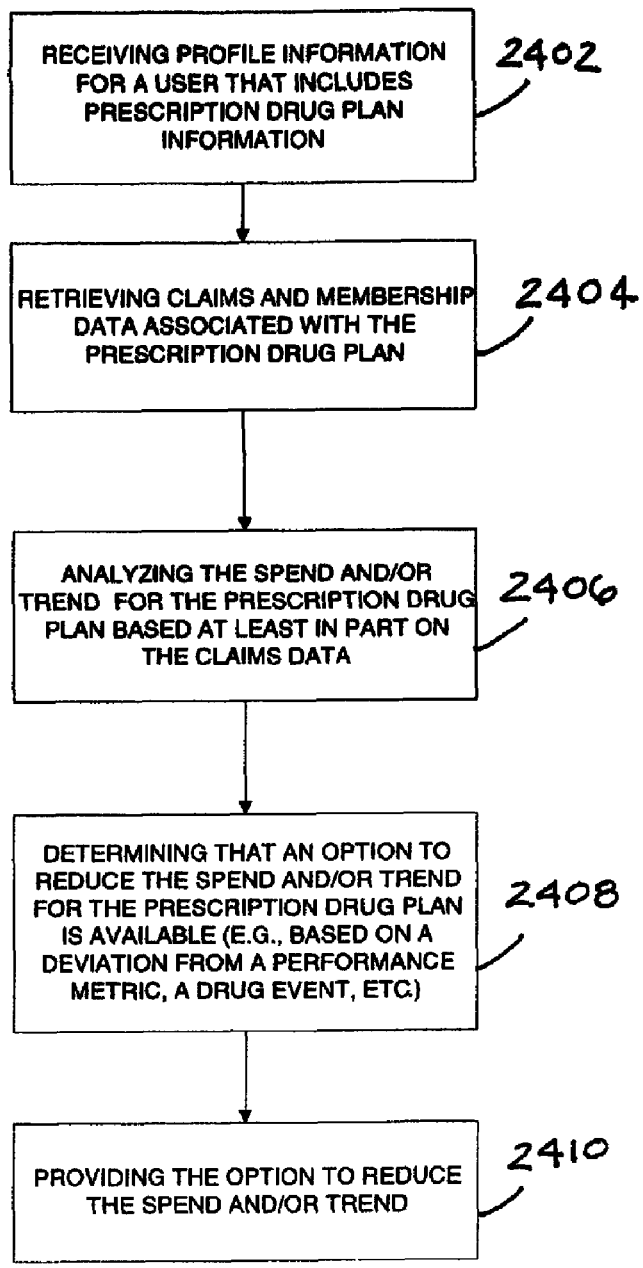
FIG. 24 is an illustrative flow diagram that demonstrates a method for providing an option to reduce spend and/or trend for a prescription drug plan in a prescription drug plan management system in accordance with some embodiments of the present invention.

FIG. 24 is an illustrative flow diagram that demonstrates a method for providing an option to reduce spend and/or trend for a prescription drug plan in a prescription drug plan management system in accordance with some embodiments of the present invention. At step 2402, the application receives profile information for a user that includes prescription drug plan information. At step 2404, the application retrieves data (e.g., claims data, membership data) associated with the prescription drug plan. The application analyzes the spend and/or trend for the prescription drug plan based at least in part on the retrieved data at step 2406. Based on the analysis of spend and trend, the application determines whether an option to reduce the spend and trend of the prescription drug plan is available. For example, if the plan deviates from a performance metric (see, for example, FIG. 22), then the application may determine that there is an option available based on the deviation to improve the plan's spend and trend. In another example, an option to reduce spend and trend for the plan may be based on a drug event in the marketplace. Such events may include, for example, the introduction of a new drug, a market withdrawal of an existing drug, the expiration of a patent for a drug, a shift from prescription to over-the-counter for a drug, a new indication for a drug, or any other suitable drug event. In yet another example, an option to reduce spend and trend may be based on the primary components of spend and trend determined by the application (see, for example, FIG. 23). The application may provide an option designed to minimize one or more of the primary components of spend and trend. At step 2410, the application may provide the option to reduce spend and/or trend to the user.

Figure 25:
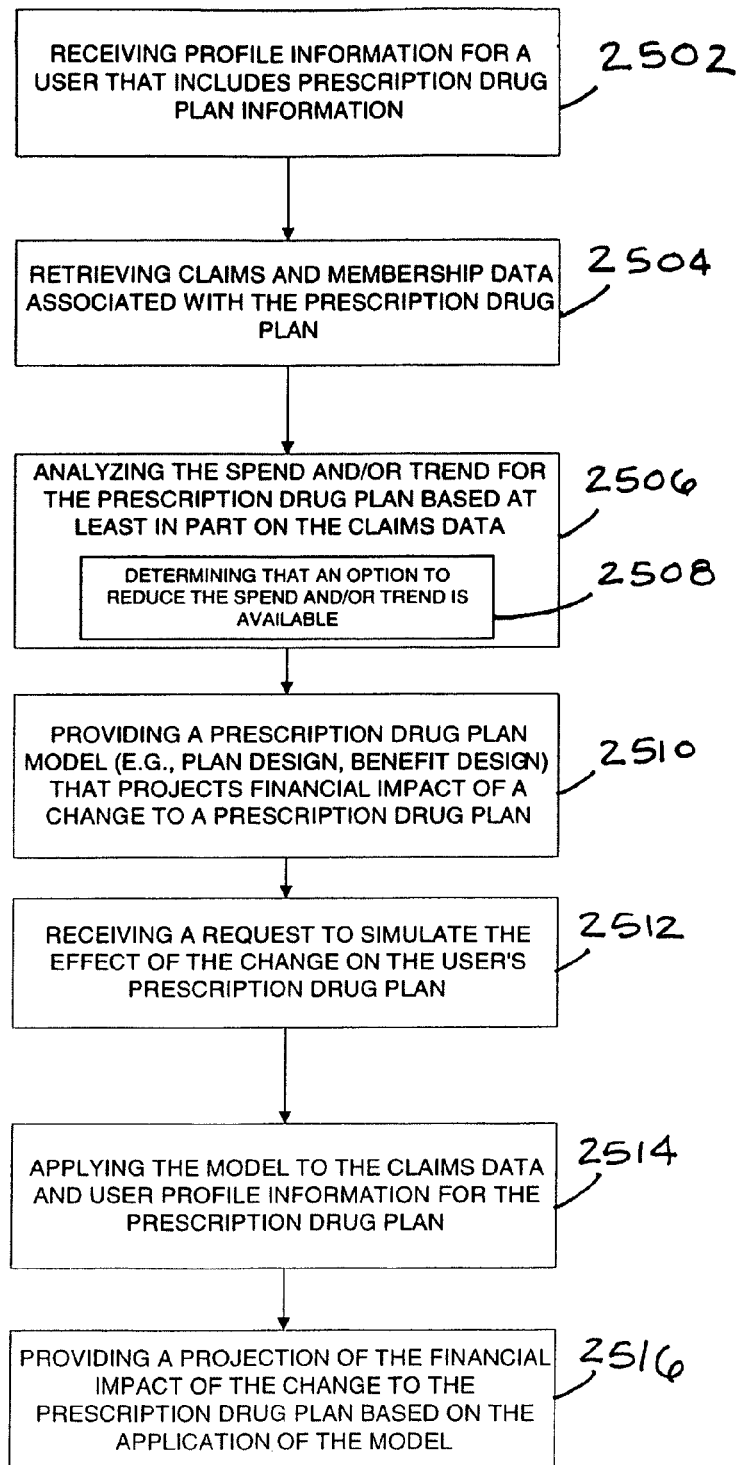
FIG. 25 is an illustrative flow diagram that demonstrates a method for providing a projection of the impact of a change to a prescription drug plan by applying a model in a prescription drug plan management system in accordance with some embodiments of the present invention.

FIG. 25 is an illustrative flow diagram that demonstrates a method for providing a projection of the impact (e.g., financial impact, member impact) of a change to a prescription drug plan by applying a model in a prescription drug plan management system in accordance with some embodiments of the present invention. The projected change to the prescription drug plan may be, for example, a benefit design change or a plan design change. Tables of exemplary benefit design and plan design models is provided hereinbelow. It should be noted that the models listed are for illustration only, and the present invention may apply any suitable model to a prescription drug plan to project the impact of a change to the plan.

| BENEFIT DESIGN MODELS | |
| --- | --- |
| Name | Description |
| Formulary Options | Provides the capability to determine the rebate impact of changes to formulary content and co-pays. |
| Therapeutic Class Optimizer | Provides estimated rebate and net cost impact of moving specific drugs on or off formulary for various therapeutic classes. |
| Dose Optimization | Projects the estimated financial and member impact of implementing dose optimization rules. |
| Quantity per Dispensing Event | Projects the estimated financial and member impact of implementing QPDE Coverage Authorization Rules. |
| Smart Rules | Projects the estimated financial and member impact of implementing "smart" coverage authorization rules. |
| Traditional Prior Authorization | Projects the estimated financial and member impact of implementing traditional prior authorization rules. |
| Specialty | Projects the estimated drug spend and discount impact associated with implementing Medco's Specialty Pharmacy offering. Note: This model may account for specialty prescription drug spend only. Specialty pharmacy costs associated with a client's medical plan may not be included. |
| New Drug Events | Models the estimated impact of new drug events, including new drug introductions, market withdrawal of an existing drug, new drug indications, patent expirations, and conversion of products from prescription to over-the-counter ("OTC") status. |
| Medicare COB | Calculates the estimated financial impact of implementing the Medicare Part B Subrogation (Recovery) program for home delivery claims. |
| Inclusions/ exclusions | Models the estimated impact of including or excluding drugs that are typically considered for exclusion from coverage. |

| PLAN DESIGN MODELS | |
| --- | --- |
| Name | Description |
| Member Cost Share | This model is also referred to as the "Mega Model." It is the model option that may be selected most often. This allows a user to model changes to open and incentive co-pay structures of a plurality of tiers (e.g., up to four tiers). Cost share can be flat dollar, co-insurance with or without minimums and maximums, or a mixture of flat dollar and co-insurance. A user can model co-pay changes with retail refill allowance and home delivery advantage, as well as generic and formulary shifts. Selecting the home delivery option when using the member cost share model allows a user to determine whether cost share is aligned between the retail and home delivery channels. |
| Retail Refill Allowance | Provides a user with the ability to model stand-alone retail refill allowance at any refill threshold. |
| Home Delivery Advantage | Provides a user with the ability to model stand-alone home delivery advantage. This model can be used to test retail and home delivery co-pay alignment. |
| Member pay the difference | Provides a user with the ability to model both managed and sensitive member pay the difference programs. |

-continued

| | |
| --- | --- |
| Generic Bundle | A compilation of several models that promote generic utilization, this model includes dose duration, step therapy, incentive co-pay, and member pay the difference models. |
| Out of Pocket Maximum | Provides a user with the ability to model out of pocket maximums with or without deductibles and co-pay changes. A user can choose to include the deductibles model when modeling out of pocket maximums. |
| Deductibles | Provides a user with the ability to model deductibles with or without out-of-pocket and co-pay changes. A user can choose to include the out of pocket model when modeling deductibles. |
| RationalMed ™ | Projects the estimated financial impact of implementing the RationalMed Patient Safety program. This model may include prescription drug spend only. |
| Benefit Cap | Provides the capability to model the addition of a benefit cap. |
| Retail Access Density | Provides the ability to remove super chains from an existing retail PPO and determine the member impact of the change. |

The models provided in the above tables may be classified as financial, clinical, or other. In particular, those models which simulate a change to a financial aspect of a prescription drug plan (e.g., member cost share, member pay the difference, formulary options, out of pocket maximum, deductibles) may be classified as "financial." Those models which simulate a change to a clinical aspect of a prescription drug plan (e.g., smart rules, dose optimization, traditional prior authorization, quantity per dispensing event, new drug events) may be classified as "clinical." Those models which may not fit either of these classifications (e.g., therapeutic class optimizer) may be classified as "other."

The models provided in the above tables, or any alternative models, may be applied to a prescription drug plan to project the impact of a change to the plan. The application of some of the models may be additive. For example, a model may be applied to the plan, and the impact projected. An additional model may then be applied to the projected plan data, thereby projecting the impact of both of the models on the prescription drug plan. Alternatively, two or more models may be applied to a prescription drug plan concurrently, thereby providing a simultaneous projection of the impact of more than one change to the prescription drug plan.

As shown in FIG. 25, at step 2502, the application may receive profile information for a user that includes prescription drug plan information. At step 2504, the application may retrieve data (e.g., claims data, membership data) associated with the prescription drug plan. The application may analyze the spend and trend for the prescription drug plan based at least in part on the retrieved data at step 2506. The spend and trend analysis at step 2506 may involve a determination that an option to reduce spend and/or trend for the prescription drug plan is available at sub-step 2508 (see, for example, FIG. 24). At step 2510, the application may provide a prescription drug plan model that projects the impact of a change to the prescription drug plan (e.g., plan design change, benefit design change). In the event that the application determines that an option to reduce spend and trend is available at step 2508, the application may provide a model that can project the impact of the implementation of the option on the prescription drug plan. Alternatively, the application may provide a plurality of models that are applicable to the plan, whether or not an option to reduce spend and trend is available.

The application may receive a request to simulate the effect of the change on the user's prescription drug plan at step

2512. In the event that the application provided a model based on an available option, a user may select the option for application of its related model. Alternatively, a user may select a model from a list of available models for application to the prescription drug plan. At step 2514, the application may apply the model to the retrieved data and user profile information for the prescription drug plan. Based on the application of the model to the relevant plan information and data, the application may provide a projection of the impact of the change to the prescription drug plan at step 2516. Such projected impact may be financial impact, member impact, or any other impact that the selected change may yield in the prescription drug plan.

Figure 26:
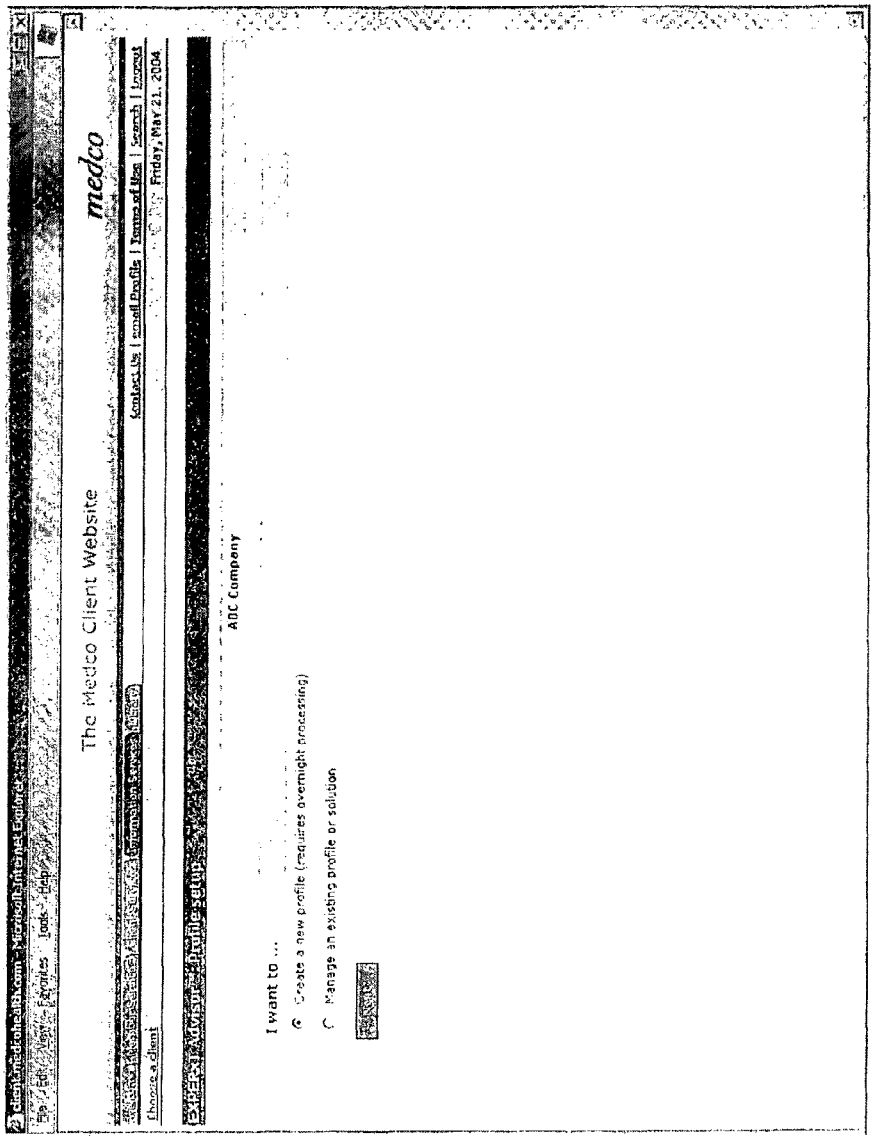
FIG. 26 is an illustrative user profile setup screen that may be provided by the prescription drug spend and trend application in accordance with some embodiments of the present invention.

An illustrative user profile setup screen 2600 that may be provided by the prescription drug spend and trend application is shown in FIG. 26. As shown, screen 2600 of FIG. 26 is designed to be provided on a computer display (e.g., a display of user computer 302 or administrator computer 304 of FIG. 3). However, it should be noted that the format and contents of the screens that follow may be modified to accommodate different platforms, if desired. It should also be noted that some, all, or alternatives to the following screens may be provided to a user of the spend and trend application in accordance with the present invention.

Figure 27:
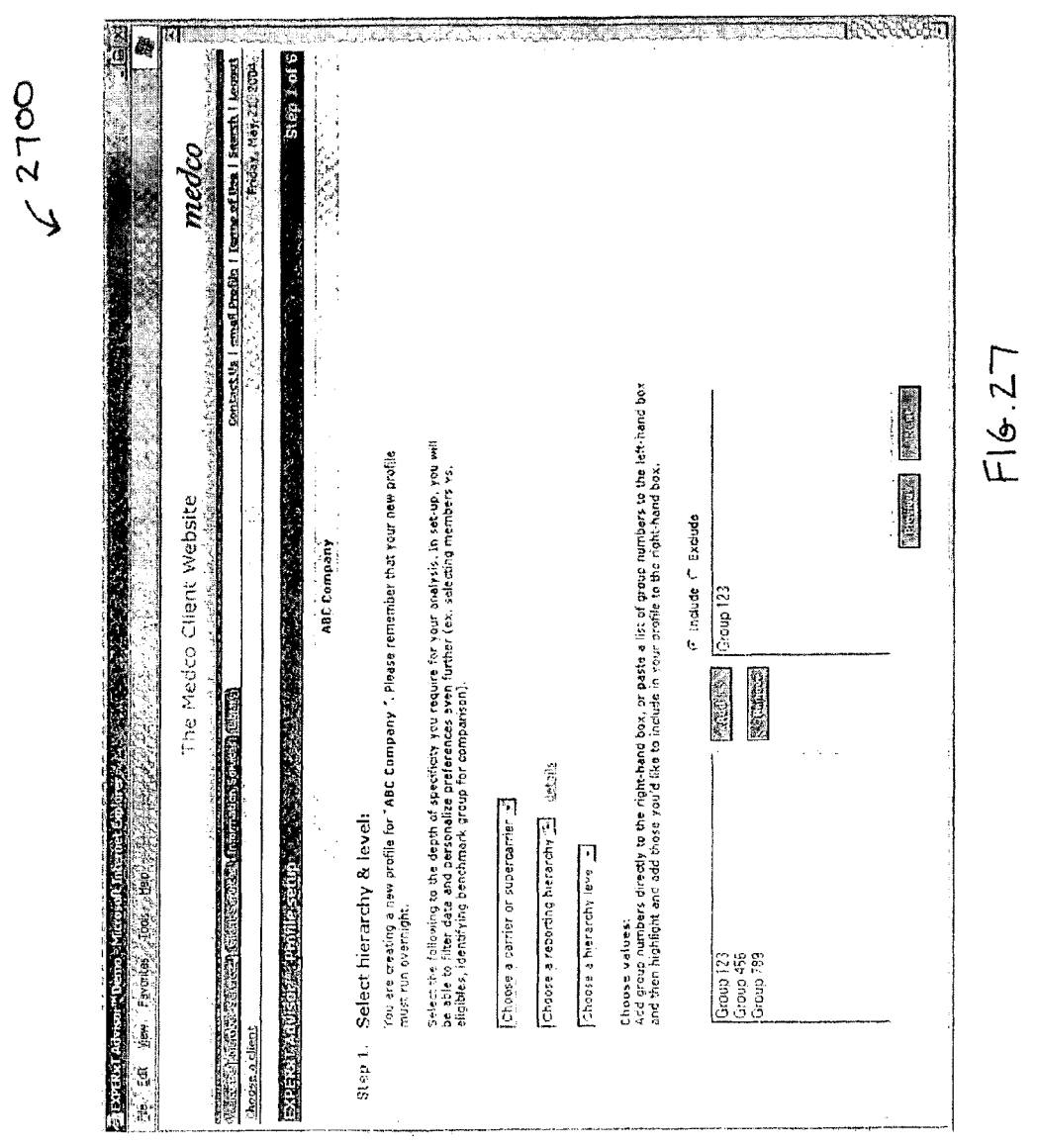

User profile setup screen 2600 of FIG. 26 provides a user with the ability to create a client profile or update an existing client profile. To create a profile for a client, the user may select "Create a new profile" and the "Next" button using any suitable user input device (e.g., user input device 206 of FIG. 2). If the user selects to create a new profile, the application may provide the user with the screen of FIG. 27. FIG. 27 is an illustrative hierarchy and level selection screen 2700 that may be provided by the prescription drug spend and trend application in accordance with some embodiments of the present invention. As shown, screen 2700 allows the user to create a specific reporting hierarchy for the client.

Figure 28:
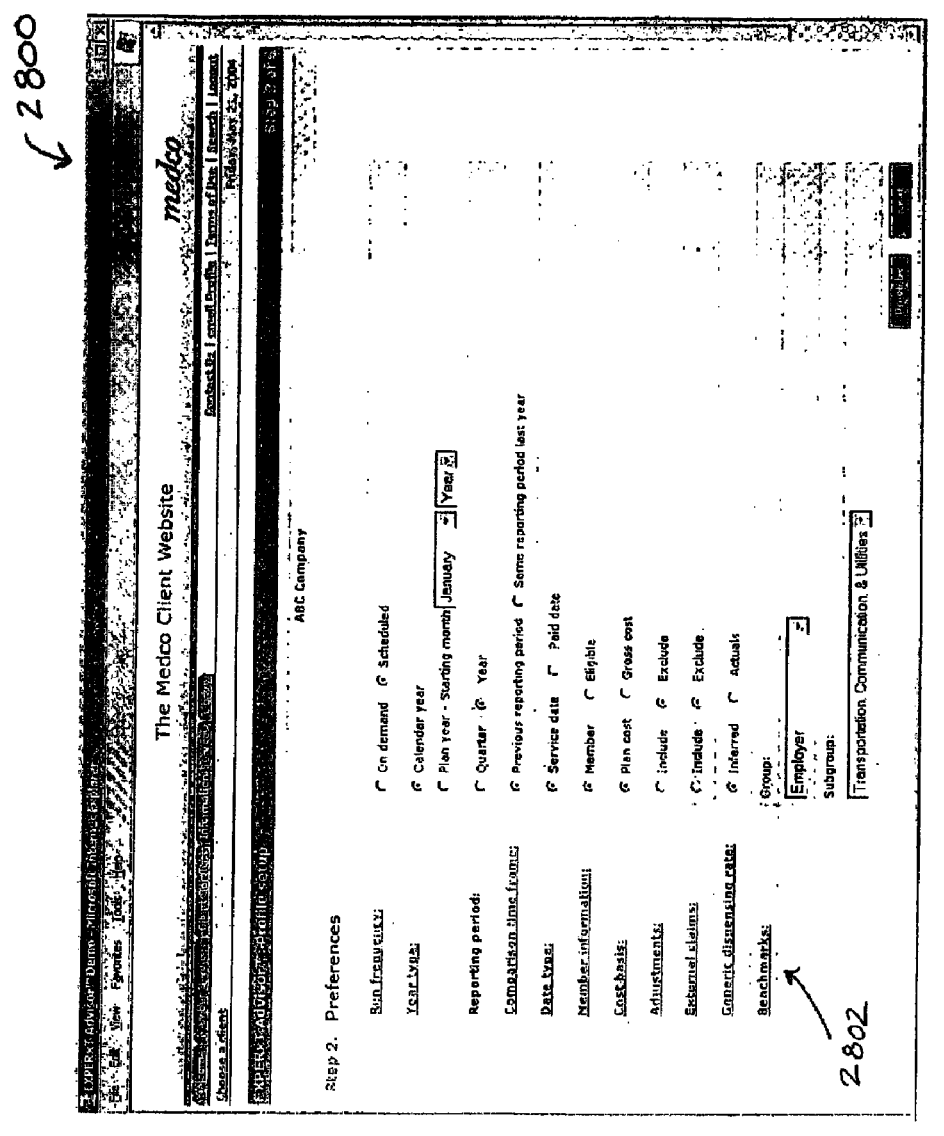

FIG. 28 is an illustrative preferences screen 2800 that may be provided by the prescription drug spend and trend application in accordance with some embodiments of the present invention. Preferences screen 2800 allows the user to select preferences, which establishes parameters for the data being used for spend and trend analysis. For example, the preferences selected on screen 2800 may affect the data retrieved from information warehouse 310 by application server 308 (FIG. 3) in analyzing spend and trend for a prescription drug plan.

Preferences screen 2800 may include a run frequency option, from which a user can select "On demand" or "Scheduled." If the user selects "Scheduled," then the spend and trend application automatically generates data updates to the plan profile at certain intervals (e.g., monthly, quarterly, etc.). If the user selects "On demand," then the spend and trend application may create a "snapshot" based on the data available for the client at that point in time.

Preferences screen 2800 may include a year type option, from which a user can select "Calendar year" or "Plan year." Plan year may apply, for example, in situations where a client manages to a fiscal year that begins in April and ends the following March. If a user selects "Plan year," then the user also specifies a starting month and year. Preferences screen 2800 may include a reporting period option, which allows the user to specify whether the spend and trend application should extract data from the information warehouse (e.g., information warehouse 310 of FIG. 3) for the previous quarter or year.

Preferences screen 2800 may include a comparison time frame option for comparison with the plan's current performance. For example, a user may select "Previous reporting period" (e.g., 2Q04 compared to 1Q04) or "Same reporting period last year" (e.g., 2Q04 compared to 2Q03). Preferences screen 2800 may include a date type option, which allows the user to select either a "Service date" (i.e., the date on which the service was performed) or "Paid date" (i.e., the date on which the claim was paid) for claims data.

Preferences screen 2800 may include a member information option, which allows the user to specify whether calculations are to be performed on a member or eligible member basis. Preferences screen 2800 may include a cost basis option, which allows the user to specify whether calculations are performed on "Plan cost" (i.e., exclusive of member cost share) or "Gross cost" (i.e., total costs inclusive of member cost share).

Preferences screen 2800 may include an adjustments option, which allows the user to either include or exclude adjustment costs from calculations performed by the spend and trend application. Adjustments are corrections to adjudicated claims. For example, if co-pays are incorrect in the system, the claims will need to be adjusted. Adjustments may skew results depending on when they are processed. An approach with regard to the adjustments option may be to exclude adjustments for quarterly profiles and to include adjustments for annual profiles.

Preferences screen 2800 may include an external claims option, which allows the user to either include or exclude external claims from calculations performed by the spend and trend application. External claims are those claims adjudicated by another pharmacy benefit manager (i.e., a pharmacy benefit manager other than the manager for the particular client's prescription drug plan). A client, for example, may provide the pharmacy benefit manager with external claims data to load into the information warehouse (e.g., information warehouse 310 of FIG. 3) in order to perform drug utilization review ("DUR") as well as reporting and/or analysis.

Preferences screen 2800 may include a generic dispensing rate option, which allows the user to select either "Inferred" or "Actual." Inferred or actual is determined by how multi-source and generic drugs are classified. An inferred rate calculation classifies generics versus multi-source drugs by how they were priced. For example, if a multi-source drug is priced by a maximum allowable cost ("MAC"), it is considered a generic under the inferred method. An actual rate calculation classifies generics versus multi-source drugs by how they are labeled by, for example, First Data Bank, regardless of pricing.

Preferences screen may include a "Benchmarks" preference 2802, which allows the user to select a particular group or subgroup for comparison with the client's prescription drug plan. This feature allows a user to determine how well the client's prescription drug plan is performing relative to other plans, both within the pharmacy benefit manager's book of business, and in the overall prescription drug plan marketplace.

Figure 29:
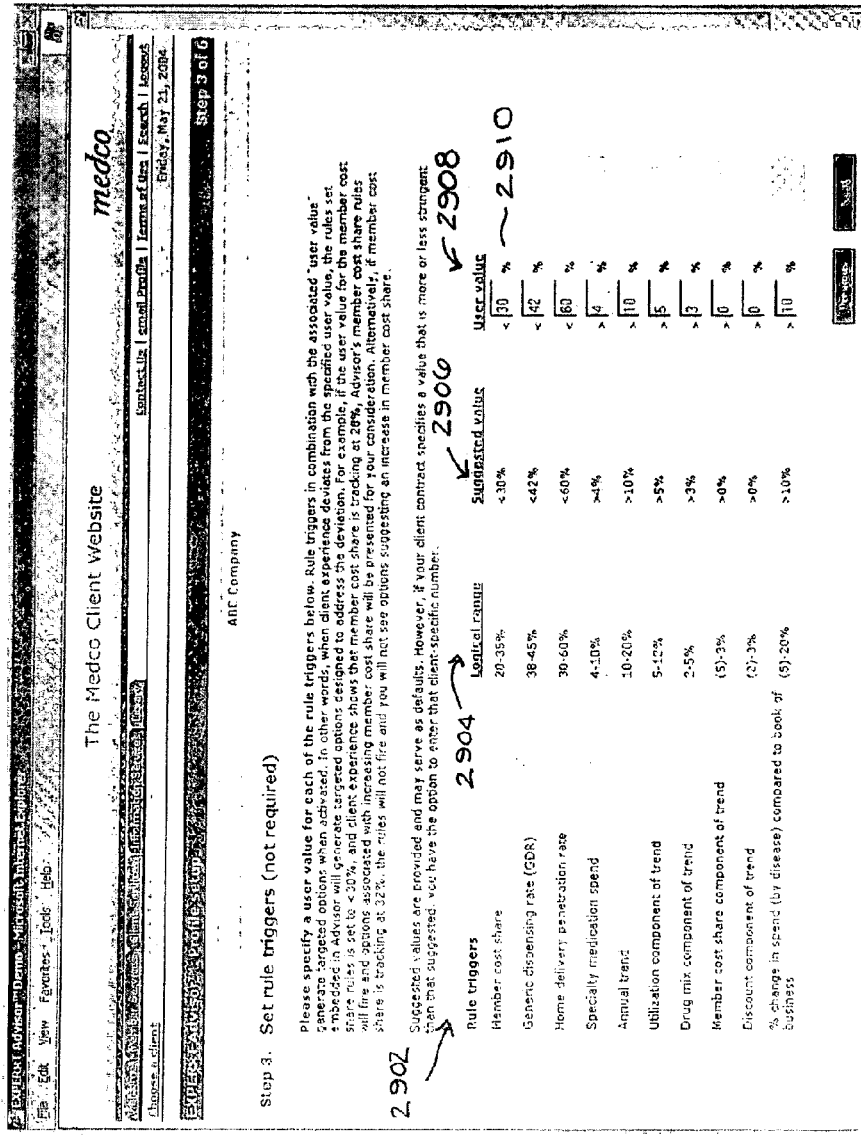
FIG. 29 is an illustrative rule trigger selection screen that may be provided by the prescription drug spend and trend application in accordance with some embodiments of the present invention.

FIG. 29 is an illustrative rule trigger selection screen 2900 that may be provided by the prescription drug spend and trend application in accordance with some embodiments of the present invention. Rule triggers are substantially similar to the performance metrics described hereinabove in connection with FIGS. 14-20, with the difference that a deviation from a rule trigger will result in the automatic determination of whether an option exists to improve the prescription plan. In contrast, deviation from a performance metric (see, for example, FIG. 30) may or may not result in the automatic determination or generation of an option to resolve the deviation.

Screen 2900 provides the user with the ability to set various rule triggers 2902 to a desired value 2908. To assist the user, screen 2900 provides a logical range 2904 for a specific trigger, and a suggested value 2906. The values provided by the user in fields 2908 dictate when the rules logic of the spend and trend application will be utilized to determine whether an option is available to improve the prescription drug plan's spend and trend. For example, in field 2910, the rule trigger for member cost share has been set at "less than 30%." If the member cost share is less than 30%, then the rules logic of the present invention may be utilized to provide an option to increase the member cost share such that it once again approaches 30% (see, for example, the flowcharts of FIGS. 14 and 15).

It should be noted that rule trigger selection screen 2900 may be provided with fields 2908 pre-filled with, for example, default values, by the spend and trend application. A user may elect to keep the values shown in fields 2908, or the user may elect to input other values for the client's prescription drug plan.

FIG. 30 is an illustrative performance metrics and alerts screen 3000 that may be provided by the prescription drug spend and trend application in accordance with some embodiments of the present invention. Screen 3000 provides the user with the ability to set various performance metrics 3002 to desired values 3014. Performance metrics 3002 may be separated by category. For example, as shown in FIG. 30, possible metrics are provided as customer service metrics 3004, trend metrics 3006, and spend metrics 3008. For customer services metrics 3004 (e.g., average speed of answer, call abandonment rate, and first call resolution rate), a data source from which data is drawn by the spend and trend application may include call switch. For trend metrics 3006 (e.g., member cost share, annual trend, utilization component of trend, drug mix component of trend, generic dispensing rate, and generic substitution rate), data sources from which data is drawn by the spend and trend application may include claims data and member eligibility data. For spend metrics 3008 (e.g., home delivery penetration rate, formulary compliance—open, formulary compliance—incentive, specialty drug spend, co-pay alignment (mail vs. retail), and retail net effective discount), a data source from which data is drawn by the spend and trend application may include claims data.

To assist the user, screen 3000 provides a logical range 3010 for a specific metric, and a suggested value 3012. The values provided by the user in fields 3014 dictate when a performance alert will be provided to the user to indicate a deviation from a desired performance metric. A user may elect whether to select a performance metric as an alert by selecting a checkbox 3016. For example, in field 3018, the performance metric for generic dispensing rate has been set at "less than 42%," and box 3020 has been checked indicating that the user desires to receive alerts when the plan deviates from this range. If the generic dispensing rate is less than 42%, then a performance alert may be provided to the user indicating this deviation. As described in connection with FIG. 29, performance metrics screen 3000 may be provided with fields 3014 pre-filled with, for example, default values, by the spend and trend application. A user may elect to keep the values shown in fields 3014, or the user may elect to input other values for the client's prescription drug plan.

Figure 31:
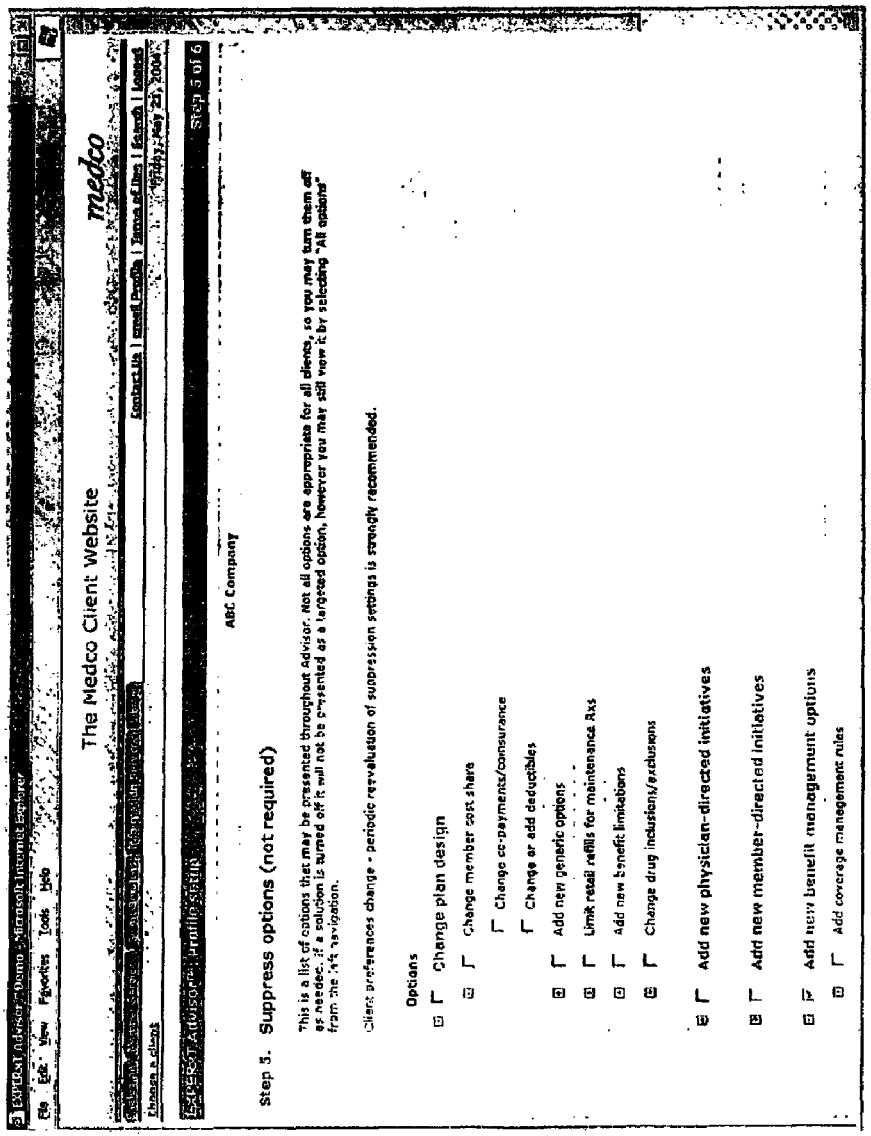
FIG. 31 is an illustrative option suppression screen that may be provided by the prescription drug spend and trend application in accordance with some embodiments of the present invention.

FIG. 31 is an illustrative option suppression screen 3100 that may be provided by the prescription drug spend and trend application in accordance with some embodiments of the present invention. Option suppression screen 3100 allows a user to suppress certain options for the prescription drug plan that may be not be applicable or desirable for a particular client. By suppressing an option or set of options, the rules logic that would otherwise be generated by the rules engine in connection with the option or set of options is disabled. Thus, the application will not provide the suppressed option or options in response to an analysis of the plan's spend and trend, even if the option would otherwise be applicable to improving the plans' spend and trend.

Figure 32:
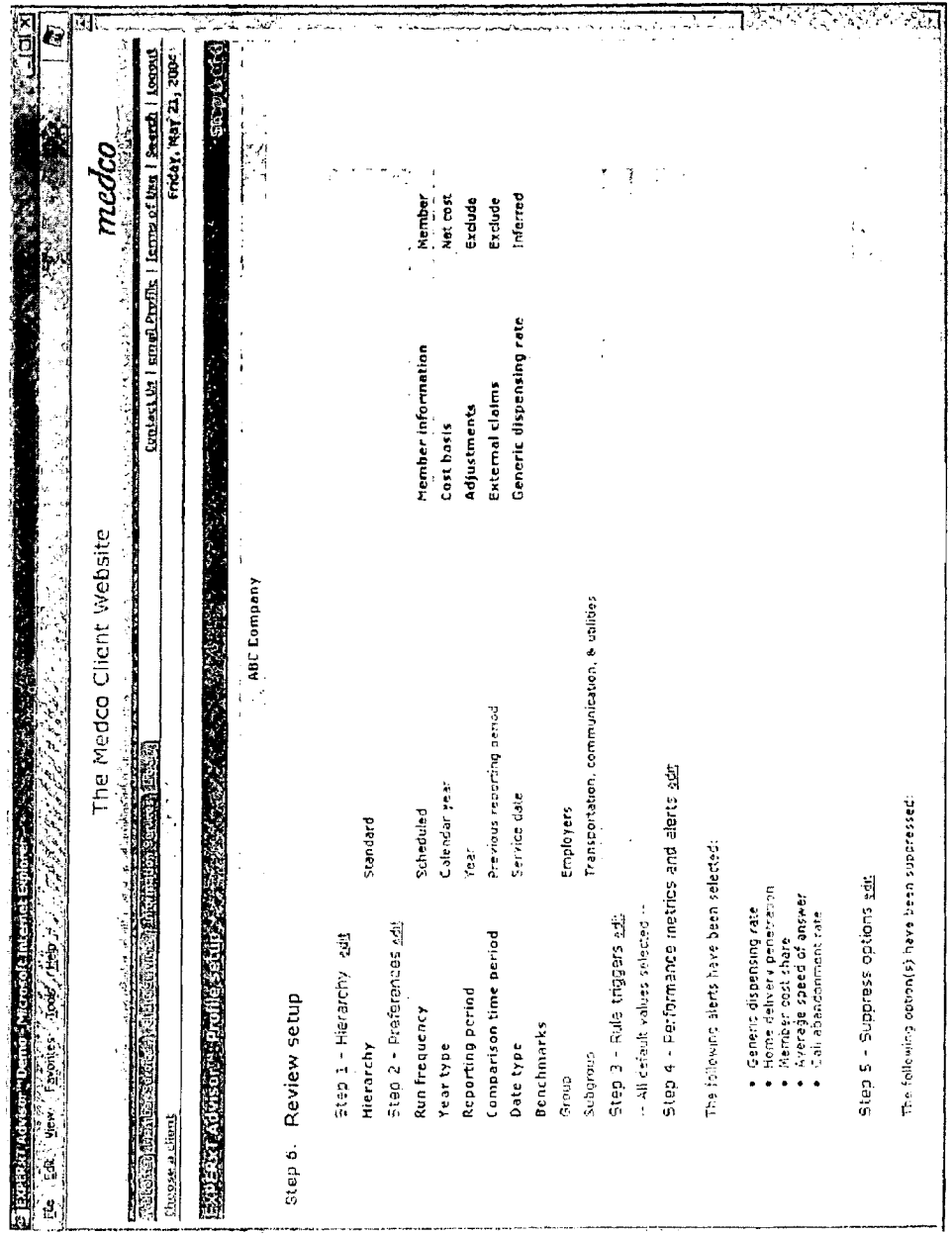
FIG. 32 is an illustrative setup review screen that may be provided by the prescription drug spend and trend application in accordance with some embodiments of the present invention.

FIG. 32 is an illustrative setup review screen 3200 that may be provided by the prescription drug spend and trend application in accordance with some embodiments of the present invention. Setup review screen 3200 allows the user to review and edit profile selections made, for example, in screens 2700-3100 (FIGS. 27-31).

Figure 33:
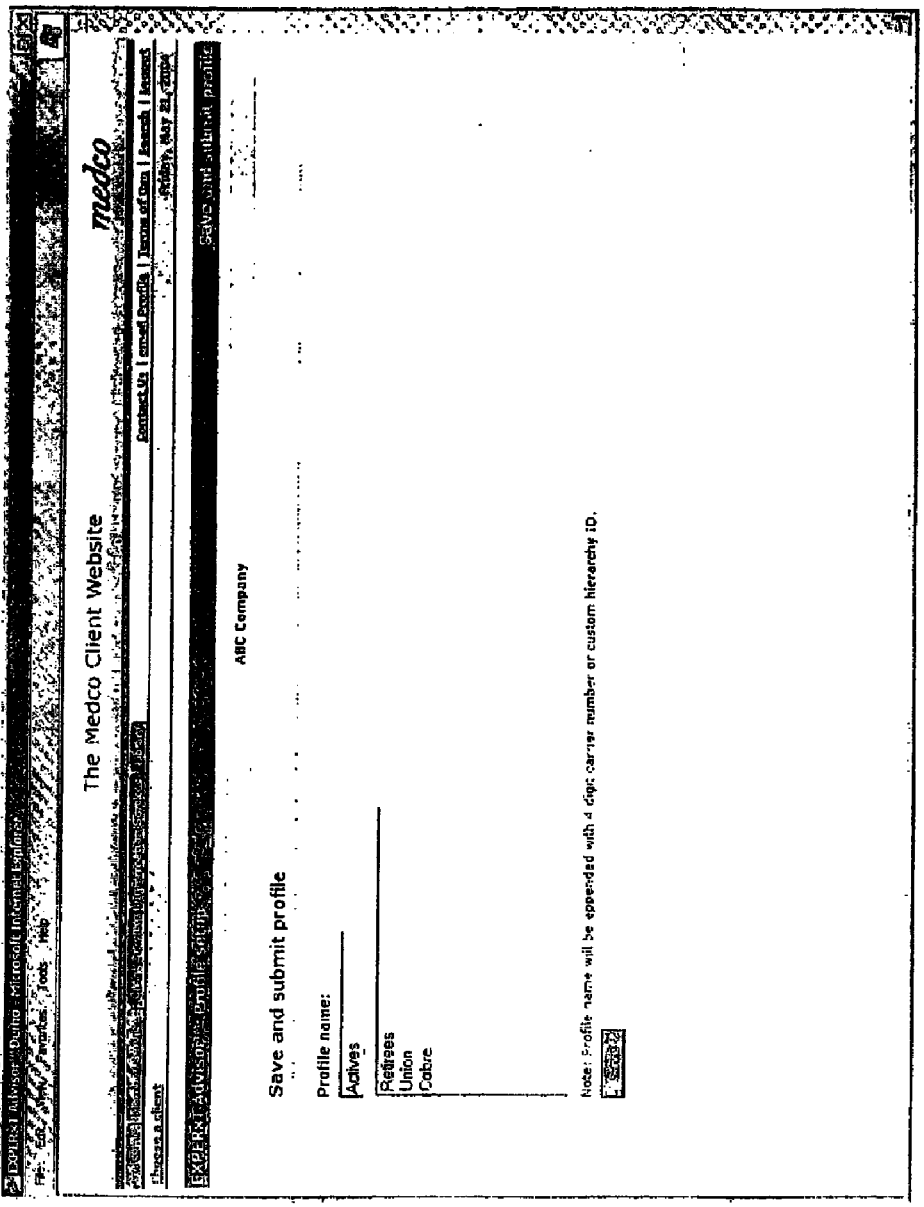
FIG. 33 is an illustrative screen for saving and submitting a user profile that may be provided by the prescription drug spend and trend application in accordance with some embodiments of the present invention.

FIG. 33 is an illustrative screen 3300 for saving and submitting a user profile that may be provided by the prescription drug spend and trend application in accordance with some embodiments of the present invention. Upon selecting the "Save" button, the application may retrieve the required raw data and plan design information from, for example, information warehouse 310 (FIG. 3). In addition to information warehouse 310, data may be retrieved from any other applicable source of data related to the client's prescription drug plan. After the data has been retrieved and the client profile created, the user may be provided with a plan defaults screen.

FIG. 34 is an illustrative prescription drug plan defaults screen 3400 that may be provided by the prescription drug spend and trend application in accordance with some embodiments of the present invention. Screen 3400 requests that the user review and approve the data retrieved by the spend and trend application to populate the client profile.

Figure 35:
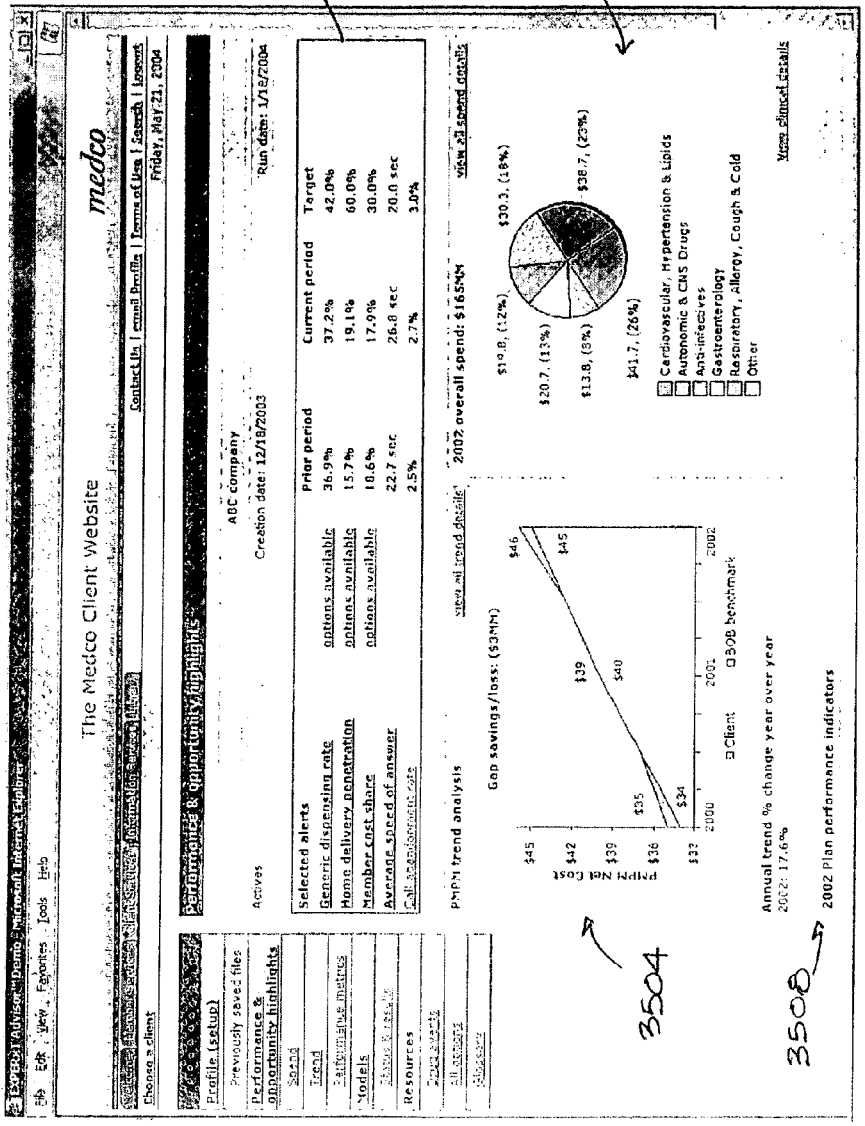
FIG. 35 is an illustrative performance and opportunity highlights screen that may be provided by the prescription drug spend and trend application in accordance with some embodiments of the present invention.

Once a client profile has been created, the user may advantageously be provided with a screen summarizing the spend and trend analysis performed by the application. FIG. 35 is an illustrative performance and opportunity highlights screen 3500 that may be provided by the prescription drug spend and trend application in accordance with some embodiments of the present invention. Screen 3500 may also be referred to generally as a "client dashboard," in that it provides an overview of a client's prescription drug plan. In particular, screen 3500 includes an alerts region 3502 in which any performance alerts for the plan are provided. Performance alerts that do not fall within the specified target (as shown, for example, in FIGS. 29 and 30) may be provided in a different color than those that do fall within the target zone. For example, alerts region 3502 may provide alerts in red to attract the user's attention to the fact that the target is not being met. Screen 3500 may include a trend analysis region 3504. As shown, trend analysis region depicts the client's growth compared to a selected peer or industry group. This benchmarking comparison may be selected, for example, in option 2802 of screen 2800 (FIG. 28). Screen 3500 may include a spend analysis region 3506 that includes a depiction of spend as broken down into particular components. For example, as shown in spend analysis region 3506, spend has been broken down into components based on therapeutic drug classes. Screen 3500 may include a plan performance statistics region 3508 (not completely shown) to provide performance indicators that a user may monitor to gauge plan performance.

Figure 36:
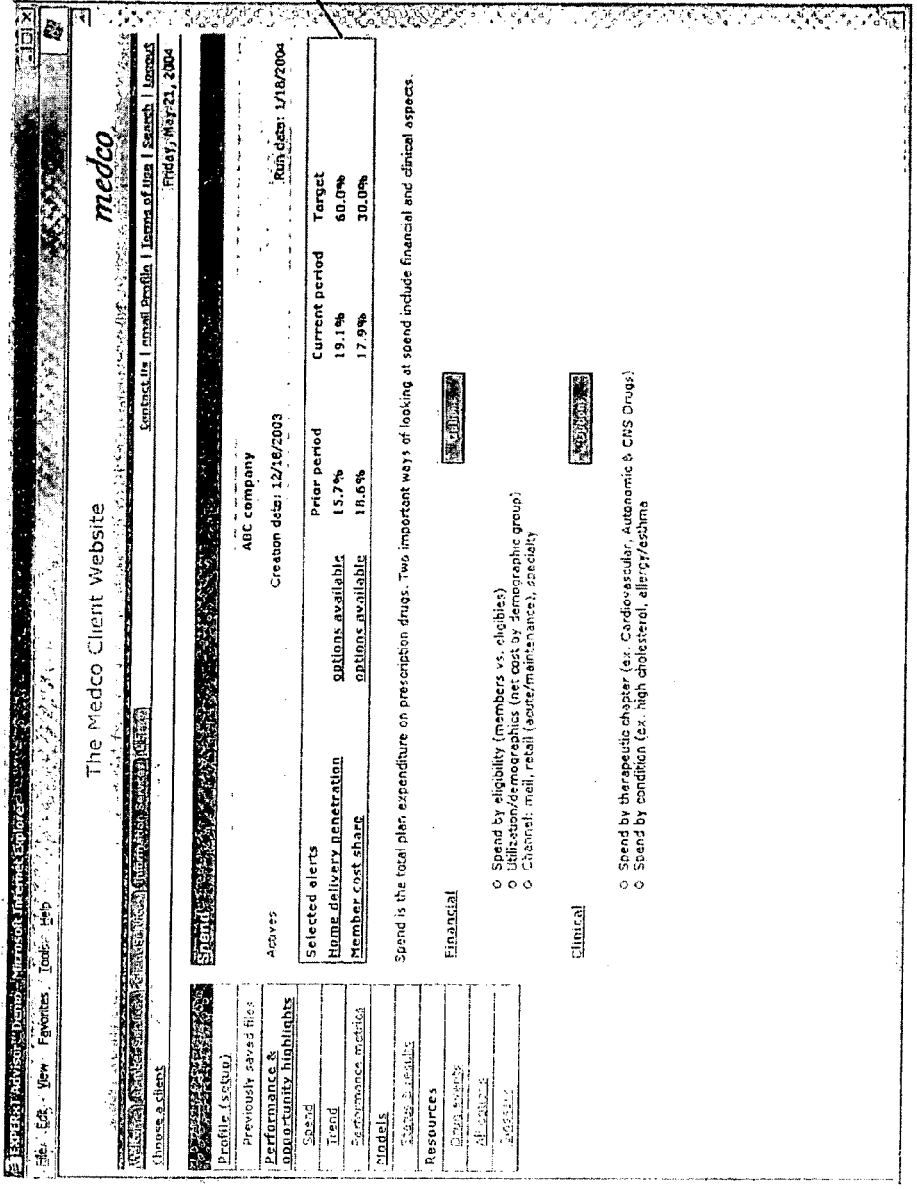
Figure 37:
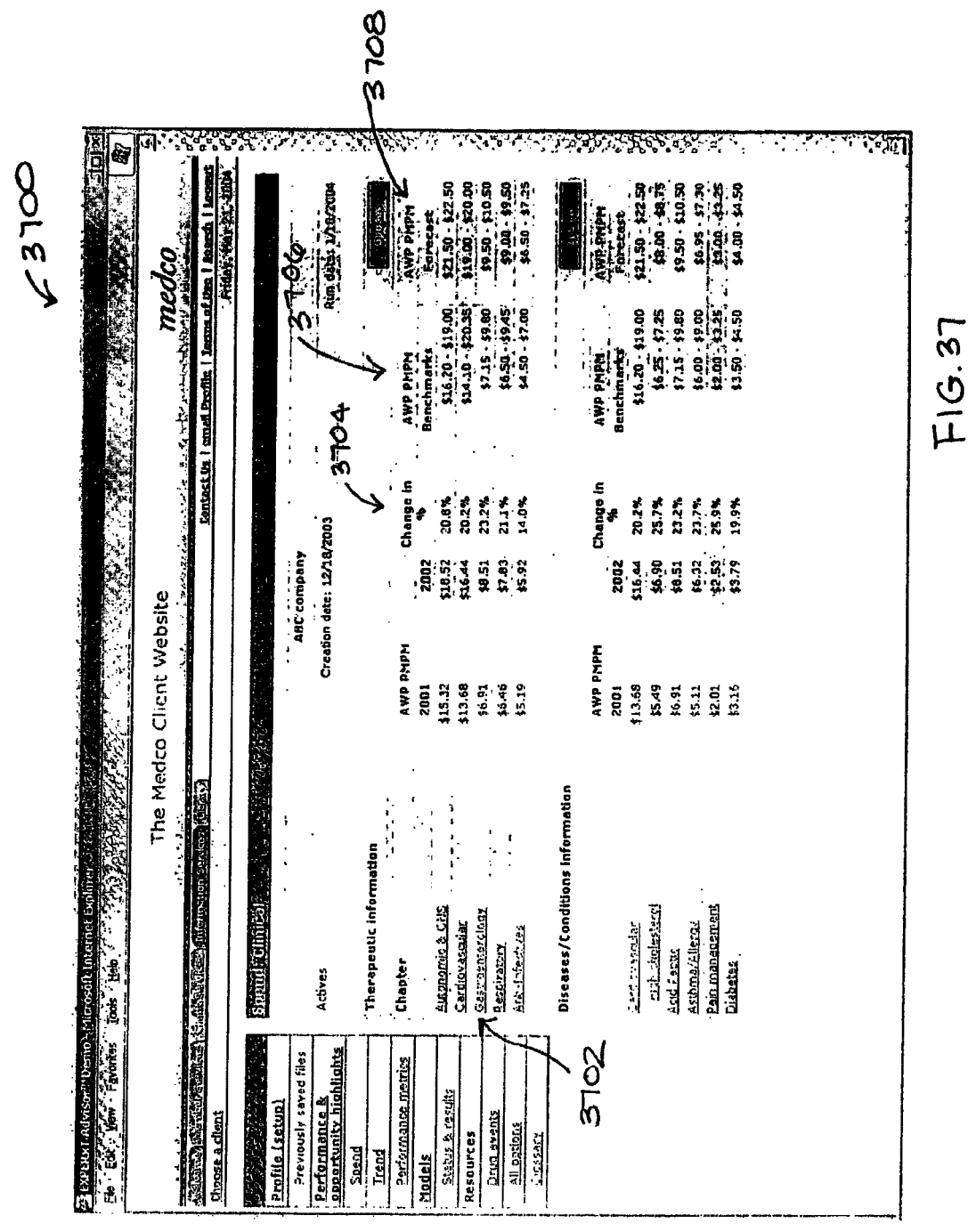
Figure 38:
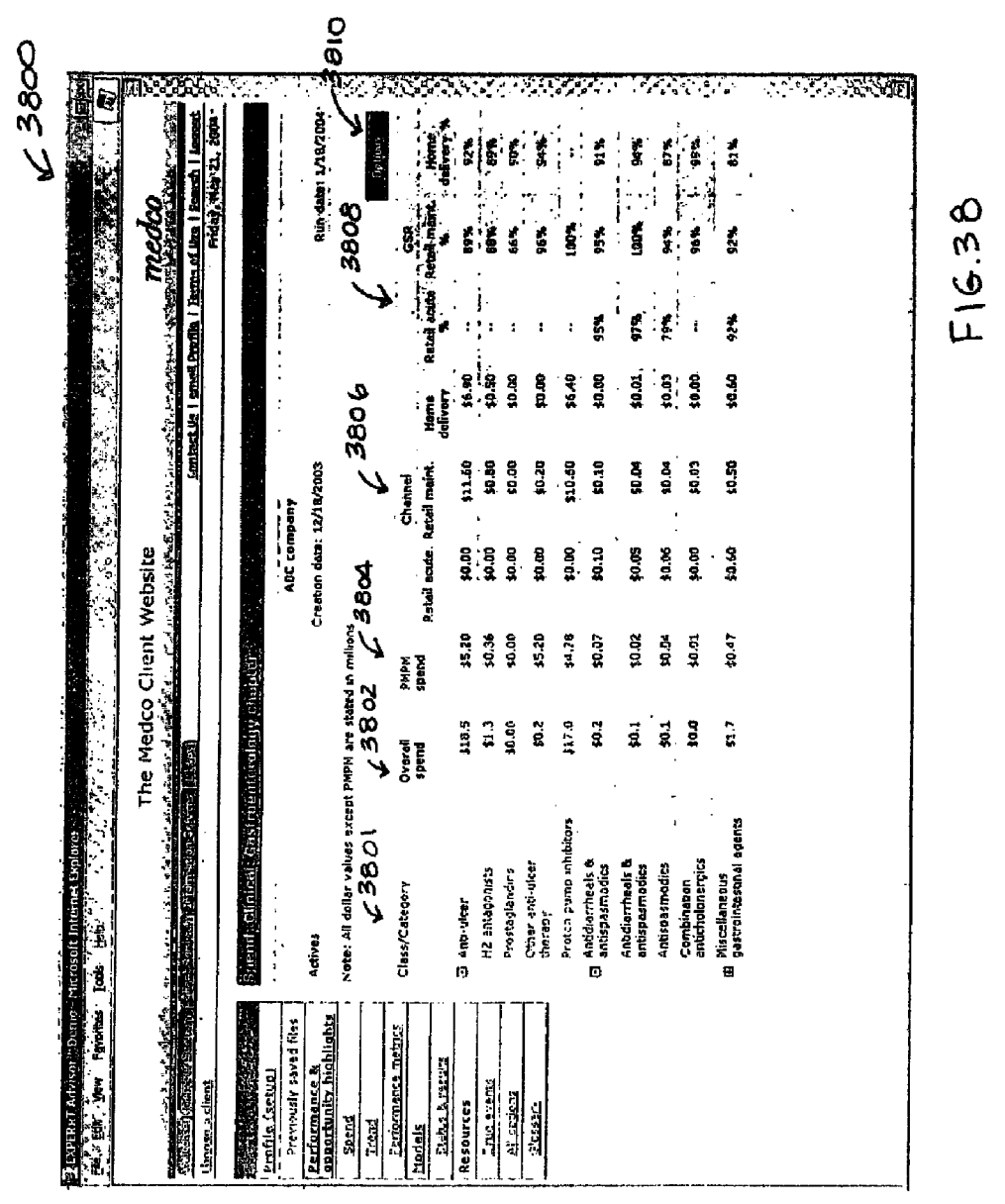

As shown in screen 3500, a user may view additional information in connection with the drug spend for the prescription drug plan. FIGS. 36-38 are illustrative prescription drug plan spend information screens that may be provided by the prescription drug spend and trend application in accordance with some embodiments of the present invention. Screen 3600 of FIG. 36 allows the user to drill down into financial or clinical aspects of the drug spend for the plan.

Performance metrics and alerts that have the greatest influence on spend may be carried over from screen 3500 and provided on screen 3600 in region 3602. If an option is available in connection with a particular metric, region 3602 may indicate this (e.g., "options available"). If the user selects, for example, the "Clinical" aspect of spend for further review, the user may be provided with screen 3700 of FIG. 37.

Screen 3700 is an illustrative drug spend screen demonstrating drug spend by therapeutic chapter, corresponding to the pie chart in region 3506 of screen 3500, as well as by disease/condition. Disease/condition is a data element that captures spend in terms of the cost for drugs used to treat a particular disease or condition. It should be noted that the diseases/conditions and therapeutic drug chapters provided in screen 3700 are merely illustrative, and any suitable diseases/conditions, therapeutic drug chapters, or other suitable clinical information may be provided in connection with a prescription drug plan's spend. As shown in screen 3700, drug spend for a particular disease/condition or therapeutic chapter may be provided as the average wholesale price ("AWP") per member per month ("PMPM"). A metric such as the AWP may be used to provide valid benchmarking, eliminating variables such as cost share from the drug spend calculation. Screen 3700 provides the percentage change in drug spend in column 3704, which in the example of FIG. 37 is the change in spend from 2001 to 2002. Screen 3700 provides benchmarking values in column 3706 for comparison of the client's prescription drug plan to a benchmark (e.g., book of business, peers, etc.). Screen 3700 provides a forecast column 3708 to provide an approximate range for future drug spend based on present values.

To review additional detail for a particular component of drug spend, a user may select the particular component of drug spend using any suitable user input device. In screen 3700, for example, the gastroenterology component 3702 of drug spend has increased by 23% from 2001 to 2002, as indicated in column 3704. To view additional detail on this increase, a user may select "Gastroenterology" component 3702. In response to the user's selection, the spend and trend application may provide the user with screen 3800 of FIG. 38.

Screen 3800 is an illustrative drug spend screen that provides additional detail on drug spend for gastroenterology drugs in accordance with some embodiments of the present invention. Screen 3800 may include a class/category column 3801 that provides a list of particular classes or categories of gastroenterological drugs contributing to the plan's drug spend. Screen 3800 may include both an overall spend column 3802 and a per member per month column spend 3804. Screen 3800 may include channel region 3806, which provides a breakdown of the costs behind particular channels of distribution. As shown in FIG. 38, region 3806 includes the cost for retail acute, retail maintenance, and home delivery components for channel of distribution. Screen 3800 may include a generic substitution rate ("GSR") region 3808, which provides a breakdown of the GSR for each of the channels of distribution provided in the screen. From screen 3800, a user may be provided with the ability to determine whether there are solutions, or options, specific to the prescription drug plan for improving gastroenterological spend. For example, a user may select "options" button 3810 to review any options available. In response to the selection of button 3810, the rules engine of the spend and trend application may be initiated, and a screen providing a list of client-specific solutions targeted to the identified issue may be provided.

Figure 39:
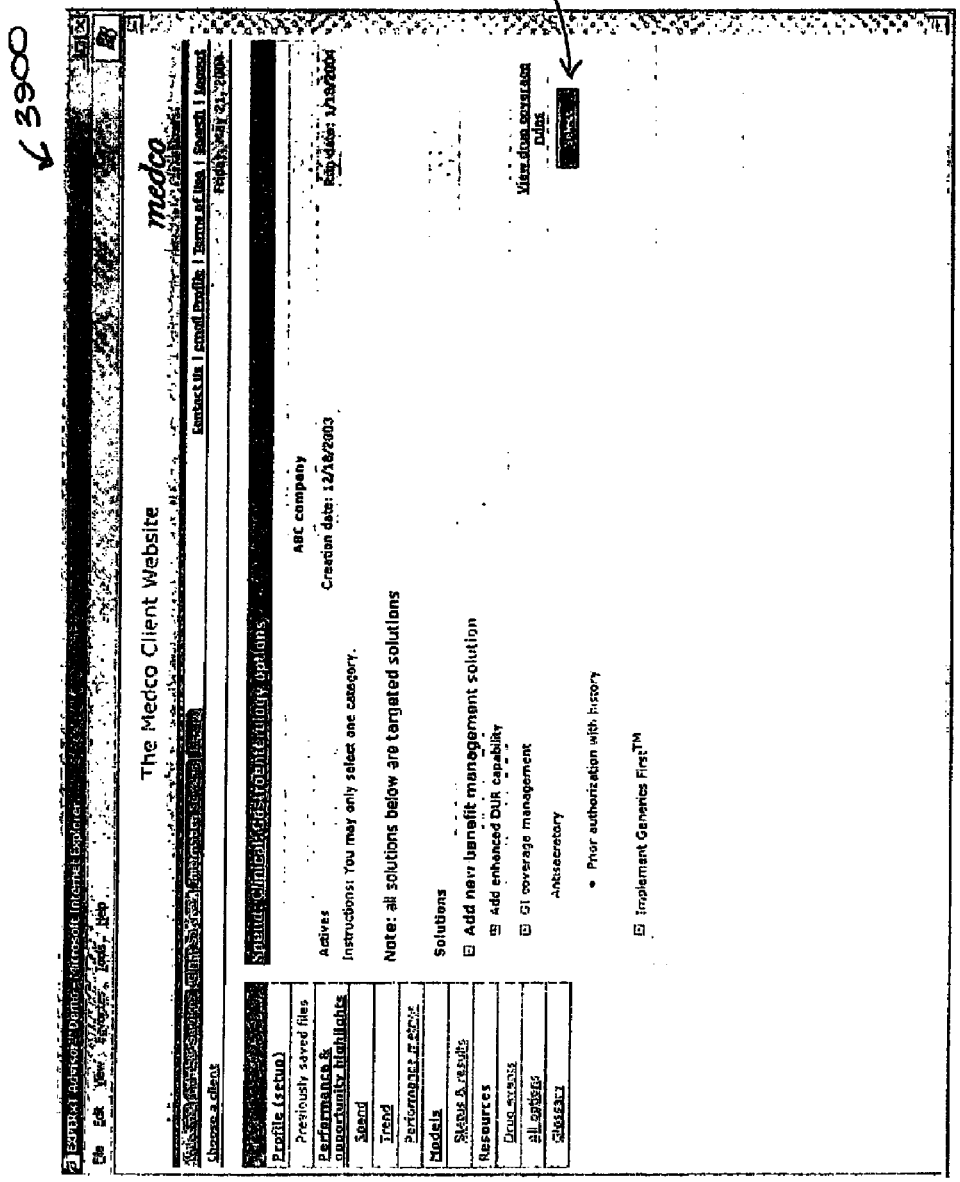
FIG. 39 is an illustrative prescription drug plan spend option screen that may be provided by the prescription drug spend and trend application in accordance with some embodiments of the present invention.

FIG. 39 is an illustrative prescription drug plan spend option screen 3900 that may be provided by the prescription drug spend and trend application in accordance with some embodiments of the present invention. In screen 3900, a user is provided with the ability to drill down to solutions, or options, addressing the plan's gastroenterological drug spend. As shown, the option "Prior authorization with history" as it applies to antisecretory drugs is provided. In response to the selection of button 3902, the spend and trend application may provide a screen that enables the user to model the impact of the option on the plan.

Figure 40:
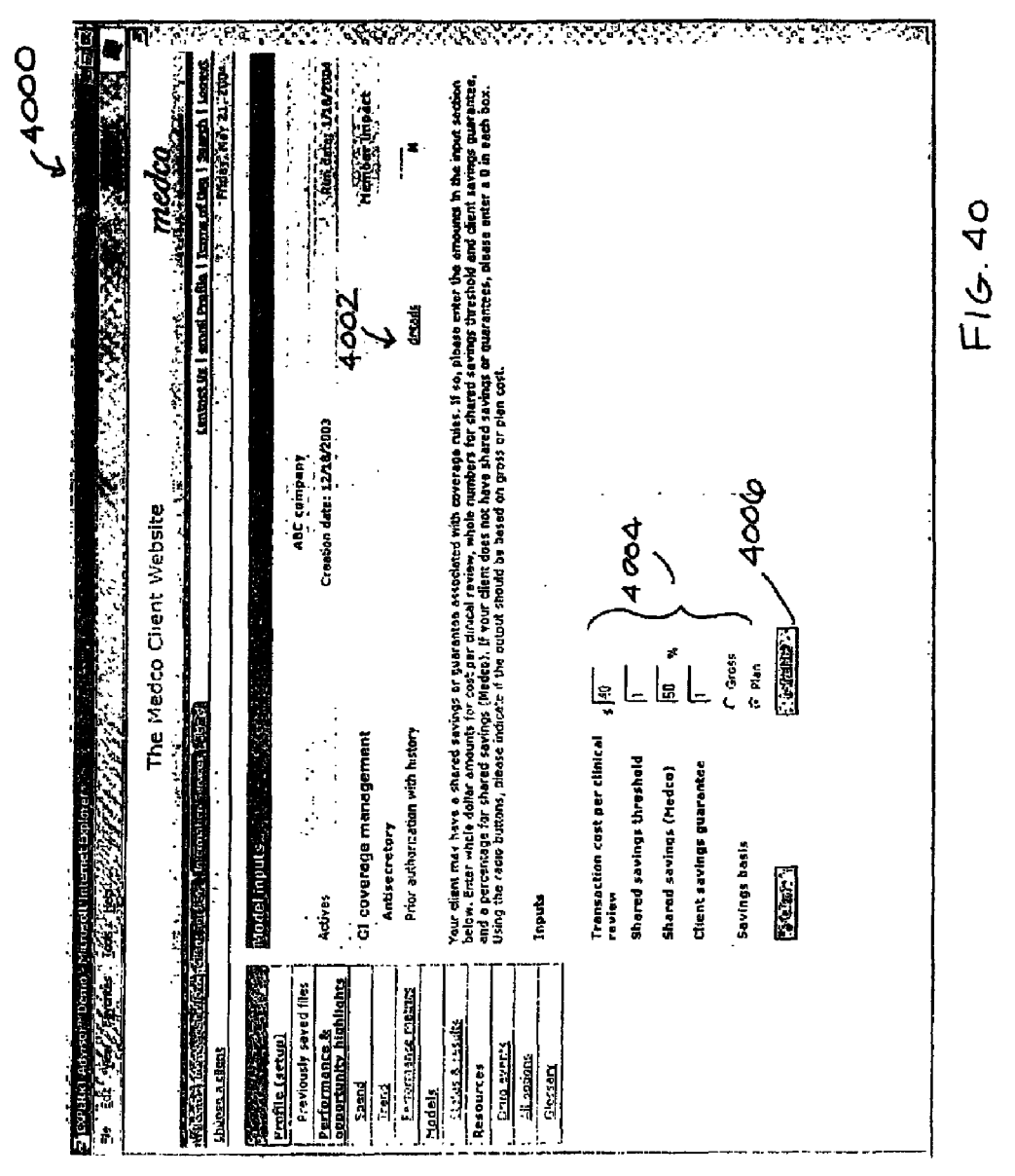
Figure 41:
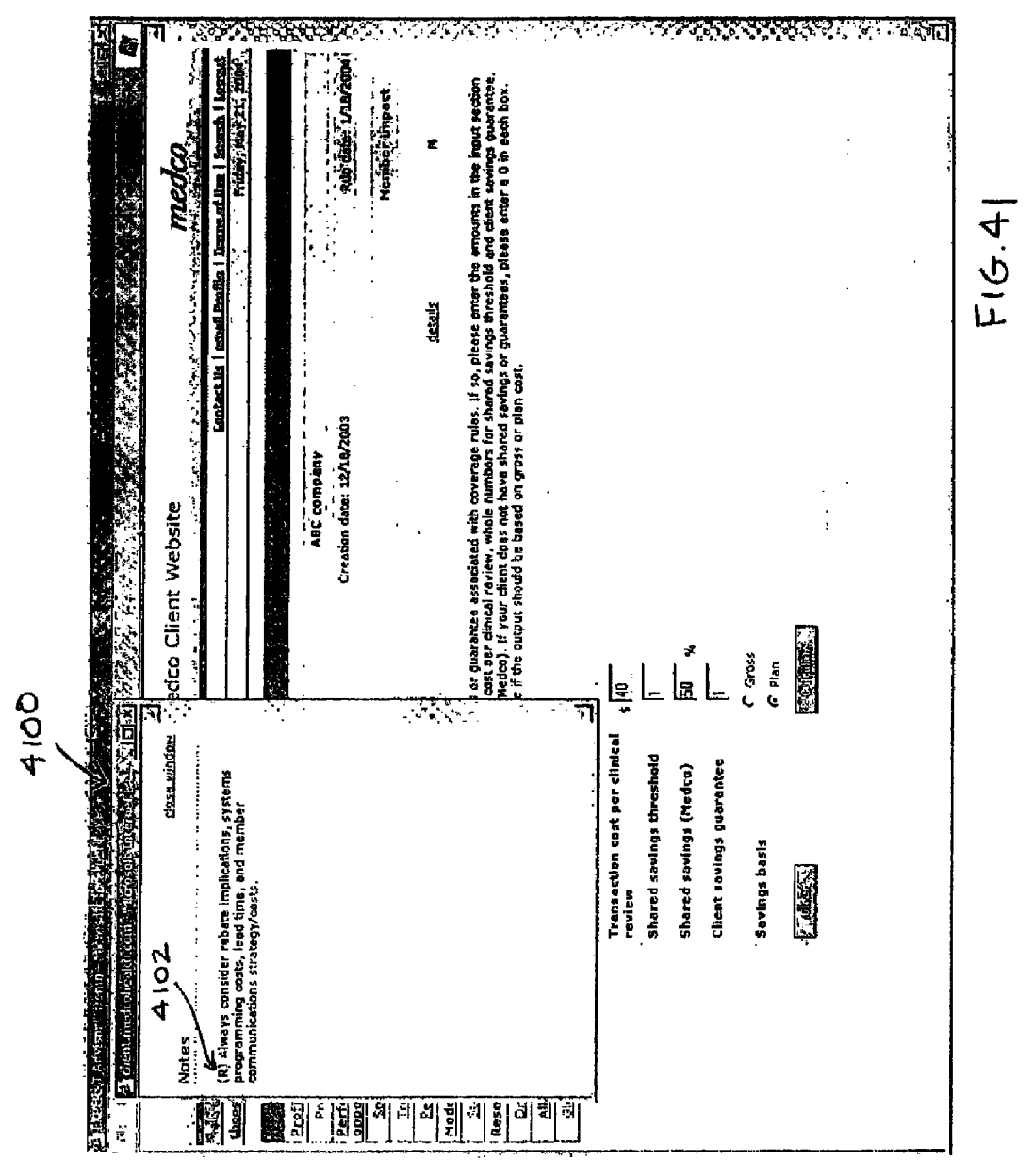

FIG. 40 is an illustrative model inputs screen 4000 for a prescription drug plan spend option that may be provided by the prescription drug spend and trend application in accordance with some embodiments of the present invention. Screen 4000 allows a user to enter inputs in connection with modeling the impact of the "Prior authorization with history" option selected in screen 3900 (FIG. 39). To obtain additional details in connection with the selected option, a user may select "details" link 4002. In response to the selection of "details" link 4002, the spend and trend application may provide the user with overlay 4100 of FIG. 41. Overlay 4100 provides the user with information in connection with the option. In this example, overlay 4100 provides the user with reminders of what to consider in implementing the selected option (e.g., rebate implications, systems programming costs, lead time, member communications strategy/costs). Overlay 4100 may include an icon 4102 that indicates the impact of implementing the selected solution on the pharmacy benefit provider's margin. Icon 4102 may be, for example, color-coded to visually indicate the impact of the option on the provider's margin (e.g., green indicating no impact, yellow indicating a possible impact, and red indicating an adverse impact).

Referring back to FIG. 40, the user may provide model inputs in fields 4004 to tailor the modeling of the option's impact to the particular prescription drug plan. To calculate the impact of the model, the user may select "Calculate" button 4006. In response to the selection of button 4006, the spend and trend application may provide the user with a summary of the modeling results.

FIG. 42 is an illustrative model output screen 4200 for a prescription drug plan spend option that may be provided by the prescription drug spend and trend application in accordance with some embodiments of the present invention. As shown, screen 4200 may include an inputs region 4202 that provides a summary of the inputs provided by the user in region 4004 of screen 4000 (FIG. 40). Screen 4200 may include an outputs region 4204 that includes the results of the application of the model to the prescription drug plan. Outputs region 4204 may include, for example, the gross cost, cost share, plan cost, PMPM, POS attrition rate, clinical review rate, clinical review denial rate, and total denial rate. It should be noted that these outputs are merely illustrative, and the spend and trend application may provide the impact of the proposed change on some, all, or alternative aspects of a prescription drug plan. Screen 4200 may include a member impact region 4206, which indicates the number of plan members that may be impacted by the proposed change. In this example, member impact region 4206 indicates that 632 members will be impacted if the proposed change is made. From screen 4200, the user may add the output of the model application to a summary maintained, for example, in information warehouse 310 (FIG. 3). In response to the selection of "Add to summary" button 4208, the spend and trend application may store the modeling results and provide the user with a summary screen.

Figure 43:
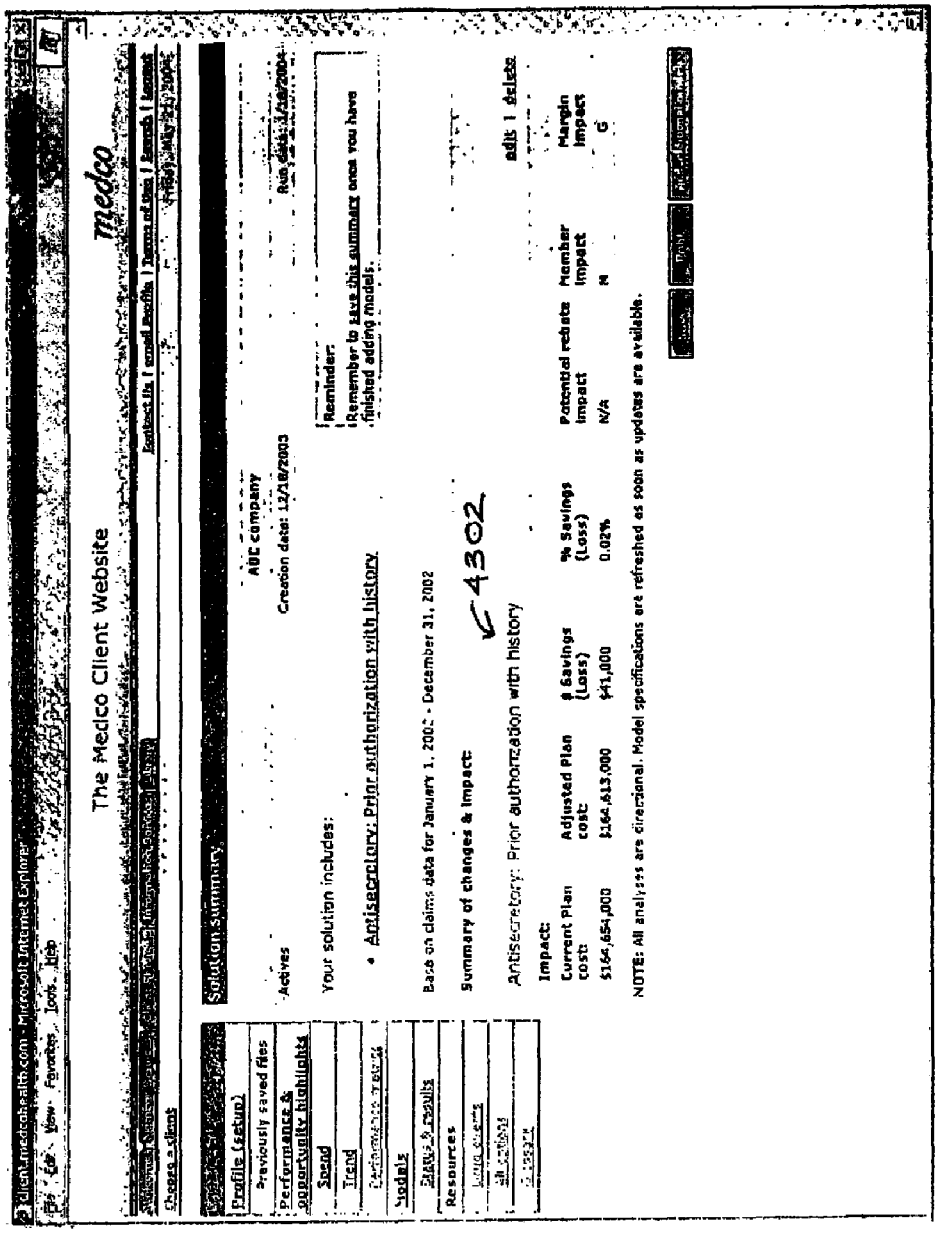
FIG. 43 is an illustrative model output solution summary screen for a prescription drug plan spend option that may be provided by the prescription drug spend and trend application in accordance with some embodiments of the present invention.

FIG. 43 is an illustrative model output solution summary screen 4300 for a prescription drug plan spend option that may be provided by the prescription drug spend and trend application in accordance with some embodiments of the present invention. As shown, screen 4300 may include a region 4302 that provides a summary of the modeling of "Prior authorization with history" option. Region 4302 may include a portion of the outputs provided in output region 4204 of screen 4200 (FIG. 42). If a user models the impact of additional changes to the prescription drug plan, screen 4300 may be updated to include the output for those additional models.

Figure 44:
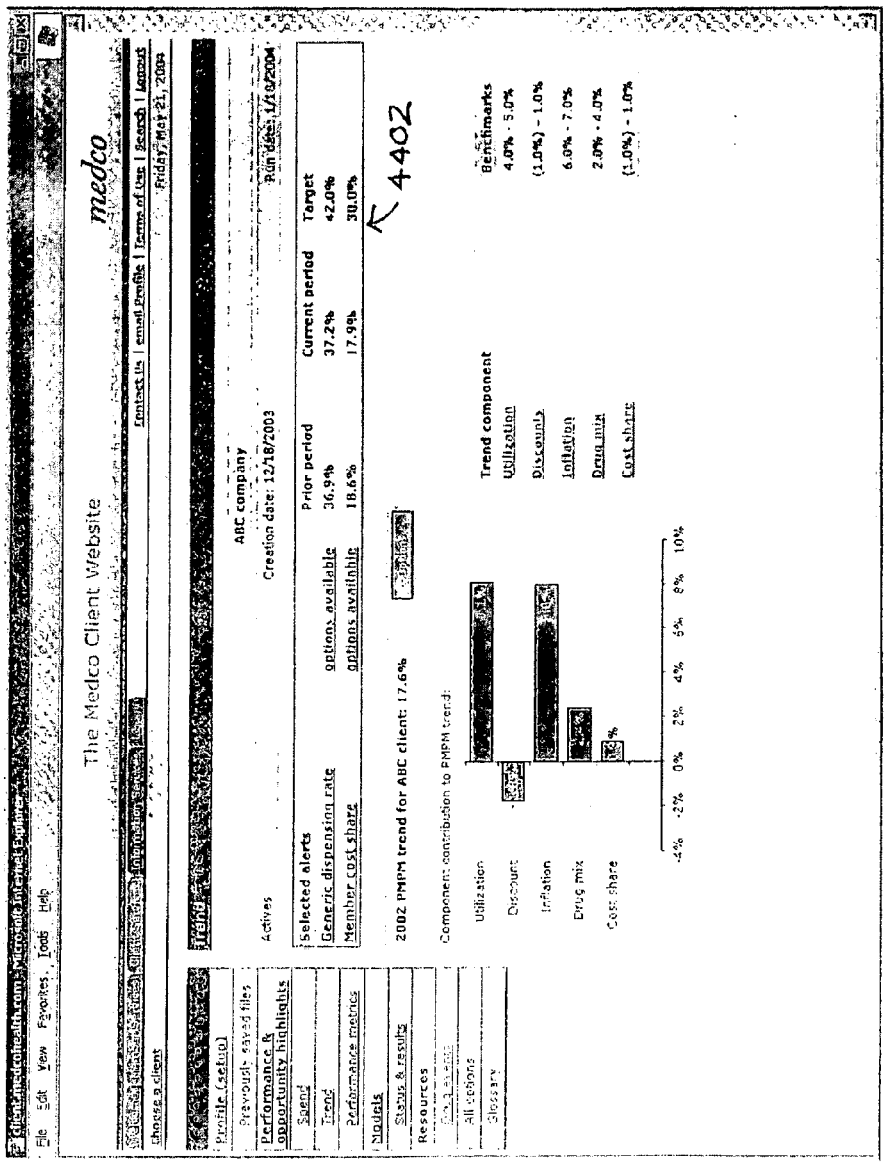
FIGS. 44 and 45 are illustrative prescription drug plan trend information screens that may be provided by the prescription drug spend and trend application in accordance with some embodiments of the present invention.
Figure 45:
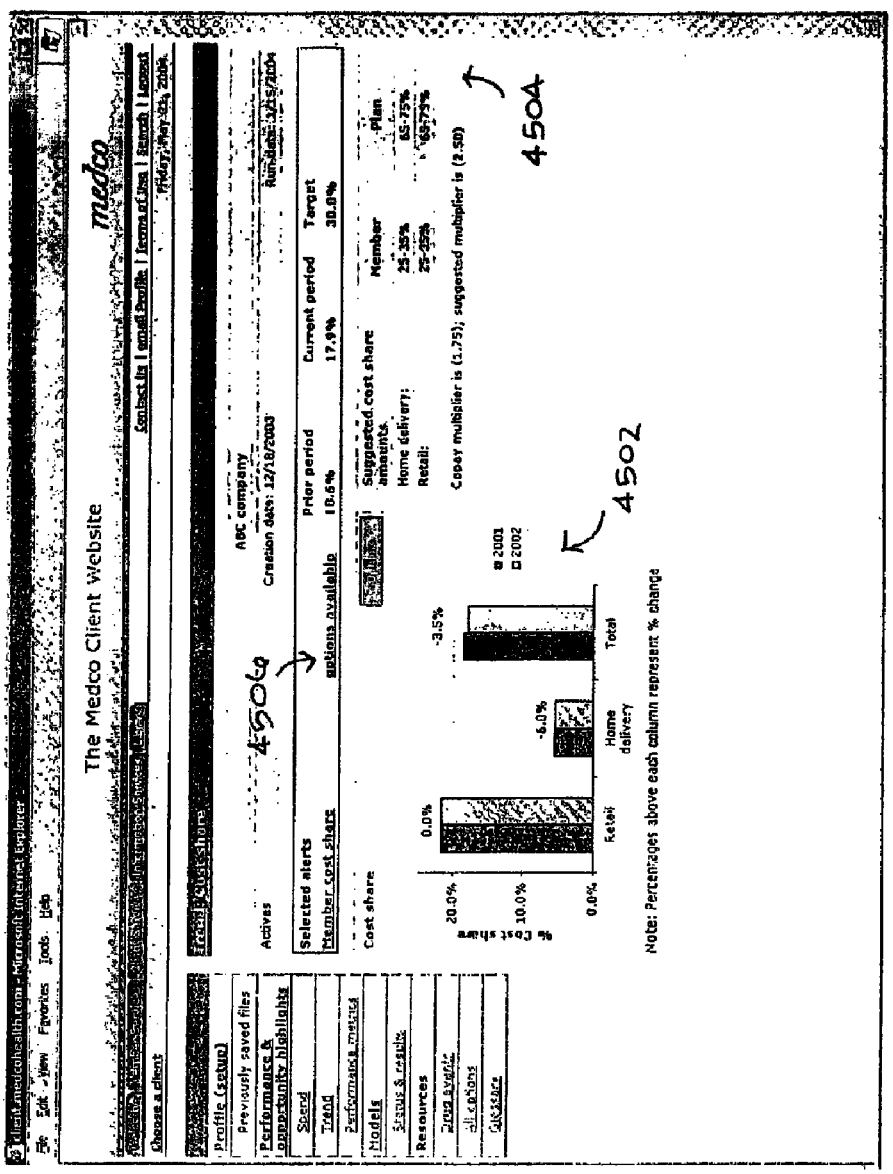

Referring back to FIG. 35, performance and opportunity highlights screen 3500, also referred to herein as a client dashboard, provides an overview of a client's prescription drug plan. As described hereinabove, screen 3500 may include a trend analysis region 3504. As shown, trend analysis region depicts the client's growth compared to a select peer or industry group. As shown in screen 3500, a user may view additional information in connection with the drug trend for the prescription drug plan. FIGS. 44 and 45 are illustrative prescription drug plan trend information screens that may be provided by the prescription drug spend and trend application in accordance with some embodiments of the present invention. Screen 4400 of FIG. 44 provides the detail behind a client's per member per month trend and allows the user to determine the primary drivers, or components, of trend. Performance metrics and alerts that have the greatest influence on trend may be carried over from screen 3500 (FIG. 35) and provided on screen 4400 in region 4402. If an option is available in connection with a particular metric, region 4402 may indicate this (e.g., "options available"). If the user selects, for example, the "Member cost share" aspect of spend for further review, the user may be provided with screen 4500 of FIG. 45.

Screen 4500 is an illustrative drug trend screen providing a member cost share comparison broken down by channels of distribution. As shown in this example, cost share region 4502 may include a bar graph demonstrating the cost share in years 2001 and 2002, broken down by retail and home delivery channels of distribution. In region 4504, the application indicates suggested cost share amounts for home delivery and retails channels, both per member and per plan. Screen 4500 may include an indication that options are available for improving member cost share. The user may select "options available" link 4506 to review available options. In response to the user's selection of link 4506, the rules engine of the spend and trend application may be initiated and a screen that includes a list of client-specific solutions targeted at the identified issue may be provided.

Figure 46:
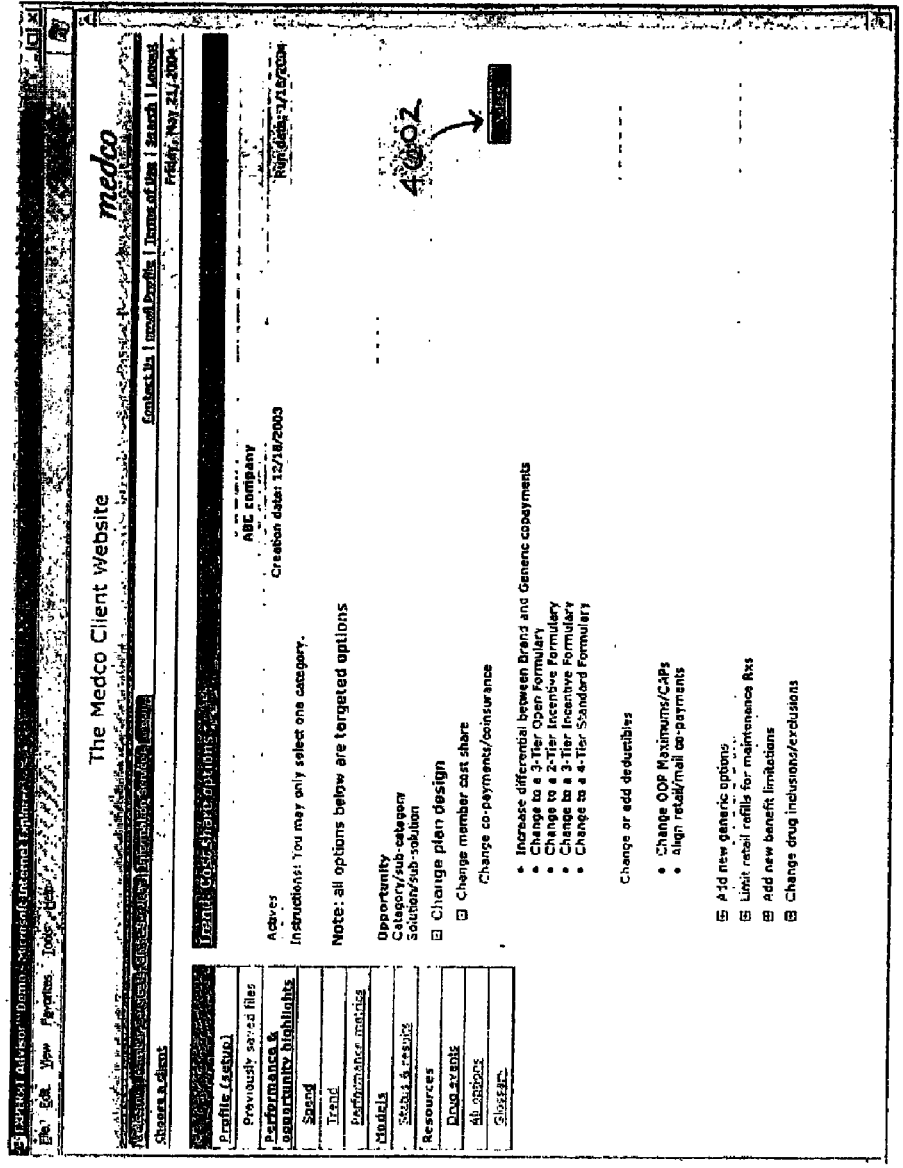
FIG. 46 is an illustrative prescription drug plan trend option screen that may be provided by the prescription drug spend and trend application in accordance with some embodiments of the present invention.

FIG. 46 is an illustrative prescription drug plan trend option screen 4600 that may be provided by the prescription drug spend and trend application in accordance with some embodiments of the present invention. In screen 4600, a user is provided with the ability to drill down to solutions, or options, addressing the plan's member cost share trend. As shown, the option "Change co-payments/coinsurance" as it applies to member cost share is provided. In response to the selection of button 4602, the user may be provided with a screen that enables the user to model the impact of the option on the plan.

Figure 47:
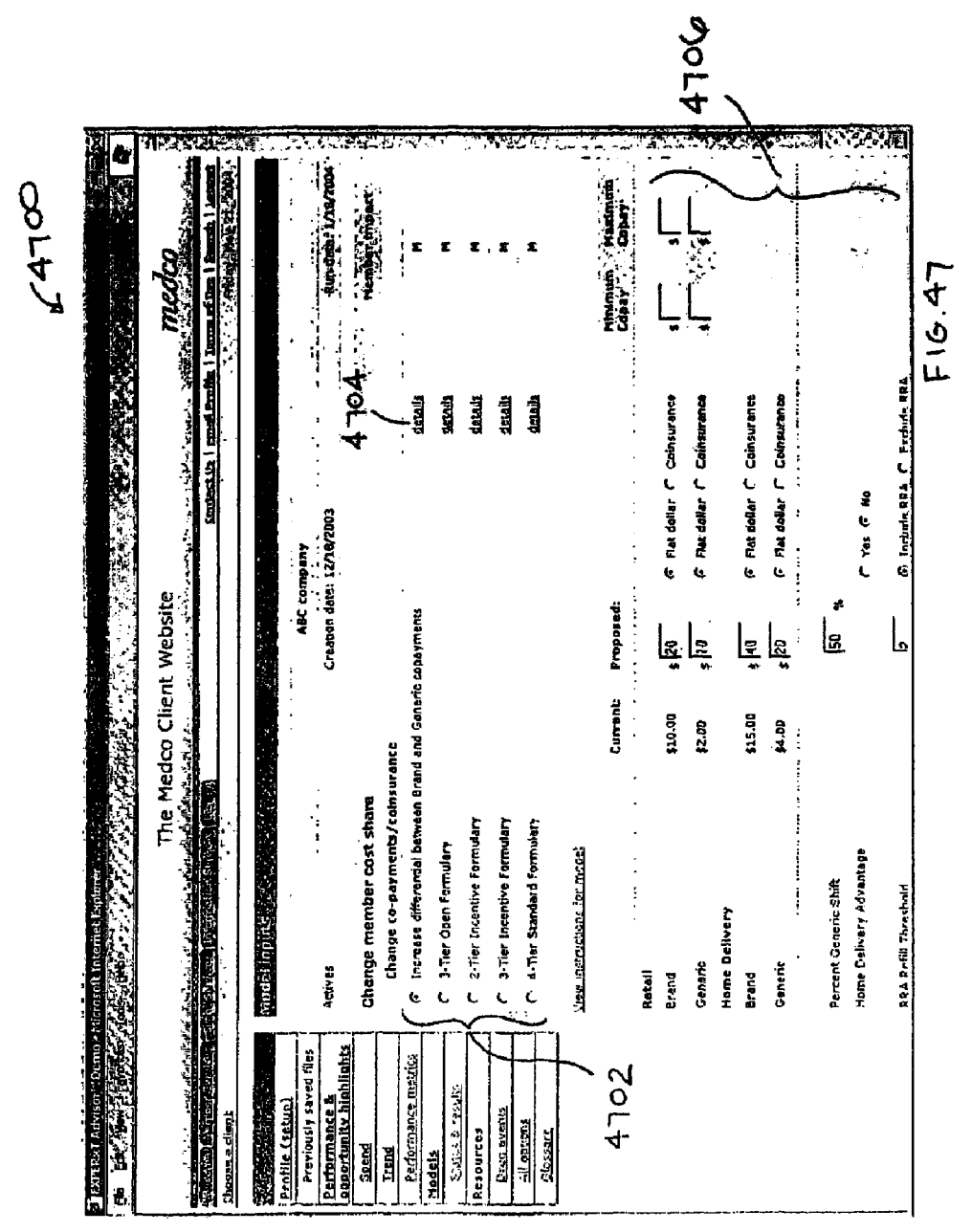
Figure 48:
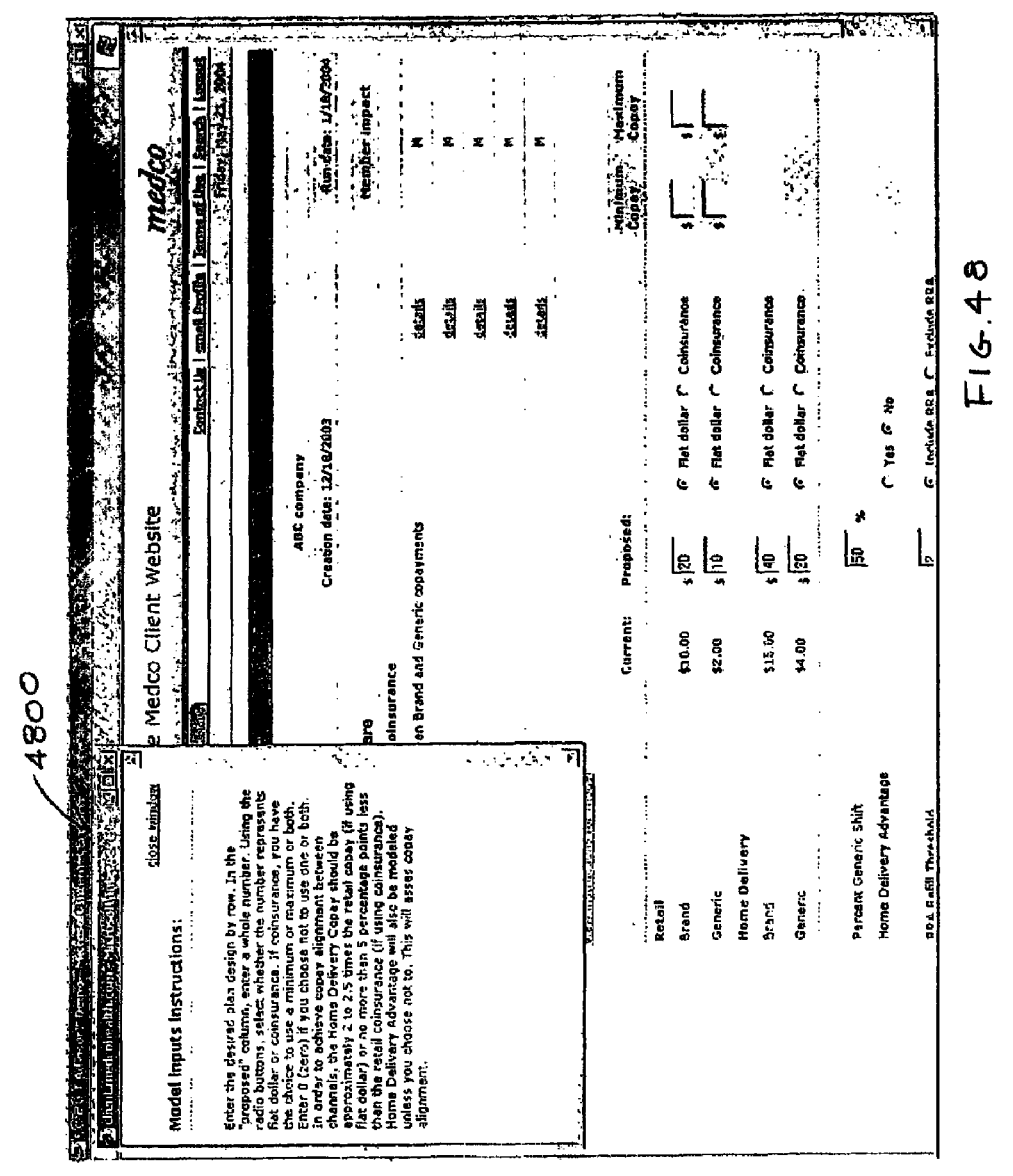

FIG. 47 is an illustrative model inputs screen 4700 for a prescription drug plan trend option that may be provided by the prescription drug spend and trend application in accordance with some embodiments of the present invention. Screen 4700 allows a user to enter inputs in connection with modeling the impact of the "Change co-payments/coinsurance" option selected in screen 4600 (FIG. 46). As shown, screen 4700 includes a plurality of sub-options 4702 in connection with the "Change co-payments/coinsurance" option. In this example, the user has selected sub-option "Increase differential between Brand and Generic co-payments." To obtain additional details in connection with the selected option, a user may select "details" link 4704. In response to the selection of "details" link 4704, the spend and trend application may provide the user with overlay 4800 of FIG. 48. Overlay 4800 provides the user with information in connection with the option. In this example, overlay 4800 provides the user with model inputs instructions.

Referring back to FIG. 47, the user may provide model inputs in fields 4706 to tailor the modeling of the option's impact to the client's prescription drug plan. To calculate the impact of the model, the user may select, for example, a "Calculate" button (not shown in this portion of screen 4700). In response to the selection of the "Calculate" button, the spend and trend application may provide the user with a summary of the modeling results.

FIG. 49 is an illustrative model output screen 4900 for a prescription drug plan trend option that may be provided by the prescription drug spend and trend application in accordance with some embodiments of the present invention. As shown, screen 4900 may include an inputs region 4902 that provides a summary of the inputs provided by the user in region 4706 of screen 4700 (FIG. 47). Screen 4900 may include an outputs region 4904 that includes the results of the application of the model to the prescription drug plan. The outputs may include, for example, the gross cost, cost share, plan cost, and PMPM. It should be noted that these outputs are merely illustrative, and the spend and trend application may provide the impact of the proposed change on some, all, or alternative aspects of a prescription drug plan. From screen 4900, the user may add the modeling output to a summary maintained, for example, in information warehouse 310 (FIG. 3). In response to the selection of "Add to summary" button 4906, the spend and trend application may store the modeling results and provide the user with a summary screen.

Figure 50:
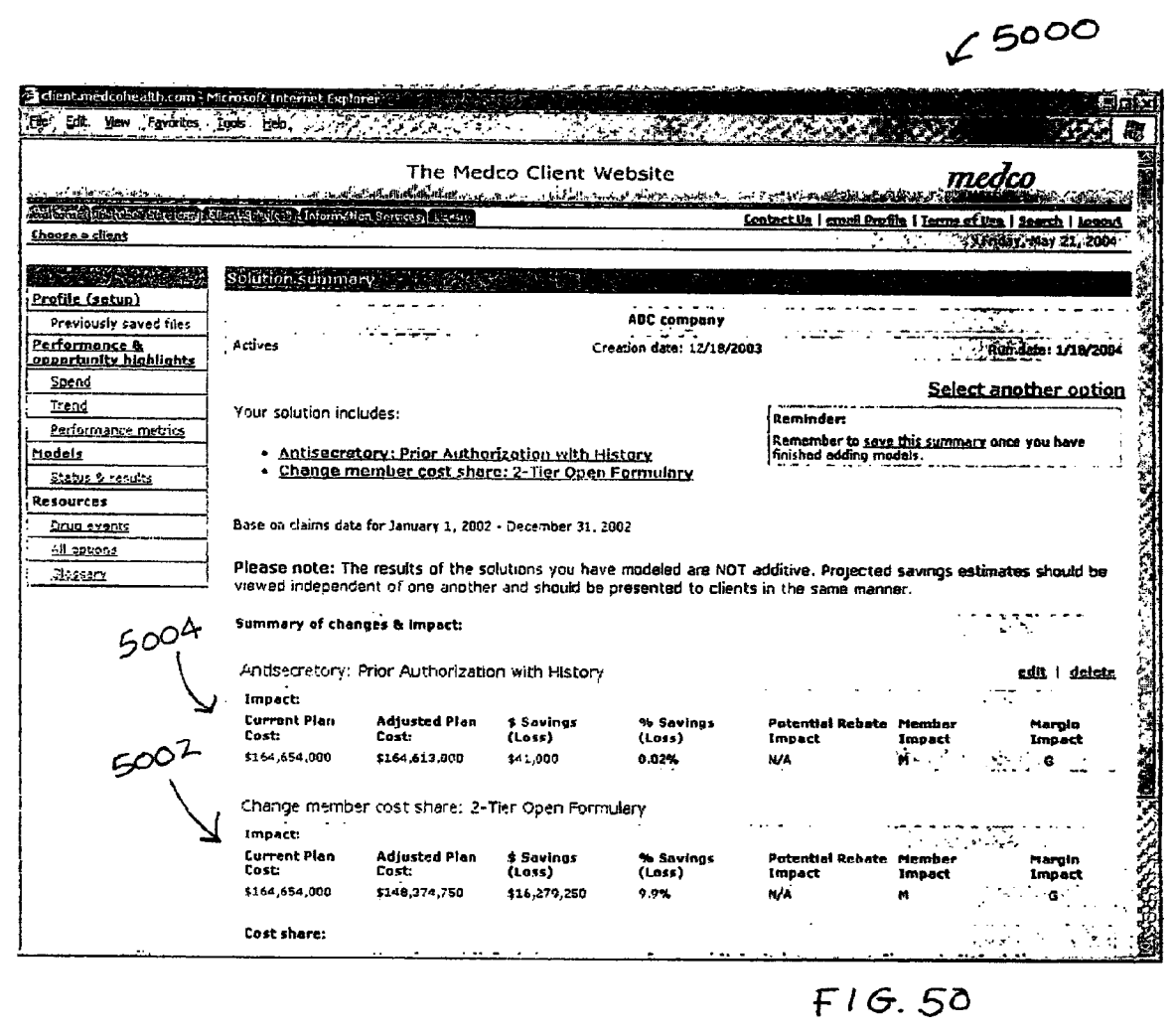

FIG. 50 is an illustrative model output solution summary screen 5000 for a prescription drug plan trend option that may be provided by the prescription drug spend and trend application in accordance with some embodiments of the present invention. As shown, screen 5000 may include a region 5002 that provides a summary of the "Change member cost share: 2-Tier Open Formulary" trend option. Region 5002 may include a portion of the outputs provided in output region 4906 of screen 4900 (FIG. 49). As described hereinabove in connection with screen 4300 of FIG. 43, screen 5000 may include the output for additional modeling results. As shown, screen 5000 may include region 5004 that provides a summary of the modeling of "Antisecretory: Prior Authorization with History" spend option, which was previously modeled by the spend and trend application.

As described hereinabove, the spend and trend application of the present invention provides a user with the ability to model the impact of a proposed option on a client's prescription drug plan. Alternatively, or in addition thereto, the spend and trend application may provide a user with access to a plurality of models, from which the user may select a model to be applied to the client's prescription drug plan.

Figure 51:
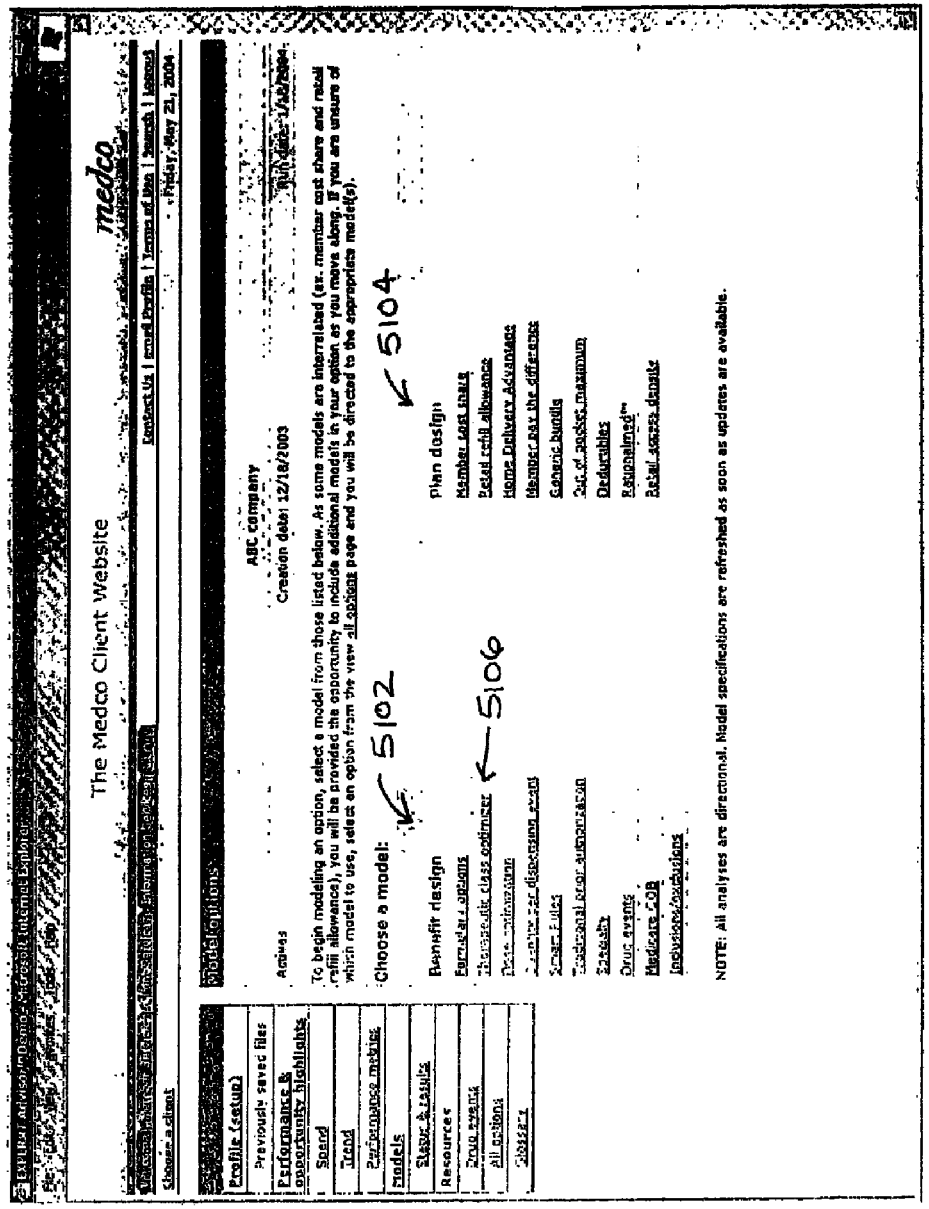
FIG. 51 is an illustrative prescription drug plan models screen that may be provided by the prescription drug spend and trend application in accordance with some embodiments of the present invention.

FIG. 51 is an illustrative prescription drug plan models screen 5100 that may be provided by the prescription drug spend and trend application in accordance with some embodiments of the present invention. Screen 5100 may include models that apply to both benefit design 5102 and plan design 5104. It should be noted that the models and model categorizations (e.g., plan design and benefit design) provided in screen 5100 are merely illustrative, and the spend and trend application of the present invention may provide a user with access to any suitable model for application to a prescription drug plan. If a user selects a particular model from screen 5100, the spend and trend application may provide the user with a model inputs screen similar to those provided in FIGS. 40 and 47. In this example, if the user selects "Therapeutic class optimizer" option 5106, then the application may provide the user with a model inputs screen in connection with that option.

Figure 52A:
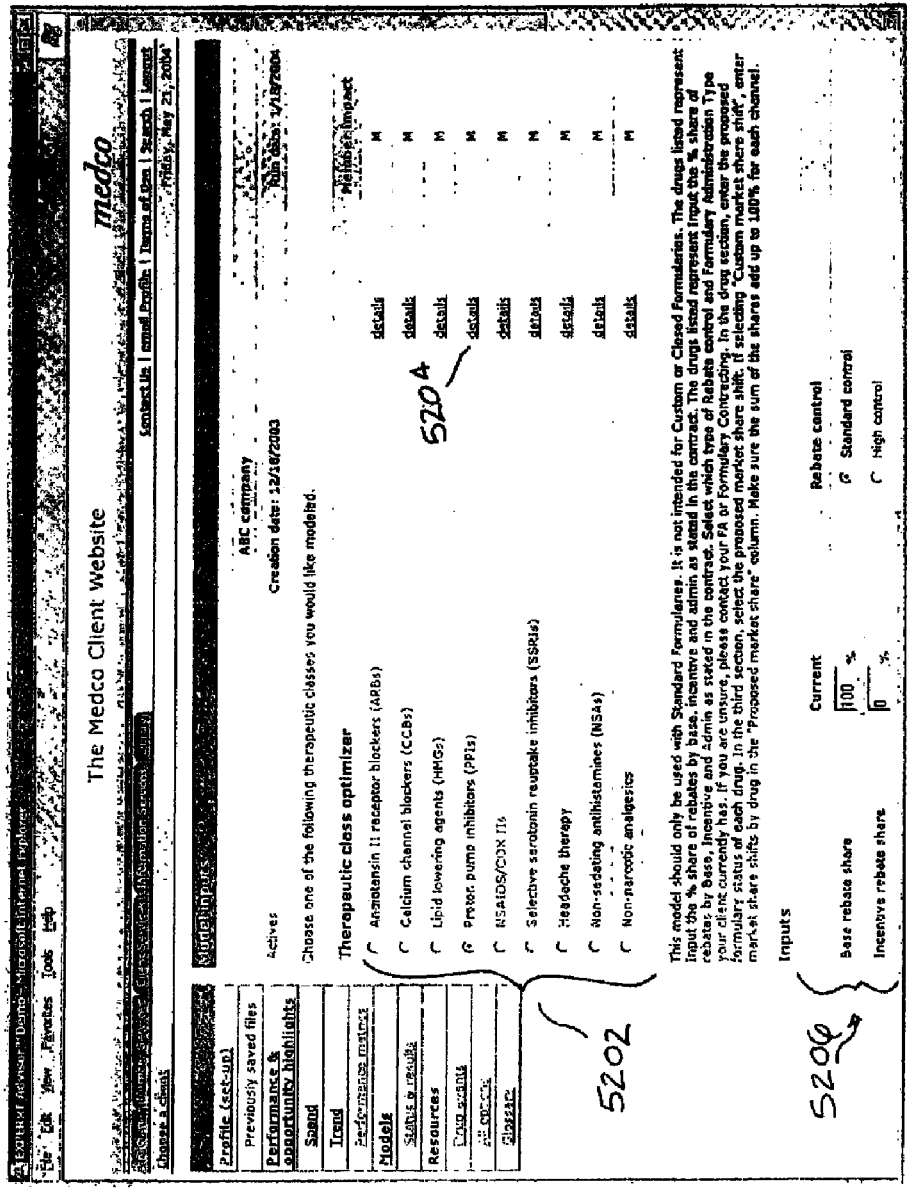

FIGS. 52A and 52B are portions of an illustrative prescription drug plan model selection and input screen 5200 that may be provided by the prescription drug spend and trend application in accordance with some embodiments of the present invention. Screen 5200 allows a user to enter inputs in connection with modeling the impact of "Therapeutic class optimizer" option 5106 selected in screen 5100 (FIG. 51). As shown, screen 5200 includes a plurality of sub-options 5202 in connection with "Therapeutic class optimizer" option 5106. In this example, the user has selected sub-option "Proton pump inhibitors (PPIs)." To obtain additional details in connection with the selected option, a user may select "details" link 5204. In response to the selection of "details" link 5204, the spend and trend application may provide the user with an overlay substantially similar to those described hereinabove in connection with overlay 4100 of FIG. 41 or overlay 4800 of FIG. 48. The user may provide model inputs in fields 5206 to tailor the modeling of the option's impact to the client's prescription drug plan.

To calculate the impact of the option (e.g., to apply the appropriate model to the plan), the user may select "Calculate" button 5208. In response to the selection of "Calculate" button 5208, the spend and trend application may provide the user with a summary of the modeling results. This summary screen may be substantially similar to the model output screens described hereinabove (e.g., screen 4200 of FIG. 42 and screen 4900 of FIG. 49). Also as described hereinabove, the output of the model application may be added to a summary maintained, for example, in information warehouse 310 (FIG. 3) (see, for example, summary screen 4300 of FIG. 43 and summary screen 5000 of FIG. 50).

Figure 53:
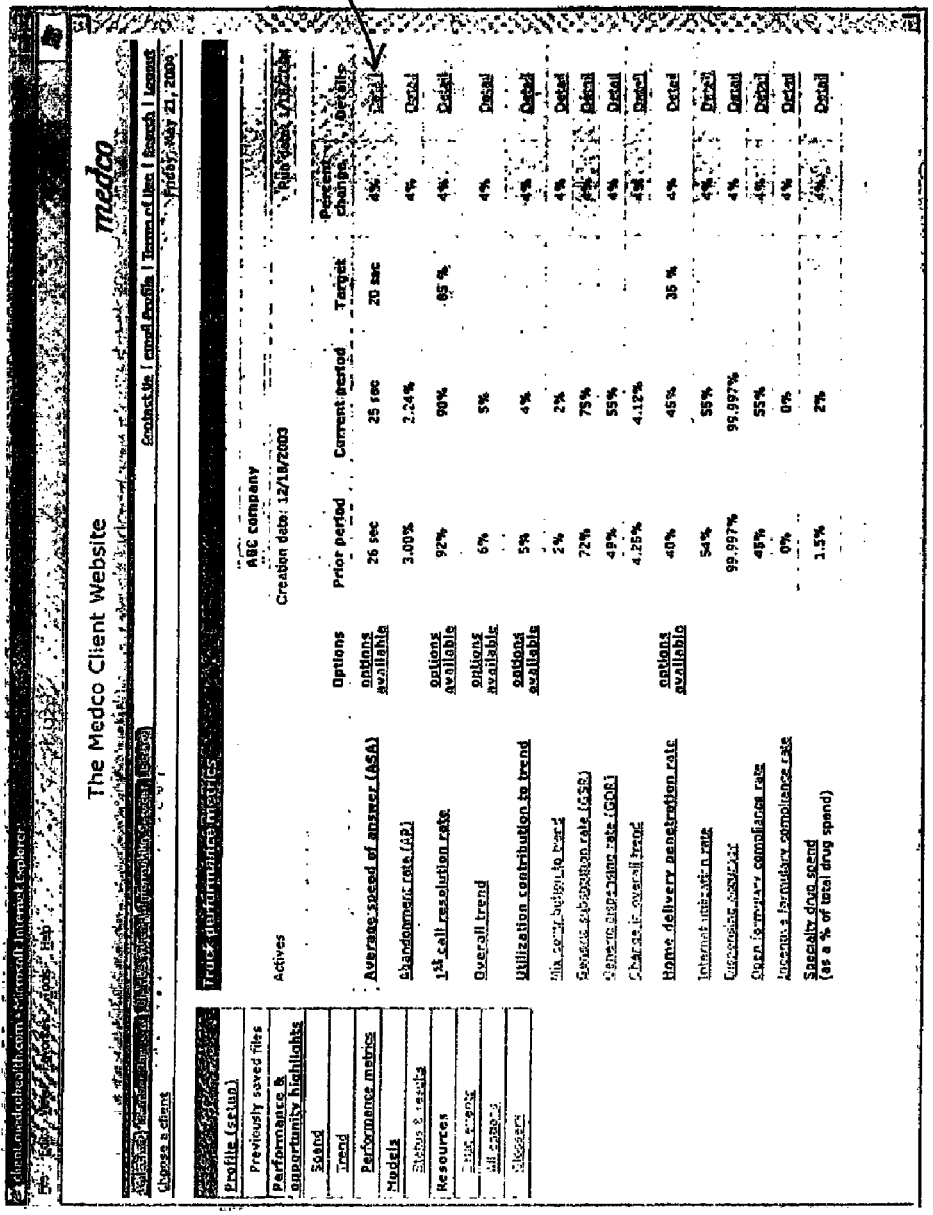
FIGS. 53 and 54 are illustrative performance metrics screens that may be provided by the prescription drug spend and trend application in accordance with some embodiments of the present invention.
Figure 54:
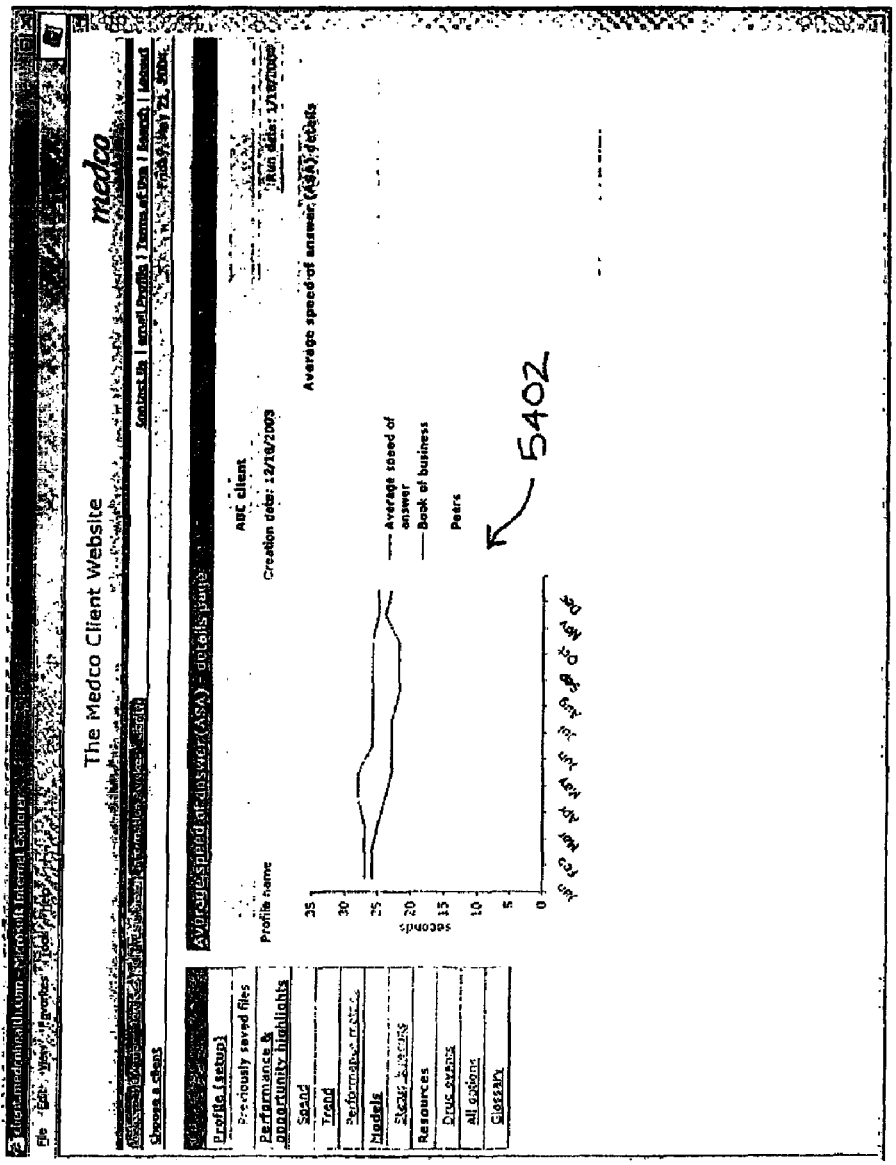

As described hereinabove, the spend and trend application of the present invention may provide a user with the ability to set a plurality of performance metrics and rule triggers in connection with a prescription drug plan. An illustrative performance metrics screen 5300 is provided in FIG. 53. Screen 5300 includes a list of performance metrics defined during set up of the plan profile. Plan performance that deviates from the established target may be provided, for example, in a different color than plan performance that is on-target. For example, any performance metric that deviates from the established target may be provided in red to indicate this deviation to the user. A user may view details in connection with a particular performance metric by selecting the respective "Detail" link in screen 5300. For example, if the user selects "Detail" link 5302, the spend and trend application may provide the user with screen 5400 of FIG. 54. Screen 5400 may provide details in connection with the "Average speed of answer" performance metric. In particular, screen 5400 includes a graphical region 5402 that provides a representation of the selected performance metric over time. Region 5402 includes representations of the particular plan's average speed of answer, as well as benchmarking representations of the average speed of answer for both the book of business and peers.

Figure 55:
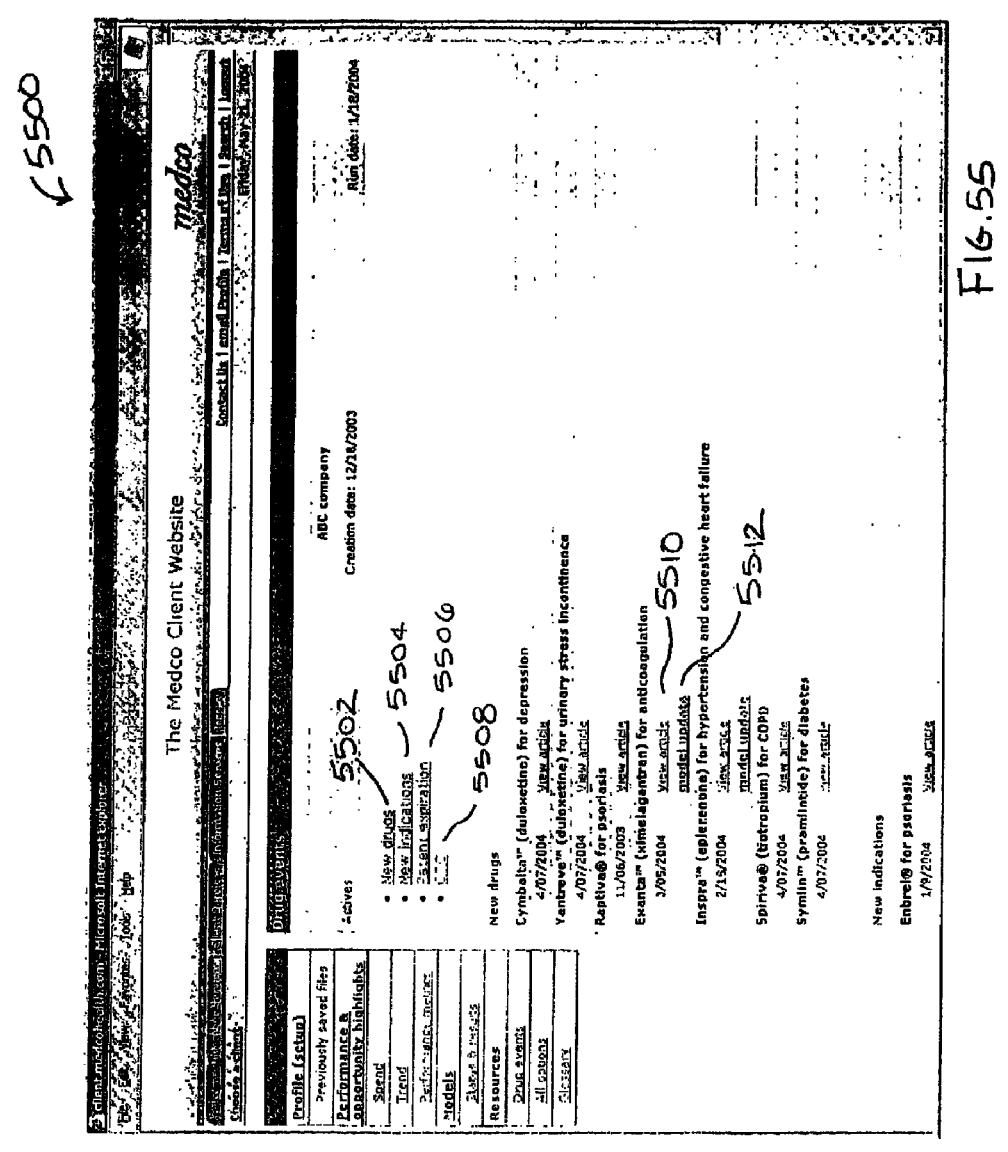

The spend and trend application of the present invention may provide a user with the ability to review upcoming drug events in the marketplace. FIG. 55 is an illustrative drug event screen 5500 that may be provided by the prescription drug spend and trend application in accordance with some embodiments of the present invention. Drug events are expected changes with respect to a drug or therapeutic chapter, category, or class of drugs that are likely to have an impact on spend, trend, or plan design for a prescription drug plan. Such drug events may include, for example, new drugs 5502, new indications 5504, patent expiration 5506, over-the-counter 5508, or any other suitable drug event. A user may obtain additional information on a specific drug event by selecting the "View article" link provided by the application in connection with that drug event. For example, if the user selects "View article" link 5510, then the application may provide the user with overlay 5600 of FIG. 56. Overlay 5600 provides the user with information in connection with the new drug Exanta™.

Referring back to FIG. 55, the application may provide the user with the ability to model the impact of a new drug event on the prescription drug plan. For example, the user may select "model update" link 5512 to model the impact of the introduction of the new drug Exanta™ on the prescription drug plan. In response to the selection of link 5512, the application may provide the user with modeling input and output screens substantially similar to those provided in connection with the options described hereinabove.

As described hereinabove, the spend and/or trend application of the present invention may analyze spend and/or trend for a prescription drug plan and perform various comparisons and calculations related thereto. One of ordinary skill would know how to utilize standard algorithms to implement the processes of the present invention based on the information provided in this application.

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Although the present invention has been described and illustrated in the foregoing exemplary embodiments, it is understood that the present disclosure has been made only by way of example, and that numerous changes in the details of implementation of the invention may be made without departing from the spirit and scope of the invention, which is limited only by the claims which follow.

What is claimed is:

1. A computer implemented method for simulating at least one change to a prescription drug plan having a plurality of members by a prescription drug plan management computer system, comprising:

receiving a request from a prescription drug plan administrator to simulate the at least one plan specific change to the prescription drug plan from a user computing device, wherein the at least one plan specific change comprises a change to a parameter from a plurality of parameters associated with the prescription drug plan for the plurality of members;

in response to receiving the request, retrieving data relating to the prescription drug plan from a database;

executing, using the prescription drug plan management computer system, a prescription drug plan simulation model using the retrieved data, wherein the model comprises a plurality of calculations performed by the computer to simulate the at least one plan specific change to the prescription drug plan for the plurality members; and electronically transmitting to the user computing device of a prescription drug plan administrator data resulting from the simulation of the at least one plan specific change to the prescription drug plan, wherein the data provides an indication of an overall impact on the prescription drug plan responsive to the at least one plan specific change based at least in part on the application of the model to the retrieved data for the plurality members, and wherein the overall impact on the prescription drug plan for the plurality members as a result of the plan specific change comprises at least one of gross cost, cost share, plan cost, per-member per-month cost, point of service attrition rate, clinical review rate, clinical review denial rate, total denial rate, and number of plan members impacted for the prescription drug plan;

wherein the at least one change comprises at least one of:

(i) a benefit design change for the prescription drug plan, wherein the model comprises at least one of:

a formulary options model comprising a plurality of calculations that determine a rebate impact of a change to at least one of formulary content and co-pays for the prescription drug plan;

a therapeutic class optimizer model comprising a plurality of calculations that estimate a rebate impact and a net cost impact of moving a particular drug on or off a formulary of the prescription drug plan for one or more therapeutic classes;

a dose optimization model comprising a plurality of calculations that determine an estimated financial impact and an estimated member impact of implementing dose optimization rules;

a quantity per dispensing event model comprising a plurality of calculations that determine an estimated financial impact and an estimated member impact of implementing quantity per dispensing event rules;

a smart rules model comprising a plurality of calculations that determine an estimated financial impact and an estimated member impact of implementing coverage authorization rules;

a traditional prior authorization model comprising a plurality of calculations that determine an estimated financial impact and an estimated member impact of implementing prior authorization rules;

a specialty model comprising a plurality of calculations that determine an estimated drug spend impact and an estimated discount impact associated with implementing a specialty pharmacy offering;

a new drug events model comprising a plurality of calculations that determine an estimated impact of a status change for a particular drug, the status change comprising at least one of an expiration of a patent for the drug, a new indication for the drug, a shift of the drug from prescription to over-the-counter, an introduction of the drug to the marketplace, and a withdrawal of the drug from the marketplace;

a Medicare coordination of benefits model comprising a plurality of calculations that determine an estimated financial impact of implementing a Medicare Part B subrogation program for home delivery claims; and an inclusions/exclusions model comprising a plurality of calculations that determine an estimated impact of including or excluding a particular drug in the prescription drug plan that is typically considered for exclusion from coverage; and (ii) a plan design change for the prescription drug plan, wherein the model comprises at least one of:

a member cost share model comprising a plurality of calculations that determine an impact of changes to at least one of open and incentive co-pay prescription drug plan structures comprising a plurality of tiers;

a retail refill allowance model comprising a plurality of calculations that determine an impact of a stand-alone retail refill allowance at a user specified threshold;

a home delivery advantage model comprising a plurality of calculations that determine an impact of a stand-alone home delivery advantage comprising retail and home delivery co-pay alignment;

a member pay the difference model comprising a plurality of calculations that determine an impact of at least one of a managed and sensitive member pay the difference program;

a generic bundle model comprising a plurality of sub-models related to generic drug utilization including at least one of dose duration, step therapy, incentive co-pay, and member pay the difference;

an out of pocket maximum model comprising a plurality of calculations that determine an impact of an out of pocket maximum both with and without a change to deductible or co-pay;

a deductibles model comprising a plurality of calculations that determine an impact of deductibles both with and without a change to out of pocket cost and co-pay;

a patient safety program model comprising a plurality of calculations that determine an estimated financial impact of implementing a patient safety program for the prescription drug plan;

a benefit cap model comprising a plurality of calculations that determine an impact of a benefit cap for the prescription drug plan; and a retail access density model comprising a plurality of calculations that determine a member impact of removing at least one chain prescription drug retailer from the prescription drug plan.

2. The method of claim 1, wherein the impact on the prescription drug plan is a financial impact.

3. The method of claim 1, wherein the impact on the prescription drug plan is a member impact.

4. The method of claim 1, further comprising:

receiving a request from the user computing device to process at least one of spend and trend for the prescription drug plan;

in response to receiving the request to process the at least one of spend and trend, retrieving data related to the prescription drug plan from the database;

processing, by the computer, the at least one of spend and trend for the prescription drug plan using the retrieved data;

determining, by the computer, whether at least one option to reduce the at least one of spend and trend for the prescription drug plan is available; and if the at least one option is available, providing an indication of the at least one option to the user computing device, wherein the at least one option comprises the at least one change to the prescription drug plan, wherein spend for the prescription drug plan comprises a cost of prescription drugs under the prescription drug plan, and trend for the prescription drug plan comprises a rate of change in prescription drug spending for the prescription drug plan over time.

5. The method of claim 1, further comprising:
receiving an indication from the user computing device of a performance metric for a parameter of the prescription drug plan;
receiving a request from the user computing device to process at least one of spend and trend for the prescription drug plan;
in response to receiving the request to process the at least one of spend and trend, retrieving data related to the prescription drug plan from the database;
comparing the performance metric for the parameter to retrieved data related to the parameter; and
if the retrieved data deviates from the performance metric and if at least one option is available to reduce the deviation, providing an indication to the user computing device of the at least one option, wherein the at least one option comprises the at least one change to the prescription drug plan.

6. The method of claim 1, further comprising:
receiving a request from the user computing device to process at least one of spend and trend for the prescription drug plan;
in response to receiving the request to process the at least one of spend and trend, retrieving data related to the prescription drug plan from the database;
processing, by the computer, the at least one of spend and trend for the prescription drug plan using the retrieved data, wherein the processing comprises determining components of the at least one of spend and trend having an impact on the at least one of spend and trend; and
if at least one option is available to reduce the impact on the at least one of spend and trend for at least one of the components, providing the user computing device with an indication of the at least one option, wherein the at least one option comprises the at least one change to the prescription drug plan, and
wherein spend for the prescription drug plan comprises a cost of prescription drugs under the prescription drug plan, and trend for the prescription drug plan comprises a rate of change in prescription drug spending for the prescription drug plan over time.

7. The method of claim 1, further comprising:
determining whether a status change is projected for a particular drug in a marketplace; and
if at least one option is available, providing an indication of the at least one option to the user computing device, wherein the at least one option is related to the status change for the particular drug, and wherein the at least one option comprises the at least one change to the prescription drug plan.

8. The method of claim 1, further comprising:
providing the user computing device with an indication of a plurality of available models for simulating at least one change to the prescription drug plan; and
receiving a selection from the user computing device of a particular model of the plurality models for application to the retrieved data.

9. The method of claim 1, wherein the at least one change comprises a first change and a second change, and wherein the first change has a corresponding first model and the second change has a corresponding second model, the method further comprising:
receiving a request to simulate the first and second changes to the prescription drug plan from the user computing device;
applying the first and second models to the retrieved data, wherein the first and second models comprise a plurality of calculations to simulate the respective first and second changes to the prescription drug plan; and
providing the user computing device with an indication of an impact on the prescription drug plan responsive to the first and second changes based at least in part on the application of the first and second models to the retrieved data.

10. The method of claim 1, further comprising:
receiving a request to simulate the at least one change to the prescription drug plan from a prescription drug plan administrator computing device used by a prescription drug plan administrator of the prescription drug plan;
in response to receiving the request, determining the prescription drug plan associated with the prescription drug plan administrator from a plurality of prescription drug plans administered by the prescription drug plan management computer system, and retrieving data related to the prescription drug plan from a database;
executing, using the prescription drug plan management computer system, a prescription drug plan simulation model to the retrieved data, wherein the model comprises a plurality of calculations performed by the computer to simulate the at least one change to the prescription drug plan.

11. A prescription drug plan management computer system for simulating at least one change to a prescription drug plan, comprising:
a computer system in communication with a user computing device and a database, wherein the computer system is configured to:
receive a request to simulate the at least one plan specific change to the prescription drug plan having a plurality of members from a user computing device, wherein the at least one change comprises a change to a parameter from a plurality of parameters associated with the prescription drug plan having the plurality of members;
in response to receiving the request, retrieve data relating to the prescription drug plan from a database;
execute, by the computer system, a computer simulation model using the retrieved data, wherein the model comprises a plurality of calculations to simulate the at least one plan specific change to the prescription drug plan having the plurality of members; and
electronically transmit, by the computer system, to the user computing device with data resulting from the simulation of the at least one plan specific change to the prescription drug plan, wherein the data provides an indication of an overall impact on the prescription drug plan responsive to the at least one plan specific change based at least in part on the application of the model to the retrieved data, and wherein the overall impact on the prescription drug plan as a result of the plan specific change comprises at least one of gross cost, cost share, plan cost, per-member per-month cost, point of service attrition rate, clinical review rate, clinical review denial rate, total denial rate, and number of plan members impacted for the prescription drug plan;
wherein the at least one change comprises at least one of:
(i) a benefit design change for the prescription drug plan, wherein the model comprises at least one of:

a formulary options model comprising a plurality of calculations that determine a rebate impact of a change to at least one of formulary content and co-pays for the prescription drug plan;

a therapeutic class optimizer model comprising a plurality of calculations that estimate a rebate impact and a net cost impact of moving a particular drug on or off a formulary of the prescription drug plan for one or more therapeutic classes;

a dose optimization model comprising a plurality of calculations that determine an estimated financial impact and an estimated member impact of implementing dose optimization rules;

a quantity per dispensing event model comprising a plurality of calculations that determine an estimated financial impact and an estimated member impact of implementing quantity per dispensing event rules;

a smart rules model comprising a plurality of calculations that determine an estimated financial impact and an estimated member impact of implementing coverage authorization rules;

a traditional prior authorization model comprising a plurality of calculations that determine an estimated financial impact and an estimated member impact of implementing prior authorization rules;

a specialty model comprising a plurality of calculations that determine an estimated drug spend impact and an estimated discount impact associated with implementing a specialty pharmacy offering;

a new drug events model comprising a plurality of calculations that determine an estimated impact of a status change for a particular drug, the status change comprising at least one of an expiration of a patent for the drug, a new indication for the drug, a shift of the drug from prescription to over-the-counter, an introduction of the drug to the marketplace, and a withdrawal of the drug from the marketplace;

a Medicare coordination of benefits model comprising a plurality of calculations that determine an estimated financial impact of implementing a Medicare Part B subrogation program for home delivery claims; and an inclusions/exclusions model comprising a plurality of calculations that determine an estimated impact of including or excluding a particular drug in the prescription drug plan that is typically considered for exclusion from coverage; and (ii) a plan design change for the prescription drug plan, wherein the model comprises at least one of:

a member cost share model comprising a plurality of calculations that determine an impact of changes to at least one of open and incentive co-pay prescription drug plan structures comprising a plurality of tiers;

a retail refill allowance model comprising a plurality of calculations that determine an impact of a stand-alone retail refill allowance at a user specified threshold;

a home delivery advantage model comprising a plurality of calculations that determine an impact of a stand-alone home delivery advantage comprising retail and home delivery co-pay alignment;

a member pay the difference model comprising a plurality of calculations that determine an impact of at least one of a managed and sensitive member pay the difference program;

a generic bundle model comprising a plurality of sub-models related to generic drug utilization including at least one of dose duration, step therapy, incentive co-pay, and member pay the difference;

an out of pocket maximum model comprising a plurality of calculations that determine an impact of an out of pocket maximum both with and without a change to deductible or co-pay;

a deductibles model comprising a plurality of calculations that determine an impact of deductibles both with and without a change to out of pocket cost and co-pay;

a patient safety program model comprising a plurality of calculations that determine an estimated financial impact of implementing a patient safety program for the prescription drug plan;

a benefit cap model comprising a plurality of calculations that determine an impact of a benefit cap for the prescription drug plan; and a retail access density model comprising a plurality of calculations that determine a member impact of removing at least one chain prescription drug retailer from the prescription drug plan.

12. The system of claim 11, wherein the impact on the prescription drug plan is a financial impact.

13. The system of claim 11, wherein the impact on the prescription drug plan is a member impact.

14. The system of claim 11, wherein the computer system is further configured to:

receive a request from the user computing device to process at least one of spend and trend for the prescription drug plan;

in response to receipt of the request to process the at least one of spend and trend, retrieve data related to the prescription drug plan from the database;

process the at least one of spend and trend for the prescription drug plan using the retrieved data;

determine whether at least one option to reduce the at least one of spend and trend for the prescription drug plan is available; and if the at least one option is available, provide an indication of the at least one option to the user computing device, wherein the at least one option comprises the at least one change to the prescription drug plan, wherein spend for the prescription drug plan comprises a cost of prescription drugs under the prescription drug plan, and trend for the prescription drug plan comprises a rate of change in prescription drug spending for the prescription drug plan over time.

15. The system of claim 11, wherein the computer system is further configured to:

receive an indication from the user computing device of a performance metric for a parameter of the prescription drug plan;

receive a request from the user computing device to process at least one of spend and trend for the prescription drug plan;

in response to receipt of the request to process the at least one of spend and trend, retrieve data related to the prescription drug plan from the database;

compare the performance metric for the parameter to retrieved data related to the parameter; and if the retrieved data deviates from the performance metric and if at least one option is available to reduce the deviation, provide an indication to the user computing device of the at least one option, wherein the at least one option comprises the at least one change to the prescription drug plan.

16. The system of claim 11, wherein the computer system is further configured to:

receive a request from the user computing device to process at least one of spend and trend for the prescription drug plan;

in response to receipt of the request to process the at least one of spend and trend, retrieve data related to the prescription drug plan from the database;

process the at least one of spend and trend for the prescription drug plan using the retrieved data, wherein the server is further configured to determine components of the at least one of spend and trend having an impact on the at least one of spend and trend; and if at least one option is available to reduce the impact on the at least one of spend and trend for at least one of the components, provide the user computing device with an indication of the at least one option, wherein the at least one option comprises the at least one change to the prescription drug plan, wherein the spend for the prescription drug plan comprises a cost of prescription drugs under the prescription drug plan, and the trend for the prescription drug plan comprises a rate of change in prescription drug spending for the prescription drug plan over time.

17. The system of claim 11, wherein the computer system is further configured to:

determine whether a status change is projected for a particular drug in a marketplace; and if at least one option is available, provide an indication of the at least one option to the user computing device, wherein the at least one option is related to the status change for the particular drug, and wherein the at least one option comprises the at least one change to the prescription drug plan.

18. The system of claim 11, wherein the server computer system is further configured to:

provide the user computing device with an indication of a plurality of available models for simulating at least one change to the prescription drug plan; and receive a selection from the user computing device of a particular model of the plurality models for application to the retrieved data.

19. The system of claim 11, wherein the at least one change comprises a first change and a second change, wherein the first change has a corresponding first model and the second change has a corresponding second model, and wherein the computer system is further configured to:

receive a request to simulate the first and second changes to the prescription drug plan from the user computing device;

apply the first and second models to the retrieved data, wherein the first and second models comprise a plurality of calculations to simulate the respective first and second changes to the prescription drug plan; and provide the user computing device with an indication of an impact on the prescription drug plan responsive to the first and second changes based at least in part on the application of the first and second models to the retrieved data.

20. The system of claim 11, wherein the computer system is further configured to: receive at least one modeling input from the user computing device, wherein the at least one modeling input indicates a value for at least one parameter of the model.

21. The system of claim 11, wherein the computer system is configured to:

receive a request to simulate the at least one change to the prescription drug plan from a prescription drug plan administrator computing device used by a prescription drug plan administrator of the prescription drug plan; in response to the request, determine the prescription drug plan associated with the prescription drug plan administrator from a plurality of prescription drug plans administered by the prescription drug plan management computer system, and retrieving data related to the prescription drug plan from a database;

execute, using the prescription drug plan management computer system, a prescription drug plan simulation model to the retrieved data, wherein the model comprises a plurality of calculations performed by the computer to simulate the at least one change to the prescription drug plan.

* * * * *